US011286307B2

(12) United States Patent
Adelman et al.

(10) Patent No.: US 11,286,307 B2
(45) Date of Patent: Mar. 29, 2022

(54) PLASMA KALLIKREIN INHIBITORS AND USES THEREOF FOR TREATING HEREDITARY ANGIOEDEMA ATTACK

(71) Applicant: Takeda Pharmaceutical Company Limited, Osaka (JP)

(72) Inventors: Burt Adelman, Concord, MA (US); Yung Chyung, Lexington, MA (US); Jennifer Schranz, King of Prussia, PA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 270 days.

(21) Appl. No.: 16/061,103

(22) PCT Filed: Dec. 9, 2016

(86) PCT No.: PCT/US2016/065980
§ 371 (c)(1),
(2) Date: Jun. 11, 2018

(87) PCT Pub. No.: WO2017/100679
PCT Pub. Date: Jun. 15, 2017

(65) Prior Publication Data
US 2018/0362664 A1 Dec. 20, 2018

Related U.S. Application Data

(60) Provisional application No. 62/395,833, filed on Sep. 16, 2016, provisional application No. 62/266,175, filed on Dec. 11, 2015, provisional application No. 62/266,192, filed on Dec. 11, 2015.

(51) Int. Cl.
*A61P 29/00* (2006.01)
*A61K 39/395* (2006.01)
*C07K 16/40* (2006.01)
*A61K 39/00* (2006.01)

(52) U.S. Cl.
CPC ......... *C07K 16/40* (2013.01); *A61K 39/3955* (2013.01); *A61P 29/00* (2018.01); *A61K 2039/505* (2013.01); *A61K 2039/54* (2013.01); *A61K 2039/545* (2013.01); *A61K 2039/57* (2013.01); *C07K 2317/76* (2013.01)

(58) Field of Classification Search
None
See application file for complete search history.

(56) References Cited

U.S. PATENT DOCUMENTS

| 3,682,776 A | 8/1972 | Grundmann et al. |
| 3,691,016 A | 9/1972 | Patel |
| 3,969,287 A | 7/1976 | Jaworek et al. |
| 4,118,481 A | 10/1978 | Schnabel et al. |
| 4,153,687 A | 5/1979 | Schnabel et al. |
| 4,179,337 A | 12/1979 | Davis et al. |
| 4,195,128 A | 3/1980 | Hildebrand et al. |
| 4,229,537 A | 10/1980 | Hodgins et al. |
| 4,247,642 A | 1/1981 | Hirohara et al. |
| 4,330,440 A | 5/1982 | Ayers et al. |
| 4,377,572 A | 3/1983 | Schwarz et al. |
| 4,399,216 A | 8/1983 | Axel et al. |
| 4,595,674 A | 6/1986 | Tschesche et al. |
| 4,609,725 A | 9/1986 | Brady et al. |
| 4,634,665 A | 1/1987 | Axel et al. |
| 4,657,893 A | 4/1987 | Krantz et al. |
| 4,845,242 A | 7/1989 | Powers et al. |
| 4,881,175 A | 11/1989 | Ladner |
| 4,946,778 A | 8/1990 | Ladner et al. |
| 4,966,852 A | 10/1990 | Wun et al. |
| 5,045,452 A | 9/1991 | Spragg et al. |
| 5,106,833 A | 4/1992 | Broze, Jr. et al. |
| 5,118,668 A | 6/1992 | Auerswald et al. |
| 5,166,133 A | 11/1992 | Houston et al. |
| 5,179,017 A | 1/1993 | Axel et al. |
| 5,212,091 A | 5/1993 | Diaz-Collier et al. |
| 5,223,409 A | 6/1993 | Ladner et al. |
| 5,260,203 A | 11/1993 | Ladner et al. |
| 5,278,144 A | 1/1994 | Wolf |
| 5,278,285 A | 1/1994 | Ebbers et al. |

(Continued)

FOREIGN PATENT DOCUMENTS

| AT | 275583 T | 9/2004 |
| BR | 112015017195 A2 | 7/2017 |

(Continued)

OTHER PUBLICATIONS

Zuraw (The New England Journal of Medicine, 359(10):1027-1036, 2008).*
Zuraw (Allergy Asthma Clin Immunol. 6:23 pp. 1-8, 2010).*
International Search Report and Written Opinion for Application No. PCT/US2016/065980 dated Mar. 1, 2017.
International Preliminary Report on Patentability for Application No. PCT/US2016/065980 dated Jun. 21, 2018.
[No Author Listed] Dyax's DX-2930 granted Orphan Drug designation in hereditary angioedema. Dec. 6, 2013.

(Continued)

*Primary Examiner* — Patricia Duffy
(74) *Attorney, Agent, or Firm* — Wolf, Greenfield & Sacks, P.C.

(57) ABSTRACT

Provided herein are plasma kallikrein antibodies binding to active plasma kallikrein and methods of using such antibodies in treating and preventing hereditary angioedema attack, such method may involve a first treatment period and optionally, a second treatment period. Also provided are methods of using such antibodies in treating hereditary angioedema involving a single dose of the antibody to a subject who has undergone a prior HAE treatment, followed by multiple doses of the same antibody if the subject experiences an HAE attack after the single dose.

19 Claims, 3 Drawing Sheets
Specification includes a Sequence Listing.

(56) References Cited

U.S. PATENT DOCUMENTS

| | | |
|---|---|---|
| 5,312,736 A | 5/1994 | Rasmussen et al. |
| 5,372,933 A | 12/1994 | Zamarron et al. |
| 5,373,090 A | 12/1994 | Norris et al. |
| 5,378,614 A | 1/1995 | Petersen et al. |
| 5,407,915 A | 4/1995 | Fritz et al. |
| 5,409,895 A | 4/1995 | Morishita et al. |
| 5,426,224 A | 6/1995 | Lee et al. |
| 5,441,931 A | 8/1995 | Sprecher et al. |
| 5,444,156 A | 8/1995 | Veloso et al. |
| 5,446,090 A | 8/1995 | Harris |
| 5,455,338 A | 10/1995 | Sprecher et al. |
| 5,466,783 A | 11/1995 | Wun et al. |
| 5,563,123 A | 10/1996 | Innis et al. |
| 5,576,294 A | 11/1996 | Norris et al. |
| 5,583,107 A | 12/1996 | Wolf et al. |
| 5,585,089 A | 12/1996 | Queen et al. |
| 5,589,359 A | 12/1996 | Innis et al. |
| 5,618,696 A | 4/1997 | Norris et al. |
| 5,629,176 A | 5/1997 | Bjørn et al. |
| 5,635,187 A | 6/1997 | Bathurst et al. |
| 5,648,331 A | 7/1997 | Koudsi et al. |
| 5,663,143 A | 9/1997 | Ley et al. |
| 5,672,662 A | 9/1997 | Harris et al. |
| 5,677,146 A | 10/1997 | Sprecher et al. |
| 5,693,761 A | 12/1997 | Queen et al. |
| 5,693,762 A | 12/1997 | Queen et al. |
| 5,695,760 A | 12/1997 | Faanes et al. |
| 5,696,088 A | 12/1997 | Innis et al. |
| 5,719,041 A | 2/1998 | Lazarus et al. |
| 5,736,364 A | 4/1998 | Kelley et al. |
| 5,739,208 A | 4/1998 | Harris |
| 5,747,449 A | 5/1998 | Lasters et al. |
| 5,770,568 A | 6/1998 | Auerswald et al. |
| 5,780,265 A | 7/1998 | Dennis et al. |
| 5,786,328 A | 7/1998 | Dennis et al. |
| 5,795,865 A | 8/1998 | Markland et al. |
| 5,795,954 A | 8/1998 | Lazarus et al. |
| 5,800,385 A | 9/1998 | Demopulos et al. |
| 5,804,376 A | 9/1998 | Braxton et al. |
| 5,834,244 A | 11/1998 | Dennis et al. |
| 5,843,895 A | 12/1998 | Lazarus et al. |
| 5,849,992 A | 12/1998 | Meade et al. |
| 5,853,723 A | 12/1998 | Jacobs et al. |
| 5,863,893 A | 1/1999 | Dennis et al. |
| 5,869,637 A | 2/1999 | Au-Young et al. |
| 5,874,407 A | 2/1999 | Kelley et al. |
| 5,880,256 A | 3/1999 | Dennis et al. |
| 5,900,461 A | 5/1999 | Harris |
| 5,914,316 A | 6/1999 | Brown et al. |
| 5,932,462 A | 8/1999 | Harris et al. |
| 5,951,974 A | 9/1999 | Gilbert et al. |
| 5,962,266 A | 10/1999 | White et al. |
| 5,990,237 A | 11/1999 | Bentley et al. |
| 5,994,125 A | 11/1999 | Markland et al. |
| 6,001,596 A | 12/1999 | Hillman et al. |
| 6,004,579 A | 12/1999 | Bathurst et al. |
| 6,008,196 A | 12/1999 | Curran et al. |
| 6,010,880 A | 1/2000 | Markland et al. |
| 6,013,448 A | 1/2000 | Braxton et al. |
| 6,013,763 A | 1/2000 | Braisted et al. |
| 6,017,723 A | 1/2000 | Rao et al. |
| 6,057,287 A | 5/2000 | Markland et al. |
| 6,063,764 A | 5/2000 | Creasey et al. |
| 6,071,723 A | 6/2000 | Markland et al. |
| 6,087,473 A | 7/2000 | Conklin et al. |
| 6,090,916 A | 7/2000 | Vlasuk et al. |
| 6,103,499 A | 8/2000 | Markland et al. |
| 6,103,500 A | 8/2000 | Innis et al. |
| 6,113,896 A | 9/2000 | Lazarus et al. |
| 6,126,933 A | 10/2000 | Warne et al. |
| 6,159,938 A | 12/2000 | Gyorkos et al. |
| 6,171,587 B1 | 1/2001 | Wun et al. |
| 6,174,721 B1 | 1/2001 | Innis et al. |
| 6,180,607 B1 | 1/2001 | Davies et al. |
| 6,214,966 B1 | 4/2001 | Harris |
| 6,242,414 B1 | 6/2001 | Johnson et al. |
| 6,258,351 B1 | 7/2001 | Harris |
| 6,261,279 B1 | 7/2001 | Demopulos et al. |
| 6,306,884 B1 | 10/2001 | Buckman et al. |
| 6,333,402 B1 | 12/2001 | Markland et al. |
| 6,348,558 B1 | 2/2002 | Harris et al. |
| 6,362,254 B2 | 3/2002 | Harris et al. |
| 6,362,276 B1 | 3/2002 | Harris et al. |
| 6,376,604 B2 | 4/2002 | Kozlowski |
| 6,407,213 B1 | 6/2002 | Carter et al. |
| 6,413,507 B1 | 7/2002 | Bentley et al. |
| 6,423,498 B1 | 7/2002 | Markland et al. |
| 6,432,397 B1 | 8/2002 | Harris |
| 6,455,639 B1 | 9/2002 | Yasukohchi et al. |
| 6,472,195 B2 | 10/2002 | Hillman et al. |
| 6,515,100 B2 | 2/2003 | Harris |
| 6,534,276 B1 | 3/2003 | Wun et al. |
| 6,548,262 B2 | 4/2003 | Gentz et al. |
| 6,576,235 B1 | 6/2003 | Williams et al. |
| 6,583,108 B1 | 6/2003 | Tamburini et al. |
| 6,610,281 B2 | 8/2003 | Harris |
| 6,624,246 B2 | 9/2003 | Kozlowski |
| 6,664,331 B2 | 12/2003 | Harris et al. |
| 6,689,582 B1 | 2/2004 | Davies et al. |
| 6,710,125 B2 | 3/2004 | Kozlowski |
| 6,774,180 B2 | 8/2004 | Kozlowski et al. |
| 6,783,960 B2 | 8/2004 | Innis et al. |
| 6,783,965 B1 | 8/2004 | Sherman et al. |
| 6,806,360 B2 | 10/2004 | Wun et al. |
| 6,814,982 B2 | 11/2004 | Poncin et al. |
| 6,914,135 B2 | 7/2005 | Sheppard et al. |
| 6,953,674 B2 | 10/2005 | Markland et al. |
| 6,989,369 B2 | 1/2006 | Ladner et al. |
| 7,064,107 B2 | 6/2006 | Ladner et al. |
| 7,067,144 B2 | 6/2006 | Demopulos et al. |
| 7,078,383 B2 | 7/2006 | Ley et al. |
| 7,153,829 B2 | 12/2006 | Ladner et al. |
| 7,166,576 B2 | 1/2007 | Cicardi et al. |
| 7,235,530 B2 | 6/2007 | Blair et al. |
| 7,276,480 B1 | 10/2007 | Ladner et al. |
| 7,550,427 B2 | 6/2009 | Ley et al. |
| 7,628,983 B2 | 12/2009 | Markland et al. |
| 7,704,949 B2 | 4/2010 | Ladner et al. |
| 7,718,617 B2 | 5/2010 | Cicardi et al. |
| 7,811,991 B2 | 10/2010 | Ladner et al. |
| 7,851,442 B2 | 12/2010 | Ladner et al. |
| 7,919,462 B2 | 4/2011 | Markland et al. |
| 8,034,775 B2 | 10/2011 | Ladner et al. |
| 8,124,586 B2 | 2/2012 | Ladner et al. |
| 8,188,045 B2 | 5/2012 | Blair et al. |
| 8,283,321 B2 | 10/2012 | Markland et al. |
| 8,816,055 B2 | 8/2014 | Sexton et al. |
| 8,822,653 B2 | 9/2014 | Sexton et al. |
| 9,266,964 B2 | 2/2016 | Sexton et al. |
| 10,316,095 B2 * | 6/2019 | Fowler ............... A61K 39/3955 |
| 10,336,832 B2 | 7/2019 | Sexton et al. |
| 10,370,453 B2 | 8/2019 | Sexton et al. |
| 10,428,158 B2 | 10/2019 | Conley et al. |
| 2001/0027180 A1 | 10/2001 | Isaacs |
| 2002/0102703 A1 | 8/2002 | Sheppard et al. |
| 2002/0111460 A1 | 8/2002 | Holloway |
| 2003/0012969 A1 | 1/2003 | Clark |
| 2003/0096733 A1 | 5/2003 | Ny et al. |
| 2003/0100070 A1 | 5/2003 | Holloway |
| 2003/0113726 A1 | 6/2003 | Tsuchihashi et al. |
| 2003/0114372 A1 | 6/2003 | White et al. |
| 2003/0138417 A1 | 7/2003 | Kaisheva et al. |
| 2003/0153046 A1 | 8/2003 | Jensen et al. |
| 2003/0175919 A1 | 9/2003 | Ley et al. |
| 2003/0223977 A1 | 12/2003 | Ley et al. |
| 2004/0038893 A1 | 2/2004 | Ladner et al. |
| 2004/0049018 A1 | 3/2004 | Bailon et al. |
| 2004/0053206 A1 | 3/2004 | Cicardi et al. |
| 2004/0062746 A1 | 4/2004 | Martinez et al. |
| 2004/0062748 A1 | 4/2004 | Martinez et al. |
| 2004/0106747 A1 | 6/2004 | Bailon et al. |
| 2004/0126361 A1 | 7/2004 | Saifer et al. |
| 2004/0152633 A1 | 8/2004 | Jorgensen et al. |
| 2004/0171794 A1 | 9/2004 | Ladner et al. |

(56) References Cited

U.S. PATENT DOCUMENTS

| | | |
|---|---|---|
| 2004/0180827 A1 | 9/2004 | Chen et al. |
| 2004/0209243 A1 | 10/2004 | Nixon et al. |
| 2005/0004021 A1 | 1/2005 | Sprecher et al. |
| 2005/0075665 A1 | 4/2005 | Brenzel et al. |
| 2005/0089515 A1 | 4/2005 | Ley et al. |
| 2005/0164928 A1 | 7/2005 | Ladner et al. |
| 2005/0164945 A1 | 7/2005 | Nixon et al. |
| 2005/0180977 A1 | 8/2005 | Nixon et al. |
| 2006/0069020 A1 | 3/2006 | Blair et al. |
| 2006/0194727 A1 | 8/2006 | Ladner et al. |
| 2006/0228331 A1 | 10/2006 | Peschke et al. |
| 2006/0264603 A1 | 11/2006 | Markland et al. |
| 2007/0020252 A1 | 1/2007 | Ladner et al. |
| 2007/0041959 A1 | 2/2007 | Ley et al. |
| 2007/0049522 A1 | 3/2007 | Ladner et al. |
| 2007/0065407 A1 | 3/2007 | Patten et al. |
| 2007/0079096 A1 | 4/2007 | Chen |
| 2007/0100133 A1 | 5/2007 | Beals et al. |
| 2007/0117752 A1 | 5/2007 | Larsen et al. |
| 2007/0213275 A1 | 9/2007 | Clark et al. |
| 2007/0249807 A1 | 10/2007 | Ladner et al. |
| 2007/0253949 A1 | 11/2007 | Golz et al. |
| 2008/0038276 A1 | 2/2008 | Sinha et al. |
| 2008/0038748 A1 | 2/2008 | Kojima et al. |
| 2008/0050716 A1 | 2/2008 | Cicardi et al. |
| 2008/0064637 A1 | 3/2008 | Ladner et al. |
| 2008/0076712 A1 | 3/2008 | Ladner et al. |
| 2008/0131426 A1 | 6/2008 | Ladner et al. |
| 2008/0139473 A1 | 6/2008 | Ladner et al. |
| 2008/0152656 A1 | 6/2008 | Ladner et al. |
| 2008/0182283 A1 | 7/2008 | Markland et al. |
| 2008/0188409 A1 | 8/2008 | Blair et al. |
| 2008/0200646 A1 | 8/2008 | Ladner et al. |
| 2008/0221031 A1 | 9/2008 | Blair et al. |
| 2008/0226655 A1 | 9/2008 | Ladner et al. |
| 2008/0255025 A1 | 10/2008 | Ladner |
| 2008/0260752 A1 | 10/2008 | Ladner et al. |
| 2008/0299050 A1 | 12/2008 | Bortz et al. |
| 2009/0023651 A1 | 1/2009 | Markland et al. |
| 2009/0062195 A1 | 3/2009 | Ladner et al. |
| 2009/0075887 A1 | 3/2009 | McPherson |
| 2009/0082267 A1 | 3/2009 | Ladner et al. |
| 2009/0105142 A1 | 4/2009 | Moscicki |
| 2009/0117130 A1 | 5/2009 | Ladner et al. |
| 2009/0123475 A9 | 5/2009 | Siegel |
| 2009/0215119 A1 | 8/2009 | Ladner |
| 2009/0221480 A1 | 9/2009 | Blair et al. |
| 2009/0227494 A1 | 9/2009 | Blair et al. |
| 2009/0227495 A1 | 9/2009 | Blair et al. |
| 2009/0233852 A1 | 9/2009 | Blair et al. |
| 2009/0234009 A1 | 9/2009 | Blair et al. |
| 2009/0247452 A1 | 10/2009 | Ellis et al. |
| 2009/0247453 A1 | 10/2009 | Blair et al. |
| 2009/0264350 A1 | 10/2009 | Blair et al. |
| 2010/0034805 A1 | 2/2010 | Ladner et al. |
| 2010/0183625 A1 | 7/2010 | Sternlicht |
| 2010/0273721 A1 | 10/2010 | Belichard |
| 2010/0285507 A1 | 11/2010 | Cho et al. |
| 2010/0286061 A1 | 11/2010 | Devy et al. |
| 2011/0008762 A1 | 1/2011 | Cicardi et al. |
| 2011/0086801 A1 | 4/2011 | Ladner et al. |
| 2011/0136746 A1 | 6/2011 | Markland et al. |
| 2011/0200611 A1 | 8/2011 | Sexton |
| 2012/0201756 A1 | 8/2012 | Sexton |
| 2012/0264798 A1 | 10/2012 | Sinha et al. |
| 2012/0328517 A1 | 12/2012 | Markland et al. |
| 2013/0012438 A1 | 1/2013 | Blair et al. |
| 2013/0216556 A1 | 8/2013 | Fowler et al. |
| 2014/0302048 A1 | 10/2014 | Sexton et al. |
| 2014/0303357 A1 | 10/2014 | Lim et al. |
| 2014/0335023 A1 | 11/2014 | Sexton et al. |
| 2015/0274841 A1 | 10/2015 | Conley et al. |
| 2015/0362492 A1 | 12/2015 | Joseph et al. |
| 2016/0017055 A1 | 1/2016 | Nixon et al. |
| 2016/0102150 A1 | 4/2016 | Sexton et al. |
| 2017/0002094 A1 | 1/2017 | Sexton et al. |
| 2018/0002447 A1 | 1/2018 | Sexton et al. |
| 2018/0002448 A1 | 1/2018 | Sexton et al. |
| 2018/0002449 A1 | 1/2018 | Sexton et al. |
| 2018/0037664 A1 | 2/2018 | Sexton et al. |
| 2018/0037665 A1 | 2/2018 | Sexton et al. |
| 2018/0037666 A1 | 2/2018 | Sexton et al. |
| 2018/0298110 A1 | 10/2018 | Chyung et al. |
| 2019/0185580 A1 | 6/2019 | Nixon et al. |
| 2020/0017602 A1 | 1/2020 | Sexton et al. |
| 2020/0109213 A1 | 4/2020 | Sexton et al. |
| 2020/0109214 A1 | 4/2020 | Peng et al. |
| 2020/0115469 A1 | 4/2020 | Conley et al. |
| 2020/0317815 A1 | 10/2020 | Mendivil Medina et al. |

FOREIGN PATENT DOCUMENTS

| | | |
|---|---|---|
| CA | 2180950 A1 | 8/1995 |
| CN | 1233256 A | 10/1999 |
| CN | 101928346 A | 12/2010 |
| CN | 103635489 A | 3/2014 |
| DE | 69533472 T2 | 1/2006 |
| EA | 2016/91470 A1 | 12/2016 |
| EA | 2017/92161 A1 | 4/2018 |
| EP | 0 132 732 A2 | 2/1985 |
| EP | 0 210 029 | 1/1987 |
| EP | 0 255 011 A2 | 2/1988 |
| EP | 0 274 826 | 7/1988 |
| EP | 0 285 123 A2 | 10/1988 |
| EP | 0 301 122 | 2/1989 |
| EP | 0 307 592 A2 | 3/1989 |
| EP | 0 318 451 | 5/1989 |
| EP | 0 401 508 A2 | 12/1990 |
| EP | 0 486 001 A1 | 5/1992 |
| EP | 0 621 870 B1 | 11/1994 |
| EP | 0 621 871 B1 | 11/1994 |
| EP | 0 739 355 B1 | 10/1996 |
| EP | 1 288 305 A2 | 3/2003 |
| EP | 1 484 339 A2 | 12/2004 |
| JP | 7504891 | 6/1995 |
| JP | H9-509838 | 10/1997 |
| JP | 9511131 | 11/1997 |
| JP | 10503375 | 3/1998 |
| JP | 2002-524076 A | 8/2002 |
| JP | 2006-501168 A | 1/2006 |
| JP | 2008-514624 | 5/2008 |
| JP | 2009-529553 A | 8/2009 |
| JP | 2013-516478 A | 5/2013 |
| JP | 2014-515763 A | 7/2014 |
| WO | WO 87/05396 A1 | 9/1987 |
| WO | WO 1989/010374 A1 | 11/1989 |
| WO | WO 1990/002809 | 3/1990 |
| WO | WO 1992/006111 A1 | 4/1992 |
| WO | WO 1993/009233 A2 | 5/1993 |
| WO | WO 1993/014120 A1 | 7/1993 |
| WO | WO 1993/014121 A1 | 7/1993 |
| WO | WO 1993/014122 A1 | 7/1993 |
| WO | WO 1995/018830 A2 | 7/1995 |
| WO | WO 1995/021601 A2 | 8/1995 |
| WO | WO 1995/023860 | 9/1995 |
| WO | WO 1996/004378 | 2/1996 |
| WO | WO 1996/020278 | 7/1996 |
| WO | WO 1996/035788 A2 | 11/1996 |
| WO | WO 1997/033996 | 9/1997 |
| WO | WO 1998/052976 A1 | 11/1998 |
| WO | WO 1999/063090 A2 | 12/1999 |
| WO | WO 2000/014235 A1 | 3/2000 |
| WO | WO 2000/034317 A2 | 6/2000 |
| WO | WO 2001/009968 | 2/2001 |
| WO | WO 2001/014424 A2 | 3/2001 |
| WO | WO 2001/068707 | 9/2001 |
| WO | WO 2001/079480 A1 | 10/2001 |
| WO | WO 2002/006334 | 1/2002 |
| WO | WO 2002/006539 | 1/2002 |
| WO | WO 2002/092147 | 11/2002 |
| WO | WO 2002/094200 | 11/2002 |
| WO | WO 2003/066824 A2 | 8/2003 |
| WO | WO 2003/103475 A2 | 12/2003 |
| WO | WO 2004/019968 A1 | 3/2004 |

(56) References Cited

FOREIGN PATENT DOCUMENTS

| WO | WO 2004/062646 A1 | 7/2004 |
|---|---|---|
| WO | WO 2004/062689 A1 | 7/2004 |
| WO | WO 2005/021556 | 3/2005 |
| WO | WO 2005/021557 A2 | 3/2005 |
| WO | WO 2005/075665 | 8/2005 |
| WO | WO 2006/017538 | 2/2006 |
| WO | WO 2006/036860 A2 | 4/2006 |
| WO | WO 2006/066878 A1 | 6/2006 |
| WO | WO 2006/089005 A2 | 8/2006 |
| WO | WO 2007/079096 A2 | 7/2007 |
| WO | WO 2007/104541 A2 | 9/2007 |
| WO | WO 2007/106746 | 9/2007 |
| WO | WO 2008/000833 | 1/2008 |
| WO | WO 2009/026334 A2 | 2/2009 |
| WO | WO 2009/026539 A1 | 2/2009 |
| WO | WO 2009/102927 A1 | 8/2009 |
| WO | WO 2010/003475 | 1/2010 |
| WO | WO 2010/006746 | 1/2010 |
| WO | WO 2010/080833 | 7/2010 |
| WO | WO 2011/085103 | 7/2011 |
| WO | WO 2012/094587 | 7/2012 |
| WO | WO 2013/186700 A1 | 12/2013 |
| WO | WO 2014/152232 * | 3/2014 |
| WO | WO 2014/113701 A1 | 7/2014 |
| WO | WO 2014/113712 A1 | 7/2014 |
| WO | WO 2014/152232 A2 | 9/2014 |
| WO | WO 2015/112578 A1 | 7/2015 |
| WO | WO 2016/160926 A1 | 10/2016 |

OTHER PUBLICATIONS

[No Author Listed] Efficacy and Safety Study of DX-2930 to prevent acute angioedema attacks in patients with Type I and Type II HAE. Study NCT02586805. ClinicalTrials.gov Apr. 9, 2019. 7pgs.

[No Author Listed] Fair Disclosure Wire, "Dyax Corp. announces positive results from phase 1a clinical trial of DX2930" dated Feb. 25, 2014. Last accessed from http://dialog.proquest.com/professional/printviewfile?accountid=157282 on May 20, 2016. p. 1-15.

Abdel-Salam et al., "Expression of mouse anticreatine kinase (MAK33) monoclonal antibody in the yeast *Hansenula polymorpha*", Appl. Microbiol. Biotechnol, vol. 56, p. 157-164 (2001).

Abuchowski et al., "Alteration of immunological properties of bovine serum albumin by covalent attachment of polyethylene glycol," J. Bio. Chem., 1977, vol. 252, pp. 3578-3581.

Abuchowski et al., "Cancer therapy with chemically modified enzymes, I., Antitumor properties of polyethylene glycol-asparaginase conjugates," Cancer Biochem. Biophys., 1984, vol. 7, pp. 175-186.

Abuchowski et al., "Effect of covalent attachment of polyethylene glycol on immunogenicity and circulating life of bovine," J. Biol. Chem., 1977, vol. 252, pp. 3582-3586.

Adams et al: "The role of viscosupplementation with hylan G-F 20 (Synvisc(R)) in the treatment of osteoarthritis of the knee: a Canadian multicenter trial comparing hylan G-F 20 alone, hylan G-F 20 with non-steroidal anti-inflammatory drugs (NSAIDs)and NSAIDs alone", Osteoarthritis and Cartilage, Bailliere Tindall, London, GB, vol. 3, No. 4, pp. 213-225, (Dec. 1, 1995).

Adelman et al., Proteolysis of Platelet Glycoprotein 1b by Plasmin Is Facilitated by Plasmin Lysine-Binding Regions, Blood, vol. 68 (6): 1280-1284, (Dec. 1986).

Albrecht et al., Elastase inhibition by the inter-alpha-trypsin inhibitor and derived inhibitors of man and cattle. Hoppe Seylers Z Physiol Chem. Dec. 1983;364(12): 1703-8.

Albrecht et al., Kunitz-type proteinase inhibitors derived by limited proteolysis of the inter-alpha-trypsin inhibitor, IX. Isolation and characterization of the inhibitory parts of inter-alpha-trypsin inhibitors from several mammalian sera. Hoppe Seylers Z Physiol Chem. Dec. 1983;364(12):1697-702.

Altschul et al. "Gapped BLAST and PSI-BLAST: a new generation of protein database search programs." (1997) Nucleic Acids Res. 25:3389-3402.

Anba et al., Improving the Stability of a Foreign Protein in the Periplasmic Space of *Escherichia coli*, Biochimie, vol. 70(6): 727-733, (1988).

Angliker et al., The Synthesis of Lysylflouromethanes and their Properties as Inhibitors of Trypsin, Plasmin and Cathepsin B, Biochemistry, 241:871-875, (1987).

Asano et al., "Effects of a nonpeptide bradykinin B2 receptor antagonist, FR167344, on different in vivo animal models of inflammation", Br J Pharmacol, vol. 122, p. 1436-1440 (1997).

Asano M et al., Br J Pharmacol, vol. 122, p. 1436-1440 (1997).

Atherton et al., Peptide Synthesis. Part 2. Procedures for Solid Phase Synthesis using Nα-Fluorenylmethycarbonylamino-acids on Polyamide Supports. Synthesis of Substance P and of Acyl Carrier Protein 65-74 Decapeptide, J. Chem. Soc. Perkins Trans, 1:538-546, (1981).

Attwood, The Babel of Bioinformatics; Science, vol. 290, pp. 471-473 (2000).

Auerswald et al., Expression, Isolation and Characterization of Recombinant [Arg15, Glu52] Aprotinin, Bio. Chem. Hoppe-Seyler, 369:(Suppl)27-35 (1988).

Baba et al., States of Tyrosyl Residues and Circular Dichroism of Kunitz Trypsin Inhibitor, J. Biochem 65 (1):113-121 (1969).

Bagdasarian et al., Immunochemical studies of plasma kallikrein. J Clin Invest. Dec. 1974;54(6):1444-54.

Balduyck et al., Human Urinary Proteinase Inhibitor: Inhibitory Properties and Interaction with Bovine Trypsin, Bio. Chem. Hoppe-Seyler, vol. 366: 9-14, (1985).

Banerji et al., Effect of Lanadelumab Compared With Placebo on Prevention of Hereditary Angioedema Attacks: A Randomized Clinical Trial. JAMA. Nov. 27, 2018;320(20):2108-2121. doi: 10.1001/jama.2018.16773.

Banerji et al., Inhibiting Plasma Kallikrein for Hereditary Angioedema Prophylaxis. N Engl J Med. Feb. 23, 2017;376(8):717-728. doi: 10.1056/NEJMoa1605767.

Baneyx et al., "In Vivo Degradation of Secreted Fusion Proteins by the *Escherichia coli* Outer Membrane Protease OmpT", J. Bacteriol., 172:491-494, (1990).

Baneyx et al., Construction and Characterization of *Escherichia coli* Strains Deficient in Multiple Secreted Proteases: Protease III Degrades High-Molecular-Weight Substrates In Vivo, J Bacteriol., 173:2696-2703 (1991).

Basu et al., "Structure-function engineering of interferon-b-1b for improving stability, solubility, potency, immunogenicity, and pharmacokinetic properties by site-selective mono-PEGylation," Bioconjugate Chemistry, 2006, vol. 17, pp. 618-630.

Baumann, "A multi-level study of recombinant Pichia pastoris in different oxygen conditions", BMC Syst Biol. 4:141 (Oct. 22, 2010).

Bayes et al., "Gateways to Clinical Trials" Methods Find Exp. Clin. Pharmacol., vol. 28(3): pp. 185-206 (2006).

Beckmann et al., "Preparation of chemically 'mutated' aprotinin homologues by semisynthesis-P1 substitutions change inhibitory specificity," Eur. J. Biochem., vol. 176, pp. 675-682 (1988).

Beech et al., "Further characterisation of a thromboembolic model of stroke in the rat" Brain Res, vol. 895, p. 18-24 (2001).

Bendig, Humanization of Rodent Monoclonal Antibodies by CDR Grafting. Companion to Methods in Enzymology. 1995; 8:83-93.

Berge et al., "Pharmaceutical salts", J. Pharm. Sci. 66:1-19 (1977).

Bergthorsdottir et al., "Signals that initiate somatic hypermutation of B cell in vitro", J. Immunol., p. 166:2228 (2001).

Berndt et al., "Designed Replacement of an Internal Hydration Water Molecule in BPTI: Structural and Functional Implications of a Glycine-to-Serine Mutation," Biochemistry, 32: 4564-4570 (1993).

Bhoola et al., "Bioregulation of Kinins: Kallikreins, Kininogens and Kininases," Pharmacological Reviews, 44 :1-80 (1992).

Bird et al. "Single chain antigen binding proteins", Science 242:423-426 (1988).

Blaber et al., "Targeting kallikrein 6-proteolysis attenuates CNS inflammatory disease," FASEB J. May 2004;18(7):920-2. Epub Mar. 19, 2004.

Blijlevens et al., Palifermin (recombinant keratinocyte growth factor-1): a pleiotropic growth factor with multiple biological activities in preventing chemotherapy- and radiotherapy-induced mucositis. Ann Oncol. May 2007;18(5):817-26. Epub Oct. 9, 2006.

(56) References Cited

OTHER PUBLICATIONS

Bodanszky et al., The Practice of Peptide Synthesis (Springer-Verlag, New York, 1984).
Bork, "Powers and pitfalls in sequence analysis: the 70% hurdle," Genome Research, vol. 10, pp. 398-400 (2000).
Borregaard et al., "Granules of the human neutrophilic polymorphonuclear leukocyte," Blood, 1997, vol. 89, No. 10, pp. 3503-3521.
Bova et al., Lanadelumab Injection Treatment For The Prevention Of Hereditary Angioedema (HAE): Design, Development And Place In Therapy. Drug Des Devel Ther. Oct. 22, 2019;13: 3635-3646. doi: 10.2147/DDDT.S192475.
Bowdish et al., "Yeast expression of a catalytic antibody with chorismate mutase activity.", J Biol Chem.; 266 (18):11901-8 (Jun. 25, 1991).
Bowie et al. "Deciphering the message in protein sequences: tolerance to amino acid substitutions." Science 247:1306-1310 (1990).
Branden et al., "Prediction, Engineering, and Design of Protein," Introduction to Protein Structure, 1991, pp. 247, Garland Publishing Inc., New York.
Breedveld, Therapeutic monoclonal antibodies. Lancet. Feb. 26, 2000;355(9205):735-40. Review.
Brenner, "Errors in genome annotation," Trends in Genetics, vol. 15, No. 4, pp. 132-133 (1999).
Brinkmann et al., "Design of an aprotinin variant with inhibitory activity against chymotrypsin and cathepsin G by recombinant DNA technology," Biol. Chem. Hoppe-Seyler, vol. 371, pp. 43-52 (1990).
Browne et al., "Expression of Recombinant Human Plasminogen and Aglycoplasminogen in HeLa Cells," Genebank, Accession No. M74220 (1991).
Broze et al., "Regulation of Coagulation by a Multivalent Kunitz-Type Inhibitor," Biochemistry, 29:7539-7546, (1990).
Brus et al., "Disease Severity Is Correlated with Plasma Clotting and Fibrinolytic and Kinin-Kallikrein Activity in Neonatal Respiratory Distress Syndrome," Pediatric Research, 41:120-127, (1997).
Buchan et al., "A new model of temporary focal neocortical ischemia in the rat", Stroke 23(2): 273-9 (1992).
Budavari, ed., Merck index, 11th ed., ISBN 911910-28-X, entries 923, 1745, 2740, 7425, (1989).
Buras et al., "Animal models of sepsis: setting the stage", Nat Rev Drug Discov. 4(10):854-65 (2005).
Burrage et al., "Matrix metalloproteinases: role in arthritis," Frontiers in Bioscience, 2006, vol. 11, pp. 529-543.
Burton et al. "Human Antibody Effector Function", Adv. Immunol. 51:1-84 (1992).
Busse et al., Efficacy and safety of lanadelumab for prophylactic treatment in adolescents with hereditary angioedema (HAE). Feb. 2019;143(2): AB43.
Cantor et al., "Elastin and Elastases in Lung Disease", Elastin and Elastases, Chapter 16, vol. II, pp. 159-168 (1989).
Carey et al., Advanced Organic Chemistry, 3rd Edition, Part B: Reactions and Synthesis, Plenum Press, New York: 678-686 (1990).
Carmichael, "Rodent models of focal stroke: size, mechanism, and purpose", NeuroRx 2: 396-409 (2005).
Carpenter et al., "Rational design of stable lyophilized protein formulations: theory and practice," Pharmaceutical Biotechnology, vol. 13, pp. 109-133 (2002).
Casati et al., Tranexamic acid compared with high-dose aprotinin in primary elective heart operations: effects on perioperative bleeding and allogeneic transfusions. J Thorac Cardiovasc Surg. Sep. 2000;120(3):520-7.
Casset et al., A peptide mimetic of an anti-CD4 monoclonal antibody by rational design. Biochem Biophys Res Commun. Jul. 18, 2003;307(1):198-205.
Cassim et al., "Kallikrein cascade and cytokines in inflamed joints," Pharmacology and Therapeutics, 2002, vol. 94, pp. 1-34.
Cernak, "Animal models of head trauma", NeuroRx. 2(3):410-422 (2005).
Chen et al., "A model of focal ischemic stroke in the rat: reproducible extensive cortical infarction", Stroke 17 (4): 738-43 (1986).
Chen et al., "Establishment of an animal model of oral mucositis induced by conditioning regimen of haematopoietic stem cell transplantation" Zhonghua Kou Qiang Yi Xue Za Zhi. 42(11):672-6 (2007). (Abstract only).
Chen et al., "Refined 2-5 A X-ray Crystal Structure of the Complex Formed by Porcine Kallikrein A and the Bovine Pancreatic Trypsin Inhibitor—Crystallization, Patterson Search, Structure Determination, Refinement, Structure and Comparison with its Components and with the Bovine Trypsin-Pancreatic Trypsin Inhibitor Complex" J. Mol. Biol., 164:283-311 (1983).
Chen et al., Selection and analysis of an optimized anti-VEGF antibody: crystal structure of an affinity-matured Fab in complex with antigen. J Mol Biol. Nov. 5, 1999;293(4):865-81.
Chen et al., Solution Structure of a Kunitz-type Chymotrypsin Inhibitor Isolated from the Elapid Snake Bungarus Fasciatus, J. Biological Chemistry 276:45079-45087 (2001).
Chothia et al. "Canonical structures for the hypervariable regions of immunoglobulins." (1987) J. Mol. Biol. 196:901-917 (1987).
Chothia et al. "Structural Repertoire of the Human VH Segments", J. Mol. Biol. 227:799-817 (1992).
Chung et al., "Human plasma prekallikrein, a zymogen to a serine protease that contains four tandem repeats," GenBank, Accession #P03952 (1986).
Churg et al., "Proteases and emphysema," Curr. Opin. Pulm. Med., 2005, vol. 11, pp. 153-159.
Chyung et al., A phase 1 study investigating DX-2930 in healthy subjects. Ann Allergy Asthma Immunol. Oct. 2014;113(4):460-6.e2. doi: 10.1016/j.anai.2014.05.028. Epub Jun. 26, 2014.
Colman et al., "Contact System: A Vascular Biology Modulator With Anticoagulant, Profibrinolytic, Antiadhesive, and Proinflammatory Attributes" Blood, 90, 3819-3843 (1997).
Colman et al., "The Plasma Kallikrein-Kinin System in Sepsis, Inflammatory Arthritis, and Enterocolitis" Clinical Reviews in Allergy and Immunology, vol. 16, pp. 365-384 (1998).
Colman et al., Hemostasis and Thrombosis Basic Principles and Clinical Practice, Chapter 1, 2nd Edition, 3-17 (1987).
Colman R. W., "Plasma and tissue Kallikrein in Arthritis and Inflammatory Bowel Disease", Immunopharmacology, Jan. 1, 1999, pp. 103-108, vol. 43, No. 2/03, Elsevier Science Publishers, BV.
Colman RW et al., "Activation of the kallikrein-kinin system in arthritis and enterocolitis in genetically susceptible rats: modulation by a selective plasma kallikrein inhibitor", Proceedings of the Association of American Physicians, Jan. 1, 1997, pp. 10-22, vol. 109, No. 1, Cambridge, MA US.
Cook et al., The human immunoglobulin VH repertoire. Immunol Today. May 1995;16(5):237-42.
Corpet, et al. "Recent improvements of the ProDom database of protein domain families" Nucl. Acids Res. 27:263-267 (1999).
Cumming et al., "Hemodynamic, Renal, and Hormonal Aprotinin in an Ovine Model of Septic Shock," Critical Care Medicine, 20:1134-1139 (1992).
Cunningham et al., "Structural and functional characterization of tissue factor pathway inhibitor following degradation by matrix metalloproteinase-8," Biochem. J., 2002, vol. 367, pp. 451-458.
Current Protocols in Molecular Biology, John Wiley & Sons, N.Y. (1989) 6.3.1-6.3.6.
Currie et al., "Design and Synthesis of a Bicyclic Non-Peptide β-Bend Mimetic of Enkephalin," Tetrahedron, 49:3489-3500 (1993).
De Agostini et al., Human plasma kallikrein and C1 inhibitor form a complex possessing an epitope that is not detectable on the parent molecules: demonstration using a monoclonal antibody. Proc Natl Acad Sci U S A. Aug. 1985;82(15):5190-3.
De Campos et al., "Antioedematogenic and antinociceptive actions of NPC 18521, a novel bradykinin B2 receptor antagonist", Eur J Pharmacol. 316, 277-286 (1996).
De Haard et al. "A large non-immunized human Fab fragment phage library that permits rapid isolation and kinetic analysis of high affinity antibodies". J. Biol. Chem 274:18218-30, (1999).
De Pascalis et al., Grafting of "abbreviated" complementarity-determining regions containing specificity-determining residues essen-

(56) References Cited

OTHER PUBLICATIONS tial for ligand contact to engineer a less immunogenic humanized monoclonal antibody. J Immunol. Sep. 15, 2002;169(6):3076-84.

De Wildt et al. "Antibody arrays for high-throughput screening of antibody-antigen interactions", Nat. Biotechnol. 18:989-994 (2000).

De Wildt et al., "Characterization of human variable domain antibody fragments against the U1 RNA-associated A protein, selected from a synthetic and patient-derived combinatorial V gene library" Eur J Immunol. 26(3):629-39 (1996).

Debiopharm brochure, "Engineering protein inhibitor of human neutrophil elastase EPIO-hNE4 (DX-890)," Dated Oct. 2004, printed from www.debio.com/e/pdf/fiche.sub.--epi.sub.--hne4.sub.--e.pdf.

Dela Cadena et al., "Role of Kallikrein-Kinin System in the Pathogenesis of Bacterial Cell Wall-Induced Inflammation and Enterocolitis," Transact. Assoc. Am. Physicians, 105:229-237 (1992).

Dela Cadena, et al., "Inhibition of Plasma Kallikrein Prevents Peptidoglycan-Induced Arthritis in the Lewis Rat," FASEB Journal, 9:446-452 (1995).

Delacourt et al., "Protection against acute lung injury by intravenous or intratracheal pretreatment with EPI-HNE-4, a new potent neutrophil elastase inhibitor," Am. J. Respir. Cell Mol. Biol., Mar. 26, 2002, vol. 26, No. 3, pp. 290-297.

Delaria et al., "Characterization of placental bikunin, a novel human serine protease inhibitor," J. Biological Chemistry, May 2, 1997, vol. 272, No. 18, pp. 12209-12214.

Delgado et al., "The uses and properties of PEG-linked proteins," Critical Review in Therapeutic Drug Carrier Systems, 1992, vol. 9, No. 3,4, pp. 249-304.

Deng et. al., "Production of recombinant humanized anti-HBsAg Fab antibody by fermentation" Sheng Wu Gong Cheng Xue Bao, 20(5):800-4 (Sep. 2004) (Abstact Only).

Dennis et al., "Kunitz Domain Inhibitors of Tissue Factor-Factor VIIa (I. Potent Inhibitors Selected from Libraries by Phage Display)," Journal of Biological Chemistry 269:22129-22136 (1994).

Dennis et al., "Kunitz Domain Inhibitors of Tissue Factor-Factor VIIa (II. Potent and Specific Inhibitors by Competitive Phage Selection)," Journal of Biological Chemistry, 269:22137-22144 (1994).

Dennis et al., "Potent and Selective Kunitz Domain Inhibitors of Plasma Kallikrein Designed by Phage Display," J. Biol. Chem., 270:25411-25417 (1995).

Devani et al., "Kallikrein-kinin system in inflammatory bowel disease: intestinal involvement and correlation with the degree of tissue inflammation," Digestive and Liver Disease, 2005, vol. 37, pp. 665-673.

Dhalluin et al., "Structural, kinetic, and thermodynamic analysis of the binding of the 40kDa PEG-interferon-a-2a and its individual positional isomers to the extracellular domain of the receptor IFNAR2," Bioconjugate Chemistry, 2005, vol. 16, pp. 518-527.

Diaz et al., "The Design of Water Soluble β-Sheet Structure Based on a Nucleation Strategy," Tetrahedron, 49:3533-3545 (1993).

Dimaio et al., "A New Class of Potent Thrombin Inhibitors That Incorporates a Scissile Pseudopeptide Bond," FEBS Lett, 282(1):47-52 (1991).

Dittmar et al., "External carotid artery territory ischemia impairs outcome in the endovascular filament model of middle cerebral artery occlusion in rats" Stroke 34: 2252-7 (2003).

Dittmar et al., "Fischer-344 rats are unsuitable for the MCAO filament model due to their cerebrovascular anatomy" J Neurosci Methods 156: 50 (2006).

Doerks et al., "Protein annotation: detective work for function prediction," Trends in Genetics, vol. 14, No. 6, pp. 248-250 (1998).

Donnelly et al., "Therapy for chronic obstructive pulmonary disease in the 21st century," Drugs, 2003, vol. 63, pp. 1973-1998.

Dragosits et. al., "The effect of temperature on the proteome of recombinant *Pichia pastoris*", J Proteome Res. Mar. 2009;8(3):1380-92. 16 pages.

Dragosits et. al., "The response to unfolded protein is involved in osmotolerance of *Pichia pastoris*" BMC Genomics. Mar. 26, 2010;11:207.

Druar et. al., Analysis of the expressed heavy chain variable-region genes of Macaca fascicularis and isolation of monoclonal antibodies specific for the Ebola virus' soluble glycoprotein Immunogenetics, 57(10):730-8 (2005).

Dufton, "Protein inhibitors and dendrotoxins," Eur. J. Biochem., vol. 153, pp. 647-654. (1985).
Edqvist, et al., "Production of functional IgM Fab fragments by *Saccharomyces cerevisiae*", J Biotechnol 20 (3):291-300 (1991).
Eigenbrot et al., "Structural Effects Induced by Removal of a Disulfide-Bridge: The X-ray Structure of the C30A/C51A Mutant of Basic Pancreatic Trypsin Inhibitor at 1.6 A," Protein Engineering, 3:591-598 (1990).
Ellis et al., "The Urokinase Receptor: Involvement in Cell Surface Proteolysis and Cancer Invasion," Ann. NY. Acad. Sci., 667:13-31 (1992).
Enzon Pharmaceuticals, Macromolecular Engineering Technologies, 2004, pp. 1-14.
Falquet et al., "The PROSITE database, its status in 2002." (2002) Nucleic Acids Res. 30:235-238.
Feener, Plasma kallikrein and diabetic macular edema. Curr Diab Rep. Aug. 2010;10(4):270-5. doi: 10.1007/s11892-010-0127-1.
Ferrara et al., Recombinant renewable polyclonal antibodies. MAbs. 2015;7(1):32-41. doi: 10.4161/19420862.2015.989047.
Fidler et al., "The Implications of Angiogenesis for the Biology and Chemistry of Cancer Metastasis," Cell, 79:185-188 (1994).
Fields et al., "Solid Phase Peptide Synthesis Utilizing 9-fluorenylmethocarbonyl Amino Acids," Int. J. Peptide Protein Research, 35:161-214 (1990).
Fife et al., "Cartilage matrix glycoprotein is present in serum in experimental canine osteoarthritis" J Clin Invest. 84(5):1432-1439 (1989).
Fink et al., Cellular expression of plasma prekallikrein in human tissues. Biol Chem. Sep. 2007;388(9):957-63.
Fraedrich et al., "Reduction of Blood Transfusion requirement in Open Heart Surgery by Administration of High Doses of Aprotinin-Preliminary Results," Thorac Cardiovasc Surgeon, 37:89-91 (1989).
Frank, 8. Hereditary angioedema. J Allergy Clin Immunol. Feb. 2008;121(2 Suppl): S398-401; quiz S419. doi: 10.1016/j.jaci.2007.07.057.
Fredrich et al., "A new animal model of venous thrombosis in rats with low flow conditions in the venous blood stream" Blood Coagul Fibrinolysis. 5(2):243-8 (1994).
Freidinger et al., "Protected Lactam-Bridged Dipeptides for Use as Conformational Constraints in Peptides," Journal of Organic Chemistry, 47:104-109 (1982).
Fries et al., "Inter-a-inhibitor, hyaluronan and inflammation," Acta Biochimica Polonica, 2003, vol. 50, No. 3, pp. 735-742.
Frisbie, "An animal model for venous thrombosis and spontaneous pulmonary embolism." Spinal Cord 43, 635-639 (2005).
Galeffi et al., "Functional expression of a single-chain antibody to ErbB-2 in plants and cell-free systems" J Transl Med. Sep. 29, 2006;4:39. 13 pages.
Gao et al., Extracellular carbonic anhydrase mediates hemorrhagic retinal and cerebral vascular permeability through prekallikrein activation. Nat Med. Feb. 2007;13(2):181-8. Epub Jan. 28, 2007.
Gardell et al., "The Search for the Ideal Thrombolytic Agent: Maximize the Benefit and Minimize the Risk," Toxicologic Pathology, 21(2): 190-198 (1993).
Gasser et al., "Engineering of *Pichia pastoris* for improved production of antibody fragments" Biotechnol Bioeng. Jun. 5, 2006;94(2):353-61.
GenBank Submission; NIH/NCBI, Accession No. NM_008455.2 (GI: 236465804): "Plasma kallikrein precursor", GenBank Record created on Dec. 29, 2010.
GenBank Submission; NIH/NCBI, Accession No. NM_012725.2 (GI:162138904): "Plasma kallikrein precursor", GenBank Record created on Dec. 26, 2010.
GenBank Submission; NIH/NCBI, Accession No. NP_000418.2 (GI:109255251): "loricrin", GenBank Record created on Nov. 3, 2010.
GenBank Submission; NIH/NCBI, Accession No. NP _000883.2 (GI: 78191798): "Plasma kallikrein preproprotein", GenBank Record created on Nov. 21, 2010.

(56) References Cited

OTHER PUBLICATIONS

GenBank Submission; NIH/NCBI, Accession No. NP_000892 (GI: 158508572): "mineralocorticoid receptor isoform 1", GenBank Record created on Dec. 27, 2010.
GenBank Submission; NIH/NCBI, Accession No. NP_005850.1 (GI:5032007): "transcriptional activator protein Pur-alpha", GenBank Record created on Dec. 28, 2010.
GenBank Submission; NIH/NCBI, Accession No. NP_006228.3 (GI:110347449): "POU domain, class 4, transcription factor 1", GenBank Record created on Dec. 27, 2010.
GenBank Submission; NIH/NCBI, Accession No. NP_009060.2 (GI:22547197): "zinc finger protein ZIC 2", GenBank Record created on Dec. 24, 2010.
GenBank Submission; NIH/NCBI, Accession No. NP_031393.2 (GI:21396480): "RNA-binding protein Raly isoform 2", GenBank Record created on Dec. 25, 2010.
GenBank Submission; NIH/NCBI, Accession No. NP_032481.2 (GI: 236465805): "Plasma kallikrein precursor", GenBank Record created on Dec. 29, 2010.
GenBank Submission; NIH/NCBI, Accession No. NP_036857.2 (GI:162138905): "Plasma kallikrein precursor", GenBank Record created on Dec. 26, 2010.
GenBank Submission; NIH/NCBI, Accession No. NP_056932.2 (GI:153791670): "Plasma kallikrein preproprotein", GenBank Record created on Dec. 27, 2010.
GenBank Submission; NIH/NCBI, Accession No. NP_061856.1 (GI:9506713): "H/ACA ribonucleoprotein complex subunit 1", GenBank Record created on Dec. 24, 2010.
GenBank Submission; NIH/NCBI, Accession No. NP_065104.1 (GI:9966841): "cell death regulator Aven", GenBank Record created on Dec. 26, 2010.
GenBank Submission; NIH/NCBI, Accession No. NP_115818.2 (GI:53829370): "neuralized-like protein 4 isoform 1", GenBank Record created on Dec. 27, 2010.
GenBank Submission; NIH/NCBI, Accession No. NP_476429.2 (GI:109148552): "keratin, type II cytoskeletal 3", GenBank Record created on Dec. 24, 2010.
GenBank Submission; NIH/NCBI, Accession No. NP_631961.1 (GI:21327701): "TATA-binding protein-associated factor 2N isoform 1", GenBank Record created on Dec. 25, 2010.
GenBank Submission; NIH/NCBI, Accession No. NP_787059.2 (GI:40068462): "At-rich interactive domain-containing protein 1B isoform 3", GenBank Record created on Mar. 4, 2010.
GenBank Submission; NIH/NCBI, Accession No. XP_376532.2 (GI:51465288): "Predicted: KIAA0408", GenBank Record created on Aug. 19, 2004.
Gerriets et al., "Complications and pitfalls in rat stroke models for middle cerebral artery occlusion: a comparison between the suture and the macrosphere model using magnetic resonance angiography", Stroke 35: 2372-2377 (2004).
Gerriets et al., "The macrosphere model: evaluation of a new stroke model for permanent middle cerebral artery occlusion in rats" J Neurosci Methods 122: 201-11 (2003).
Girard et al., "Functional Significance of the Kunitz-type Inhibitory Domains of Lipoprotein-Associated Coagulation Inhibitor," Nature, 338:518-520 (1989).
Girard et al., "Structure of the Human Lipoprotein-associated Coagulation Inhibitor Gene," The Journal of Biological Chemistry, 266:5036-5041 (1991).
Goldenberg et al., "Circular and circularly permuted forms of bovine pancreatic trypsin inhibitor," J. Mol. Biol., vol. 165, pp. 407-413 (1983).
Gomez-Jorge et al., "The Double-Tuck Model: A New Animal Model of Arterial Thrombosis" J. Vasco Inter. Rad. 9 (4): 633-638 (1998).
Gonzalez-Quevedo et al., The Synthetic Kunitz Domain Protein DX88 to Treat Angioedema in Patients with Hereditary Angioedema, International Immunopharmacology 2(9):1318 Abstract 205 (2002).
Goodson et al., "Site-directed PEGylation of recombinant interleukin-2 at its glycosylation site," Bio Technology, 1990, vol. 8, pp. 343-346.
Gouzy et al. "Whole genome protein domain analysis using a new method for domain clustering" (1999) Computers and Chemistry 23:333-340.
Graham et al., "Animal models of ischemic stroke: balancing experimental aims and animal care", Comp Med 54: 486-496 (2004).
Green, Antibody engineering via genetic engineering of the mouse: XenoMouse strains are a vehicle for the facile generation of therapeutic human monoclonal antibodies. J Immunol Methods. Dec. 10, 1999;231(1-2):11-23.
Greilich et al., "Antifibrinolytic therapy during cardiopulmonary bypass reduces proinflammatory cytokine levels: a randomized, double-blind, placebo-controlled study of ε-aminocaproic acid and aprotinin," J. Thorac. Cardiovasc. Surg., 2003, vol. 126, pp. 1498-1503.
Gribskov et al. "Profile analysis." (1990) Meth. Enzymol. 183:146-159.
Gribskov et al. "Profile analysis: detection of distantly related proteins." (1987) Proc. Natl. Acad. Sci. USA 84:4355-4358.
Grimaldi et al., "Trasylol in the treatment of acute arthritis due to microcrystals," Reumatismo, vol. 23, No. 5, pp. 217-221, (1971) (Abstract only).
Gullberg et al., "Biosynthesis, processing and sorting of neutrophil proteins: insight into neutrophil granule development," Eur. Journal of Haematology, 1997, vol. 58, pp. 137-153.
Guzman et al. "Mono-iodoacetate-induced histologic changes in subchondral bone and articular cartilage of rat femorotibial joints: an animal model of osteoarthritis." Toxicol Pathol. 31(6):619-24 (2003).
Hagihara et al., "Screening for stable mutants with amino acid pairs substituted for the disulfide bond between residues 14 and 38 of bovine pancreatic trypsin inhibitor (BPTI)," The Journal of Biological Chemistry, 2002, vol. 277, No. 52, pp. 51043-51048.
Han et al., Increased Vascular Permeability in C1 Inhibitor-Deficient Mice Mediated by the Bradykinin Type 2 Receptor, J. Clinical Investigation 109(8):1057-1063 (2002).
Han, Reversal of the Increased Vascular Permeability in C1 Inhibitor Deficient Mice: Therapeutic Approaches, International Immunopharmacology 2(9):1315 Abstract 176 (2002).
Hanes et al., "Picomolar affinity antibodies from a fully synthetic naive library selected and evolved by ribosome display" Nat Biotechnol. 18:1287-92 (2000).
Hanes et al., "Selecting and evolving functional proteins in vitro by ribosome display" Methods Enzymol. 328:404-30 (2000).
Harvey et al., "Engineering of recombinant antibody fragments to methamphetamine by anchored periplasmic expression" J Immunol Methods. Jan. 20, 2006;308(1-2):43-52. Epub Nov. 22, 2005.
Herter et al., "Hepatocyte growth factor is a preferred in vitro substrate for the human hepsin, a membrane-anchored serine protease implicated in prostate and ovarian cancers," Biochem. J., 2005, vol. 390, pp. 125-136.
Hoet et al., "Generation of high-affinity human antibodies by combining donor-derived and synthetic complementarity-determining-region diversity" Nat Biotechnol. 23(3)344-8 (2005).
Hoogenboom et al., "Antibody phage display technology and its applications" Immunotechnology 4:1-20 (1998).
Hoogenboom et al., "Natural and designer binding sites made by phage display technology" Immunol Today 2:371-8 (2000).
Hoover et al., "Amino Acids of the Recombinant Kringle 1 Domain of Human Plasminogen that Stabilize Its Interaction w-Amino Acids," Biochemistry, 32:10936-10943 (1993).
Hortin et al., "Allosteric Changes in Thrombin's Activity Produced by peptides Corresponding to Segments of Natural Inhibitors and Substrates," The Journal of Biological Chemistry, 266:6866-6871 (1991).
Horwitz et al., "Secretion of functional antibody and Fab fragment from yeast cells.", Proc Natl Acad Sci U S A. 85 (22):8678-82 (Nov. 1988).
Hostomsky et al., "Solid Phase Assembly of Cow Colostrum Trypsin Inhibitor Gene," Nucleic Acids Research, 15:4849-4856 (1987).

(56) References Cited

OTHER PUBLICATIONS

Huang et al., "Kinetics of factor Xa inhibition by tissue factor pathway inhibitor," The Journal of Biological Chemistry, 1993, vol. 268, No. 36, pp. 26950-26955.

Huang et al., "Novel peptide inhibitors of angiotensin-converting enzyme 2," The Journal of Biological Chemistry, 2003, vol. 278, No. 18, pp. 15532-15540.

Huge et al., "A model to investigate postoperative ileus with strain gauge transducers in awake rats" J Surg Res. 74 (2):112-8 (1998). (Abstact Only).

Huston et al., "Protein engineering of antibody binding sites: Recovery of specific activity in anti-digoxin single-chain Fv analogue produced in *Escherichia coli*", Proc. Natl. Acad. Sci. USA 85:5879-5883 (1988).

Hynes et al., X-ray crystal structure of the protease inhibitor domain of Alzheimer's amyloid beta-protein precursor. Biochemistry, 29:10018-10022 (1990).

Jefferis et al., "IgG-Fc-mediated effector functions: Molecular definition of interaction site for effector ligands and the role of glycosylation", Immunol. Rev. 163:59-76, (1998).

Jones et al., "Severe prekallikrein deficiency associated with homozygosity for an Arg94Stop nonsense mutation" Br J Haematol, 2004. 127(2): p. 220-3.

Jonkam et al., "Effects of the bradykinin B2 receptor antagonist icatibant on microvascular permeability after thermal injury in sheep" Shock, 28:704-709 (2007).

Jorg et al., Kinetic analysis of plasminogen activation by purified plasma kallikrein. Thromb Res. Aug. 1, 1985;39(3):323-31.

Jostock et al., "Rapid generation of functional human IgG antibodies derived from Fab-on-phage display libraries" J. Immunol. Methods, 289(1-2):65-80 (2004).

Kabat et al. Sequences of Proteins of Immunological Interest, Fifth Edition, U.S. Dept. of Health and Human Services, NIH Publication No. 91-3242 (1991).

Kantor et al., "The experimental animal models for assessing treatment of restenosis" Cardiovasc Radiat Med. 1 (1):48-54 (1999).

Kaplan et al., A prealbumin activator of prekallikrein. 3. Appearance of chemotactic activity for human neutrophils by the conversion of human prekallikrein to kallikrein. J Exp Med. Jan. 1972;135(1):81-97.

Katre et al., "Chemical modification of recombinant interleukin 2 by polyethylene glycol increases its potency in the murine Meth A sarcoma model," PNAS USA, 1987, vol. 84, pp. 1487-1491.

Katre et al., "Immunogenicity of recombinant IL-2 modified by covalent attachment of polyethylene glycol," J. Immunol., 1990, vol. 144, pp. 209-213.

Katz et al., "Animal models of vasculitides" Clin Rev Allergy Immunol. 35(1-2): 11-8 (2008).

Kaufman et al., "Amplification and expression of sequences cotransfected with a modular dihydrofolate reductase complementary dna gene", Mol. Biol. 159:601 621 (1982).

Kelly et al., "Diabetes insipidus in uricase-deficient mice: a model for evaluating therapy with poly(ethylene glycol)-modified," J. Am. Soc. Nephrol., 2001, vol. 12, pp. 1001-1009.

Kemp et al., "Synthesis of Peptide-Functionalized Daicylaminoepinodolidiones," Tetrahedron Letters, 29:5077-5080 (1988).

Kenniston et al., Discovery and Characterization Of a Highly Specific Antibody Inhibitor Of Plasma Kallikrein. Blood 2013; 122: 1067. Abstract only.

Kenniston et al., Inhibition of plasma kallikrein by a highly specific active site blocking antibody. J Biol Chem. Aug. 22, 2014;289(34):23596-608. doi: 10.1074/jbc.M114.569061. Epub Jun. 26, 2014.

Kettleborough et al., Humanization of a mouse monoclonal antibody by CDR-grafting: the importance of framework residues on loop conformation. Protein Eng. Oct. 1991;4(7):773-83.

Kido et al., "Kunitz-type Protease Found in Rat Mast Cells," J. Biol. Chem. 263(34): 18104-18107 (1988).

Kido et al., "Protease Specificity of Kunitz Inhibitor Domain of Alzheimer's Disease Amyloid Protein Precursor," Biochem Biophys Res Commun. Mar. 16, 1990;167(2):716-21.

Kirchhofer et al., "Hepsin activates pro-hepatocyte growth factor and is inhibited by hepatocyte growth factor activator-1B (HAI-1B) and HAI-2," FEBS Letters, 2005, vol. 579, pp. 1945-1950.

Kirchhoff et al., "A Major Human Epididymis-Specific cDNA Encodes a Protein with Sequence Homology to Extracellular Proteinase Inhibitors," Biology of Reproduction, 45:350-357 (1991).

Kline et al. "Hirulog Peptides with Scissile Bond Replacements Resistant to Thrombin Cleavage," Biochem. Biophys. Res. Comm., 177:1049-1055 (1991).

Knappik et al., "Fully synthetic human combinatorial antibody libraries (HuCAL) based on modular consensus frameworks and CDRs randomized with trinucleotides", J. Mol. Biol. 296:57-86 (2000).

Ko et al., "Biotransformation of uridine monophosphate (UMP) and glucose to uridine diphosphate-glucose (UDPG) by Candida saitoana KCTC7249 cells." Appl Biochem Biotechnol.; 60(1):41-8 (Jul. 1996).

Kobayashi et al., "Amended structure of side chains in a cell wall mannan from *Candida albicans* serotype A strain grown in yeast extract—Sabouraud liquid medium under acidic conditions: detection of the branched side chains corresponding to antigenic factor 4.", FEMS Microbiol Lett.;152(2):235-42 (Jul. 15, 1997).

Koizumi et al., Experimental studies of ischemic brain edema. 1. A new experimental model of cerebral embolism in rats in which recirculation can be introduced in the ischemic area. Jpn J Stroke 1986;8:1-8.

Kozyr et al., "Production of DNA-hydrolyzing antibody BV04-01 Fab fragment in methylotrophic yeast Pichia pastoris" Mol Biol (Mosk). Nov.-Dec. 2004;38(6):1067-75.

Krogh et al. "Hidden Markov models in computational biology. Applications to protein modeling." (1994) J. Mol. Biol. 235:1501-1531. O.

Kuno et al., "Possible involvement of neutrophil elastase in impaired mucosal repair in patients with ulcerative colitis," Journal of Gastroenterology, 2002, vol. 37, Supple XIV, pp. 22-32.

Kurjan et al., Structure of a yeast pheromone gene (MF alpha): a putative alpha-factor precursor contains four tandem copies of mature alpha-factor. Cell. Oct. 1982;30(3):933-43.

Lamminmaki et al., Crystal structure of a recombinant anti-estradiol Fab fragment in complex with 17beta-estradiol. J Biol Chem. Sep. 28, 2001;276(39):36687-94. Epub Jul. 12, 2001.

Laskowski et al., "Inhibitors with Class-Specific Reactive Sites," Ann. Rev. Biochem., 49:593-626 (1980).

Leatherbarrow et al., "Design of a Small Peptide-Based Proteinase Inhibitor by Modeling the Active-Site Region of Barley Chymotrypsin Inhibitor 2," Biochemistry, 30:10717-10721 (1991).

Lederman et al., A Single Amino Acid Substitution in a Common African Allele of the CD4 Molecule Ablates Binding of the Monoclonal Antibody, OKT4. Molecular Immunology. 1991;28(11):1171-1181.

Leeb-Lundberg et al. "International union of pharmacology. XLV. Classification of the kinin receptor family: from molecular mechanisms to pathophysiological consequences", (2005) Pharmacol Rev 57, 27-77.

Leonetti et al., "Increasing immunogenicity of antigens fused to Ig-binding proteins by cell surface targeting," The Journal of Immunology, 1998, vol. 160, pp. 3820-3827.

Levy et al., The therapeutic potential of a kallikrein inhibitor for treating hereditary angioedema. Expert Opin Investig Drugs. Sep. 2006;15(9):1077-90.

Ley et al., "Obtaining a Family of High-Affinity, High Specificity Protein Inhibitors of Plasmin and Plasma Kallikrein," Molecular Diversity, 2:119-124, (1996).

Li et al., β-Endorphin omission analogs: Dissociation of immunoreactivity from other biological activities. Proc. Natl. Acad. Sci. USA. Jun. 1980;77(6):3211-3214.

Lilla et al., "Active plasma kallikrein localizes to mast cells and regulates epithelial cell apoptosis, adipocyte differentiation, and stromal remodeling during mammary gland involution" J Biol Chem. 284(20):13792-13803 (2009).

(56) References Cited

OTHER PUBLICATIONS

Liu et al., Plasma kallikrein-kinin system and diabetic retinopathy. Biol Chem. Mar. 2013;394(3):319-28. doi: 10.1515/hsz-2012-0316. Author manuscript.
Lloyd et al., Modelling the human immune response: performance of a 1011 human antibody repertoire against a broad panel of therapeutically relevant antigens. Protein Eng Des Sel. Mar. 2009;22(3):159-68. doi: 10.1093/protein/gzn058. Epub Oct. 29, 2008.
Lohmann et al., Plasmin- and Plasminogen-Activator Inhibitors after Excimer Laser Photorefractive Keratectomy: New Concept in Prevention of Postoperative Myopic Regression and Haze, Refractive and Corneal Surgery, 9:300-302, (1993).
Longa et al., "Reversible middle cerebral artery occlusion without craniectomy in rats" Stroke 20 (1): 84-91 (1989).
Lucas et al., "The Binding of Human Plasminogen to Fibrin and Fibrinogen," J. Biol. Chem., 258:4249-4256 (1983).
Lumry et al., Interim Results of EDEMA2, A Multicenter, Open-Label, Repeat-Dosing Study of Intravenous and Subcutaneous Administration of Ecallantide (DX-88) in Hereditary Angioedema. J. Allergy and Clinical Immunology 117(2) (Suppl. 1):S179 Abstract699 (2006).
Maccallum et al., Antibody-antigen interactions: contact analysis and binding site topography. J Mol Biol. Oct. 11, 1996;262(5):732-45.
Macgilchrist, "Effect of the Serine Protease Inhibitor, Aprotinin, on Systemic Haemodynamics and Renal Function in Patients with Hepatic Cirrhosis and Ascites," Clin. Sci., 87:329-335 (1994).
Magklara et al., "Characterization of the enzymatic activity of human kallikrein 6: autoactivation, substrate specificity and regulation by inhibitors," Biochem. Biophys. Res. Commun., Aug. 8, 2003, vol. 307, No. 4, pp. 948-955, Abstract Only.
Mann et al., Hemostasis and Thrombosis, Chapter 10, 2nd Edition, Basic Principles and Clinical Practice: 148-161 (1987).
Mannucci, "Hemostatic Drugs" New England Journal of Medicine, Drug Therapy, 339(4):245-253 (1998).
March, Advanced Organic Chemistry, 3rd Edition, Reactions, Mechanisms, and Structure, John Wiley and Sons, New York: 396-398; 1057-1060; 1099-1100 (1985).
Markland et al., "Iterative Optimization of High-Affinity Protease Inhibitors Using Phage Display. 1. Plasmin," Biochemistry, 35:8045-8057 (1996).
Markland et al., "Iterative Optimization of High-Affinity Protease Inhibitors Using Phage Display. 2. Plasma Kallikrein and Thrombin," Biochemistry 35(24):8058-67 (1996).
Markland et al., "Selection for Protease Inhibitors Using Bacteriophage Display," Methods Enzymol., 267:28-51 (1996).
Markland, Cell. Biochem. Supp., 1994, O, vol. 18D, pp. 157, Abstract S 331.
Martin et al., "Animal models of neuropathic pain" Methods Mol Med. 84:233-42 (2003).
Mathews et al., Biochemistry, The Benjamin Cummins Publishing Co., Inc. Redwood City CA: 208-212 (1990).
Mattheakis et al. "An in vitro polysome display system for identifying ligands from very large peptide libraries" Proc. Natl. Acad. Sci. USA 91:9022 (1994).
Maxfield et al., "Conformation of poly(ethylene oxide) in the solid state, melt and solution measured by Raman scattering," Polymer, 1975, vol. 16, pp. 505-509.
Mayzel-Oreg, "Microsphere-induced embolic stroke: an MRI study" Magn Reson Med 51: 1232-8 (2004).
Mccarty, "Crystal-induced inflammation of the joints," Annual Reviews of Medicine, vol. 21, pp. 357-366 (1970).
Mcconnell et al., "New Leupeptin Analogues: Synthesis and Inhibition Data," J. Med. Chem., 33:86-93 (1990).
Merriam-Webster reference for the term "prevent." web date: 2010. 2 pages.
Merrifield, "Solid Phase Peptide Synthesis. I. The Synthesis of a Tetrapeptide," Am. Chem. Soc. 85:2149-2154 (1963).

Migliore et al: "Open pilot study of ultrasound-guided intra-articular injection of hylan G-F 20 (Synvisc) in the treatment of symptomatic hip osteoarthritis", Clinical Rheumatology; Journal of the International League of Associations for Rheumatology, Springer-Verlag, LO, vol. 24, No. 3, pp. 285-289 (Jun. 1, 2005).
Mine et al., "Structural mechanism for heparin-binding of the third Kunitz domain of human tissue factor pathway inhibitor," Biochemistry, 2002, vol. 41, pp. 78-85.
Miyajima et al., Secretion of mature mouse interleukin-2 by *Saccharomyces cerevisiae*: use of a general secretion vector containing promoter and leader sequences of the mating pheromone alpha-factor. Gene. 1985;37(1-3):155-61.
Molineux, "Pegylation: engineering improved pharmaceuticals for enhanced therapy," Cancer Treatment Reviews, 2002, vol. 28, pp. 13-16.
Monteseirin et al., "Plasma Kallikrein Amidolytic Activity in Bronchial Asthma," Allergol. Immunopathol., (Madr)., 20:211-214 (1992).
Moreland, "Intra-articular hyaluronan (hyaluronic acid) and hylans for the treatment of osteoarthritis: mechanisms of action," Arthritis Res. Ther, 2003, vol. 5, pp. 54-67.
Morishita et al., "Novel factor Xa and plasma kallikrein inhibitory-activities of the second Kunitz-type inhibitory domain of urinary trypsin inhibitor" Thromb Res, 73(3-4): p. 193-204 (1994).
Morrison "Transfectomas provide novel chimeric antibodies." (1985) Science 229:1202-1207.
Murkin et al., "Aprotinin significantly decreases bleeding and transfusion requirements in patients receiving aspirin and undergoing cardiac operations," J. Thorac. Cardiovasc. Surg., vol. 107, pp. 554-561 (1994).
Nadkarni et al., "Optimization of a mouse recombinant antibody fragment for efficient production from *Escherichia coli*" 2007 Protein Expr Purif 52(1):219-29.
Naess et al., "Effects of a Combined Drug Regimen on Tumour Necrosis Factor and Plasma Kallikrein Activity in Experimental Endotoxaemia," Eur. J. Surg., 160:77-86 (1994).
Nagai et al., Bicyclic turned dipeptide (BTD) as a β-turn mimetic; its design, synthesis and incorporation into bioactive peptides Tetrahedron, 49:3577-3592 (1993).
Nagai et al., Synthesis of a bicyclic dipeptide with the shape of β-turn central part. Tetrahedron Letters, 26 (5):647-650 (1985).
Needleman et al. "A general method applicable to the search for similarities in the amino acid sequences of two proteins" (1970) J. Mol. Biol. 48:444-453.
Nektar—Transforming Therapeutics, Nektar Advanced PEGylation: Polyethylene Glycol and Derivatives for Advanced PEGylation, pp. 1-24, catalogue 2004.
Nektar—Transforming Therapeutics, Nektar Molecule Engineering: Polyethylene Glycol and Derivatives for Advanced PEGylation, pp. 1-20, catalogue—2003.
Neuhaus et al., "Effect of Aprotinin on Intraoperative Bleeding and Fibrinolysis in Liver Transplantation," Lancet, 2: 924-925 (1989).
Ngo et al., "The protein folding problem and tertiary structure prediction, Chapter 14: Computational complexity protein structure prediction, and the Levinthal paradox," pp. 433-440 and 492-495 only (1994).
Ning et al., "Production of recombinant humanized anti-HBsAg Fab fragment from Pichia pastoris by fermentation.", J Biochem Mol Biol. ;38(3):294-9. (May 31, 2005).
Nof Corporation, "PEG Derivatives, Phospholipid and Drug Delivery Materials for Pharmaceutical Products and Formulations," pp. 1-59, catalogue Ver. 8—Apr. 2006.
Nof Corporation, "PEG Derivatives, Phospholipid and Drug Delivery Materials for Pharmaceuticals," pp. 1-46, catalogue—2003, 1st.
Nof Corporation, "PEG Derivatives, Phospholipid and Drug Delivery Materials for Pharmaceuticals," pp. 1-50, catalogue—2003 2nd.
Novotney et al., "Purification and Characterization of the Lipoprotein-associated Coagulation Inhibitor from Human Plasma," J. Biol. Chem. 264:18832-18837 (1989).
Nwariaku et al., "Effect of a bradykinin antagonist on the local inflammatory response following thermal injury" Burns, 22:324-327 (1996). (Abstract only).
Oi et al. "Chimeric Antibodies" (1986) BioTechniques 4:214.

(56) References Cited

OTHER PUBLICATIONS

Okamoto et al., "A Finding of Highly Selective Synthetic Inhibitor of Plasma Kallikrein; Its Action to Bradykinin Generation, Intrinsic Coagulation and Experimental DIC," Agents Actions Suppl., 38(I):198-205 (1992).
Okano et al., Chapter 9.1.2 Drug Action and Blood Concentration. Shin Yakuzaiaku Soron, revised 3rd Edition, Apr. 10, 1987:250-253.
O'Reilly et al., "Angiostatin: A Novel Angiogenesis Inhibitor That Mediates the Suppression of Metastases by a Lewis Lung Carcinoma," Cell, 79 317-328 (1994).
Padlan et al., Structure of an antibody-antigen complex: crystal structure of the HyHEL-10 Fab-lysozyme complex. Proc Natl Acad Sci U S A. Aug. 1989;86(15):5938-42.
Pan et al., "Reperfusion injury following cerebral ischemia: pathophysiology, MR imaging, and potential therapies," Neuroradiology, 2007, vol. 49, pp. 93-102.
Park et al., "Three Dimensional Structure of the Kringle Sequence: Structure of Prothrombin Fragment 1," Biochemistry, 25:3977-3982 (1986).
Paul. Fv Structure and Diversity in Three Dimensions. Fundamental Immunology, 3rd Edition. 1993:292-5.
Peng, "Experimental use of murine lupus models" Methods Mol Med. 102:227-72 (2004).
Petersen et al., "Inhibitory properties of separate recombinant Kunitz-type-protease-inhibitor domains from tissue-factor-pathway inhibitor," Eur. J. Biochem., 1996, vol. 235, pp. 310-316.
Phillips, "The challenge of gene therapy and DNA delivery," J. Pharm. Pharmacology, vol. 53, pp. 1169-1174 (2001).
Phipps et al., Plasma kallikrein mediates angiotensin II type 1 receptor-stimulated retinal vascular permeability. Hypertension. Feb. 2009;53(2):175-81. doi:10.1161/HYPERTENSIONAHA.108.117663. Epub Jan. 5, 2009.
Pintigny et al., "Aprotinin can inhibit the proteolytic activity of thrombin: a fluorescence and an enzymatic study," Eur. J. Biochem., 1992, vol. 207, pp. 89-95.
Piro et al., "Role for the Kunitz-3 domain of tissue factor pathway inhibitor-a in cell surface binding," Circulation, 2004, vol. 110, pp. 3567-3572.
Pirollo et al., "Targeted delivery of small interfering RNA: approaching effective cancer therapies," Cancer Res., 2008, vol. 68, No. 5, pp. 1247-1250.
Pitt et al., Rabbit monoarticular arthritis as a model for intra-articular drug injections. The local action of administered cortisol and alpha-1 proteinase inhibitor. Agents Actions. Dec. 1984;15(5-6):541-8.
Polypure, Products; PEG amines; PEG acids and amino acids, PEG thils and disulfides; Biotins, Apr. 2005.
Polypure, Products; PEG amines; PEG acids and amino acids; PEG thiols and disulfides; Biotins, Apr. 2004.
Powers et al., "Expression of Single-Chain Fv-Fc Fusions in *Pichia pastoris*", J. Immunol. Methods. 251:123-35 (2001).
Poznansky et al., "Growth hormone-albumin-conjugates reduced renal toxicity and altered plasma clearance," 1988, vol. 239, pp. 18-22.
Putterman, "Aprotinin Therapy in Septic Shock," ACTA Chir. Scand., 155:367 (1989).
Quanta Biodesign, Labeling, Derivatization and Crosslinking Reagents for Biological and Related Materials with dPEGTM, pp. 1-38, Mar. 12, 2004.
Quanta Biodesign, Labeling, Modification and Crosslinking Reagents incorporating our unique monodispersed dPEGTM, pp. 1-31, Nov. 5, 2004.
Quanta Biodesign, Leading innovator, producer and provider of monodisperse discrete PEGTM (dPEGTM) derivatives, Product Catalogue, pp. 1-51, Updated: Nov. 17, 2005.
Rahman et al., "Identification and functional importance of plasma kallikrein in the synovial fluids of patients with rheumatoid, psoriatic, and osteoarthritis," Annals of the Rheumatic Diseases, vol. 54, pp. 345-350 (1995).
Raspi, Kallikrein and kallikrein-like proteinases: purification and determination by chromatographic and electrophoretic methods. J Chromatogr B Biomed Appl. Sep. 20, 1996;684(1-2):265-87.
Reginato et al., "Genetics and experimental models of crystal-induced arthritis. Lessons learned from mice and men: is it crystal clear?" Curr Opin Rheumatol. 19(2): 134-45 (2007).
Reichert, "Technology evaluation: lumiliximab, Biogen Idec" Curr Opin Mol Ther., 6(6):675-83 (2004). (Abstract only).
Ren et al., "Inflammatory Models of Pain and Hyperalgesia" Ilar J. 40(3): 111-118 (1999).
Riedl et al., An open-label study to evaluate the long-term safety and efficacy of lanadelumab for prevention of attacks in hereditary angioedema: design of the HELP study extension. Clin Transl Allergy. Oct. 6, 2017;7: 36. doi: 10.1186/s13601-017-0172-9.
Robbins et al., Hemostasis and Thrombosis, Chapter 21, 2nd Edition, Basic Principles and Clinical Practice: 340-357 (1987).
Roberts et al., "Chemistry for peptide and protein PEGylation", Advanced Drug Delivery Reviews, 54, pp. 459-476, 2002.
Roberts et al., "Directed evolution of a protein: selection of potent neutrophil elastase inhibitor displayed on M13 fusion phage," PNAS USA, vol. 89, pp. 2429-2433 (1992).
Roberts et al., "Protease inhibitor display M13 phage: selection of high-affinity neutrophil elastase inhibitors," Gene, vol. 121, pp. 9-15 (1992).
Rossi et al., The Synthetic Peptide DX88 Binds to Endothelial Cells In Vitro and Retains the Inhibitory Activity on Kallikrein, International Immunopharmacology 2(9):1313, Abstract 142 (2002).
Rudikoff et al., Single amino acid substitution altering antigen-binding specificity. Proc Natl Acad Sci U S A. Mar. 1982;79(6):1979-83.
Sainz et al., "Fifty years of research on the plasma kallikrein-kinin system: from protein structure and function to cell biology and in-vivo pathophysiology" Thromb Haemost 98, 77-83, 2007.
Sartor et al., "Selective Kallikrein-Kinin System Activation in Inbred Rats Differentially Susceptible to Granulomatous Enterocolitis," Gastroenterology, 110:1467-1481 (1996).
Scarff et al., "Targeted disruption of SP13/Serpinb6 does not result in development of growth defects, leukocyte dysfunction, or susceptibility to stroke," Molecular and Cellular Biology, May 2004, pp. 4075-4082.
Scatchard, The Attractions of Proteins for Small Molecules and Ions, Ann. NY Acad. Sci, 51:660-672(1949).
Schaffirzel et al., "Ribosome display: an in vitro method for selection and evolution of antibodies from libraries" J Immunol Methods. 231(1-2): 119-35 (1999).
Schechter et al., On the Active Site of Proteases, III Mapping the Active Site of Papain; Specific Peptide Inhibitors of Papain, Biochemical and Biophysical Research Communications 32(5):898-902 (1968).
Schechter et al., On the Size of the Active Site on Proteases, I Papain, Biochemical and Biophysical Research Communications 27(2):157-162 (1967).
Schmaier et al., Hemostasis and Thrombosis, Chapter 2, 2nd Edition, Basic Principals and Clinical Practice: 18-38 (1987).
Schmaier, "Assembly, activation, and physiologic influence of the plasma kallikrein/kinin system" (2008) Int Immunopharmaco18, 161-165. Author manuscript.
Schmid-Elsaesser et al., "A critical reevaluation of the intraluminal thread model of focal cerebral ischemia: evidence of inadvertent premature reperfusion and subarachnoid hemorrhage in rats by laser-Doppler flowmetry" Stroke 29 (10): 2162-70(1989).
Schmidt et al., "A male accessory gland peptide with protease inhibitory activity in *Drosophila funebris*," J Biol Chem. Jun. 15, 1989;264(17):9745-9.
Schnabel et al., Aprotinin: Preparation by Partial Desulphurization of Aprotinin by Means of Raney Nickel and Comparison with Other Aprotinin Derivatives, Biol. Chem. Hoppe-Seyler, 367:1167-1176 (1986).
Schneider et al., Critical role of kallikrein in hereditary angioedema pathogenesis: a clinical trial of ecallantide, a novel kallikrein inhibitor. J Allergy Clin Immunol. Aug. 2007;120(2):416-22. Epub Jun. 7, 2007.

(56) References Cited

OTHER PUBLICATIONS

Schofield et al., "Monoclonal antibodies that neutralize HEV recognize an antigenic site at the carboxyterminus of an ORF2 protein vaccine" Vaccine (2003) 22(2):257-67.
Schoonbroodt et al., Human antibodies selected by phage display as potent and selective protease inhibitors. Human Antibodies. 2007;16(1-2):18-22.
Schoonooghe et al., "Efficient production of human bivalent and trivalent anti-MUC1 Fab-scFv antibodies in Pichia pastoris", BMC Biotechnol. Aug. 11, 2009;9:70.
Schopf, "IDEC-114 (IDEC)" Curr Opin Investig Drugs, 2(5):635-8 (2001). (Abstract only).
Schultz et al. "SMART, a simple modular architecture research tool: identification of signaling domains" (1998) Proc. Natl. Acad. Sci. USA 95:5857-5864.
Schultz et al., "SMART: a web-based tool for the study of genetically mobile domains" (2000) Nucl. Acids Res 28:231-234.
Schwartz et al., "Stability studies on derivatives of the bovine trypsin inhibitor," Biochemistry, vol. 26, pp. 3544-3551 (1987).
Sekiguchi et al., "Experimental spinal stenosis: relationship between degree of cauda equina compression, neuropathology, and pain" Spine 29, 1105-1111 (2004)).
Sexton et al., Comparison Of Plasma Kallikrein Inhibition By The Endogenous C1-Inhibitor Versus DX-2930, a Monoclonal Antibody Inhibitor. Blood. 2013;122: 1066. Abstract only.
Sexton et al., Discovery and characterization of fully human monoclonal antibody inhibitor of plasma kallikrein for the treatment of plasma kallikrein-mediated edema. J Allergy Clin Immunol. Feb. 2013;131(2): AB32. Suppl S. Annual meeting of the American Academy of Allergy, Asthma, and Immunology. San Antonio, TX, USA; Feb. 22-26.
Sexton et al., Specific inhibition of tissue kallikrein 1 with a human monoclonal antibody reveals a potential role in airway diseases. Biochem J. Aug. 13, 2009;422(2):383-92. doi: 10.1042/BJ20090010.
Shariat-Madar et al., Assembly and activation of the plasma kallikrein/kinin system: a new interpretation. Int Immunopharmacol. Dec. 2002;2(13-14):1841-9.
Sharma et al., "The kinin antagonist hoe 140 reduces acute paw oedema in rats caused by carrageenan, bradykinin and kaolin" Inflammopharmacology 6,9-17 (1998).
Shearwater Corporation, Polyethylene Glycol and Derivatives for Biomedical Applications, pp. 1-17, catalogue—2001.
Shearwater Polymers, Inc., Polyethylene Glycol and Derivatives, pp. 1-50, catalogue—Jul. 1997.
Shearwater Polymers, Inc., Polyethylene Glycol Derivatives: Functionalized Biocompatible Polymers for Research and Pharmaceuticals, pp. 1-50, catalogue—2000.
Shearwater Polymers, Inc., pp. 2-49, catalogue—Mar. 1995.
Sheppard et al., Acid-Labile Resin Linkage Agents for Use in Solid Phase Peptide Synthesis, Int. J. Peptide Protein Res., 20:451-454 (1982).
Sheridan et al., A Multicenter Trial of the Use of the Proteolytic Enzyme Inhibitor Aprotinin in Colorectal Surgery, Dis. Colon Rectum, 32:505-508 (1989).
Shibuya et al., "Primary Structure of Guinea Pig Plasma Prekallikrein", Immunopharmacology, vol. 45 (1-3), p. 127-134, Abstract p. 131, Fig 1, 2 (1999).
Siebeck et al., "Inhibition of plasma kallikrein with aprotinin in porcine endotoxin shock," J. Trauma, vol. 34, pp. 193-198 (1993).
Silverberg et al. "The Contact System and Its Disorders," in Blood: Principles and Practice of Hematology, Handin R. et al., eds. J B. Lippincott Co., Philadelphia, (1995).
Singer et al., "A porcine burn model" Methods Mol Med. 78: 107-19 (2003).
Skolnick et al., "From genes to protein structure and function: novel applications of computational approaches in the genomic era," Trends in Biotech., 2000, vol. 18, No. 1, pp. 34-39.

Slootstra et al., "Structural aspects of antibody-antigen interaction revealed through small random peptide libraries", Molecular Diversity,1, 87-96 (1996).
Smith et al. "Prolonged in vivo residence times of antibody fragments associated with albumin" Bioconjug Chem 12(5):750-756 (2001).
Smith, "Filamentous fusion phage: novel expression vectors that display cloned antigens on the virion surface" Science 228:1315-1317 (1985).
Sonhammer et al., "Pfam: a comprehensive database of protein domain families based on seed alignments" (1997) Proteins 28(3):405-420.
Sonis et al., "An animal model for mucositis induced by cancer chemotherapy" (1990) Oral Surg Oral Med Oral Pathol. 69:437-43.
Sonis et al., "Validation of a new scoring system for the assessment of clinical trial research of oral mucositis induced by radiation or chemotherapy. Mucositis Study Group." (1999) Cancer 85:2103-13.
Sprecher et al., "Molecular Cloning, Expression, and Partial Characterization of a Second Human Tissue-Factor-Pathway Inhibitor," Proc. Natl. Acad. Sci. USA, 91:3353-3357 (1994).
Stadnicki et al., "Activation of plasma contact and coagulation systems and neutrophils in the active phase of ulcerative colitis," Digestive Diseases and Sciences, 1997, vol. 42, No. 1, pp. 2356-2366.
Stadnicki et al., "Activation of the contact system and circulating neutrophil elastase in ulcerative colitis patients" 10th World Congress of Gastroenterology, p. 1166, 1994.
Stadnicki et al., "Activation of the Kallikrein-Kinin System in Indomethacin-Induced Entercolitis in Genetically Suseprible Rats," J. Invest. Med., 44:299A (1996).
Stadnicki et al., "Selective Plasma Kallikrein Inhibitor Attenuates Acute Intestinal Inflammation in Lewis Rat," Dig. Dis. Sci., 41:912-920 (1996).
Stevenson et al., "A mouse model of burn wounding and sepsis" Methods Mol Med. 78:95-105 (2003).
Stewart et al., Solid-Phase Peptide Synthesis (W.H. Freeman Co., San Francisco 1989). 6 pages.
Stultz et al., "Structural analysis based on state-space modeling." Protein Sci. 2:305-314 (1993).
Sunkureddi et al., "Clinical signs of gout," Hospital Physician, 2006, pp. 39-41. Retrieved from the internet <http://citeseerx.ist.psu.edu/viewdoc/download?doi=10.1.1.643.7808&rep=rep1&type=pdf> on Aug. 1, 2018.
Taby et al., "Inhibition of activated protein C by aprotinin and the uses of the insolubilized inhibitor for its purification," Thrombosis Research, 1990, vol. 59, pp. 27-35.
Taggart et al., "Inactivation of human-b-defensins 2 and 3 by elastolytic cathepsins1," The Journal of Immunology, 2003, vol. 170, pp. 931-937.
Takahashi et al., "Production of humanized Fab fragment against human high affinity IgE receptor in Pichia pastoris" Biosci Biotechnol Biochem 64(10):2138-44 (2000).
Tamura et al., "Focal cerebral ischaemia in the rat: 1. Description of technique and early neuropathological consequences following middle cerebral artery occlusion" J Cereb Blood Flow Metab 1: 53-60(1981).
Tanaka et al. "A novel rat model of abdominal aortic aneurysm using a combination of intraluminal elastase infusion and extraluminal calcium chloride exposure" J Vasc Surg. 50(6):1423-32 (2009).
Tang et al., Expression, crystallization, and three-dimensional structure of the catalytic domain of human plasma kallikrein. J Biol Chem. Dec. 9, 2005;280(49):41077-89. Epub Sep. 30, 2005.
The Merck Index, 11th edition, 1989. pp. 145, 146, 263, 427, 428, 1183, and 1184. 9 pages.
Tian et al., Synthesis of optically pure C alpha-methyl-arginine. Int J Pept Protein Res. Aug. 1992;40(2): 119-26.
Timmerman et al., "Functional reconstruction and synthetic mimicry of a conformational epitope using CLIPS TM technology" J. Mol. Recognit. 20:283-99 (2007).
Tomlinson et al. "Structural repertoire of the human Vk domain" EMBO J. 14(18):4628-3 (1995).
Tomlinson et al. "The repertoire of human germline VH sequences reveals about 50 groups of VH segments with different hypervariable loops" J. Mol. Biol. 227:776-798 (1992).

(56) References Cited

OTHER PUBLICATIONS

Travis et al., "Pulmonary perspective: potential problems in designing elastase inhibitors for therapy," Am. Rev. Respir. Dig., 1991, vol. 143, pp. 1412-1415.
Tremblay et al., "Anti-inflammatory activity of neutrophil elastase inhibitors," Current Opinion in Investigational Drugs, 2003, vol. 4, No. 5, pp. 556-565.
Tschesche et al., "Semisynthetic engineering of proteinase inhibitor homologues," Biochim. Biophys. Acta, vol. 913, pp. 97-101 (1987).
Uebel, Die Behandlung von Kniegelenksarthrosen mit Trasylol [The treatment of arthroses of the knee joint with Trasylol]. Langenbacks Arch. Chir., vol. 325, pp. 356-358 (1969).
Urlaub et al., "Isolation of Chinese hamster cell mutants deficient in dihydrofolate reductase activity", Proc. Natl. Acad. Sci. USA 77:4216-4220 (1980).
Vajdos et al., Comprehensive functional maps of the antigen-binding site of an anti-ErbB2 antibody obtained with shotgun scanning mutagenesis. J Mol Biol. Jul. 5, 2002;320(2):415-28.
Van Der Logt et al., "Intron-Exon Organization of the Human Gene Coding for the Lipoprotein-associated Coagulation Inhibitor: The Factor Xa Dependent of Inhibitor of the Extrinsic Pathway of Coagulation," Biochemistry, 30:1571-1577 (1991).
Van Dijl et al., "Signal Peptidase 1 of Bacillus subtillis: Patterns of Conserved Amino Acids in Prokaryotic and Eukaryotic Type 1 Signal Peptidases," The EMBO Journal, 11:2819-2828 (1992).
Varadi et al., "Location of Plasminogen-Binding Sites in Human Fibrin(ogen)," Biochemistry, 22:2440-2446 (1983).
Varadi et al., Segment of Fibrinogen Is in a Region Essential for Plasminogen Binding by Fibrin Fragment E, Biochemistry, 23:2108-2112 (1984).
Vedvick et al., "High-Level Secretion of Biologically Active Aprotinin from the Yeast Pichia pastoris," J. Ind. Microbiol., 7:197-201 (1991).
Veloso et al., A monoclonal anti-human plasma prekallikrein antibody that inhibits activation of prekallikrein by factor XIIa on a surface. Blood. Oct. 1987;70(4):1053-62.
Veronese, "Peptide and protein PEGylation: a review of problems and solutions," Biomaterials, Mar. 1, 2001, vol. 22, No. 5, pp. 405-417.
Veronez et al., The involvement of proteoglycans in the human plasma prekallikrein interaction with the cell surface. PLoS One. Mar. 12, 2014;9(3):e91280. doi: 10.1371/journal.pone.0091280. eCollection 2014.
Vidal et al., "Making sense of antisense," European Journal of Cancer, 2005, vol. 41, pp. 2812-2818.
Viswanathan et al., "Engineered protein protease inhibitors", Current Enzyme Inhibition, Jan. 1, 2009, pp. 87-98, vol. 5, No. 2, Betham Science Publishers Ltd., Hilversum, NL.
Volpe-Junior et al., "Augmented plasma and tissue kallikrein like activity in synovial fluid of patients with inflammatory articular diseases," Inflamm. Res., 1996, vol. 45, pp. 198-202.
Wade et al., Solid-phase synthesis of alpha-human atrial natriuretic factor: comparison of the Boc-polystyrene and Fmoc-polyamide methods. Biopolymers. 1986;25 Suppl:S21-37.
Wagner et al., High level expression, purification, and characterization of the Kunitz-type protease inhibitor domain of protease nexin-2/amyloid beta-protein precursor. Biochem Biophys Res Commun. Jul. 31, 1992; 186(2):1138-45.
Wang et al., "Monitoring of heparin-induced anticoagulation with kaolin-activated clotting time in cardiac surgical patients treated with aprotinin," Anesthesiology, vol. 77, pp. 1080-1084 (1992).
Ward et al. "Binding activities of a repertoire of single immunoglobulin variable domains secreted from *Escherichia coli*" (1989) Nature 341:544-546.
Wark et al., Latest technologies for the enhancement of antibody affinity. Adv Drug Deliv Rev. Aug. 7, 2006;58(5-6):657-70. Epub May 22, 2006.
Wark, "DX-890 (Dyax)", iDrugs, 5, pp. 586-589, Jun. 2002.
Watson et al., "Induction of reproducible brain infarction by photochemically initiated thrombosis" Ann Neurol17: 497-504 (1985).

Weaver, Animal studies paint misleading picture. Nature International Weekly Journal of Science. Published online Mar. 30, 2010. Retrieved on Aug. 1, 2017 from http://www.nature.com/news.2010.158.html.
Wedi, Lanadelumab to treat hereditary angioedema. Drugs Today (Barc). Jul. 2019;55(7):439-448. doi: 10.1358/dot.2019.55.7.2985293.
Wei et al., "Production and characterization of ectoine by *Marinococcus* sp. ECT1 isolated from a high-salinity environment." J Biosci Bioeng. Mar. 2011;111(3):336-42. Epub Dec. 15, 2010.
Wellington et al., "Tranexamic Acid: A review of its use in the management of menorrhagia", Drugs, vol. 63, No. 13, pp. 1417-1433, 2003.
Wells, "Additivity of Mutational Effects in Proteins", Biochemistry, vol. 29 (37), pp. 8509-8517 (1990).
Wendel et al., Lower Cardiac Troponin T Levels in Patients Undergoing Cardiopulmonary Bypass and Receiving High-Dose Aprotinin Therapy Indicate Reduction of Perioperative Myocardial Damage; Journal of Thoracic Cardiovascular Surgery, vol. 109, No. 6, pp. 1164-1172 (1995).
Williams et al. "Collagen-induced arthritis as a model for rheumatoid arthritis" Methods Mol Med. 98:207-16 (2004).
Wilson et al., "An animal model of chronic inflammatory pain: pharmacological and temporal differentiation from acute models" Eur J Pain. 10(6):537-49 (2006).
Wilson et al., "The Calculation and Synthesis of a Template Molecule," Tetrahedron, 49:3655-3663 (1993).
Wood, "Hemostatic Drugs" New England Journal of Medicine, Drug Therapy, 339(4):245-253 (1998).
Worthy et al., Kallikreins and kinins: mediators in inflammatory joint disease? Int J Exp Pathol. Aug. 1990;71(4):587-601.
Wu et al., Humanization of a murine monoclonal antibody by simultaneous optimization of framework and CDR residues. J Mol Biol. Nov. 19, 1999;294(1):151-62.
Wu, Lanadelumab for the treatment of hereditary angioedema. Expert Opin Biol Ther. Dec. 2019;19(12):1233-1245. doi: 10.1080/14712598.2019.1685490. Epub Nov. 4, 2019.
Wun et al., "Cloning and Characterization of a cDNA Coding for the Lipoprotein-associated Coagulation Inhibitor Shows that it Consists of Three Tandem Kunitz-type Inhibitory Domains," J. Biol. Chem. 263:6001-6004 (1988).
Yetkin et al., "The healing effect of TGF-[alpha] on gastric ulcer induced by acetylsalicylic acid in rats", International Journal of Pharmaceutics, vol. 277, No. 1-2, Jun. 1, 2004, pp. 163-172.
Zuraw et al., "Clinical practice. Hereditary angioedema" N Engl J Med. 2008;359:1027-36.
U.S. Appl. No. 14/773,766, filed Sep. 9, 2015, Nixon et al.
U.S. Appl. No. 16/445,304, filed Jun. 19, 2019, Sexton et al.
U.S. Appl. No. 16/411,242, filed May 14, 2019, Sexton et al.
U.S. Appl. No. 15/113,297, filed Jul. 21, 2016, Sexton et al.
U.S. Appl. No. 16/541,743, filed Aug. 15, 2019, Conley et al.
U.S. Appl. No. 15/562,671, filed Sep. 28, 2017, Chyung et al.
U.S. Appl. No. 16/556,524, filed Aug. 30, 2019, Peng et al.
PCT/US2016/065980, dated Mar. 1, 2017, International Search Report and Written Opinion.
PCT/US2016/065980, dated Jun. 21, 2018, International Preliminary Report on Patentability.
U.S. Appl. No. 17/010,354, filed Sep. 2, 2020, Sexton et al.
Banerji et al., Lanadelumab 300mg every 2 weeks effectively prevented hereditary angioedema attacks in the help study. Ann Allerg Asthma Immunol. Nov. 1, 2018;121(5):S5.
Faucette et al., Biomarker Assay for the detection of contact system activation. Ameri Soc. Hemato. Nov. 15, 2013; 122(21):2347. 55th Annual Meeting of the American Society-of-Hematology. New Orleans, LA, USA. Dec. 7-10, 2013.
Lumry et al., Subcutaneous self-administration of lanadelumab for prophylactic treatment in patients with hereditary angioededma (HAE). Ann Allerg Asthma Immunol. Nov. 2018;121(5):S57.
Sela-Culang et al., The structural basis of antibody-antigen recognition. Front Immunol. Oct. 8, 2013;4:302. doi: 10.3389/fimmu.2013.00302.

(56) References Cited

OTHER PUBLICATIONS

Wedner et al., Modeling and Analyses to Identify Potential Dosing Regimens of DX-2930 for the Long-Term Prophylaxis of Hereditary Angioedema. J All Clin Immunol. Feb. 1, 2016;137(2):AB252.

* cited by examiner

PLASMA KALLIKREIN INHIBITORS AND USES THEREOF FOR TREATING HEREDITARY ANGIOEDEMA ATTACK

CROSS REFERENCE TO RELATED APPLICATIONS

This application is a national stage filing under 35 U.S.C. § 371 of international application number PCT/US2016/065980, filed Dec. 9, 2016, which claims the benefit of the filing date of U.S. Provisional Application No. 62/266,175, filed Dec. 11, 2015, U.S. Provisional Application No. 62/266,192, filed Dec. 11, 2015, and U.S. Provisional Application No. 62/395,833, filed Sep. 16, 2016. The entire contents of each of these referenced applications are incorporated by reference herein.

BACKGROUND

Plasma kallikrein is a serine protease component of the contact system and a potential drug target for different inflammatory, cardiovascular, infectious (sepsis) and oncology diseases (Sainz I. M. et al., *Thromb Haemost* 98, 77-83, 2007). The contact system is activated by either factor XIIa upon exposure to foreign or negatively charged surfaces or on endothelial cell surfaces by prolylcarboxypeptidases (Sainz I. M. et al., *Thromb Haemost* 98, 77-83, 2007). Activation of the plasma kallikrein amplifies intrinsic coagulation via its feedback activation of factor XII and enhances inflammation via the production of the proinflammatory nonapeptide bradykinin. As the primary kininogenase in the circulation, plasma kallikrein is largely responsible for the generation of bradykinin in the vasculature. A genetic deficiency in the C1-inhibitor protein (C1-INH), the major natural inhibitor of plasma kallikrein, leads to hereditary angioedema (HAE). Patients with HAE suffer from acute attacks of painful edema often precipitated by unknown triggers (Zuraw B. L. et al., *N Engl J Med* 359, 1027-1036, 2008).

SUMMARY

Provided herein are regimens for treating hereditary angioedema (HAE) attack, reducing the rate of HAE attack, or blocking HAE attack using antibodies capable of binding and inhibiting human plasma kallikrein (pKal) in active form, for example, antibodies that bind to the same epitope as DX-2930 (a.k.a. SHP643) or competes against DX-2930 for binding to active human pKal.

In some aspects, the present disclosure provides methods for treating hereditary angioedema (HAE) attack or reducing the rate of HAE attack, comprising administering (e.g., subcutaneously) to a subject in need thereof any of the anti-pKal antibodies described herein (e.g., DX-2930) in single and/or multiple doses. In some embodiments, the antibody is administered to a subject (e.g., a human patient) at multiple doses in a first treatment period, e.g., 26 weeks. For example, the antibody can be administered at about 300 mg every two weeks, about 300 mg every four weeks, or about 150 mg every four weeks in the first treatment period.

Any of the methods described herein may further comprise administering to the subject the antibody for a second treatment period (e.g., 26 weeks) after the first treatment period. In some embodiments, the first dose of the second treatment period is about two weeks after the last dose of the first treatment period. In some embodiments, the second treatment period comprises multiple doses of the antibody at about 300 mg every two weeks for, e.g., 26 weeks.

Alternatively, the methods may further comprise administering to the subject a single dose of the antibody (e.g., about 300 mg) after the first treatment period. The single dose may be followed up with one or more doses of the antibody (e.g., about 300 mg every 2 weeks) of the antibody if an HAE attack occurs after the single dose. The first dose of the follow-on treatment can be within one week after the HAE attack. In some embodiments, the single dose and the first dose of the follow-on treatment are at least 10 days apart.

Other aspects of the present disclosure provide methods for treating hereditary angioedema (HAE) attack or reducing the rate of HAE attack in a subject that has undergone a prior treatment of HAE, comprising (i) administering (e.g., subcutaneously) to a subject in need thereof any of the anti-pKal antibodies described herein (e.g., DX-2930) antibody at a single dose of about 300 mg; and (ii) further administering to the subject the antibody at multiple doses of about 300 mg every two weeks, if the subject experiences an HAE attack after (i). The subject may have undergone a first HAE treatment as described herein. For example, the first HAE treatment can be a treatment involving the same antibody (e.g., DX-2930). In some examples, the first HAE treatment involves administering the antibody in multiple doses of about 150 mg or 300 mg every four weeks or administering the antibody in multiple doses of about 300 mg every two weeks. Alternatively or in addition, the first dose of the multiple doses is given to the subject within one week after the HAE attack.

In any of the treatment methods described herein, the subject can be a human patient having, suspected of having, or at risk for HAE. In some embodiments, the subject is a human patient having HAE type I or type II. For example, the subject may have at least one HAE attack in the four weeks prior to the first dose of the first treatment period or at least two HAE attacks in the eight weeks prior to the first dose of the first treatment period. In other examples, the subject can be a human patient who had experienced at least two HAE attacks per year prior to the treatment. Alternatively or in addition, the subject is a human patient who is free of prior treatment, for example, at least two weeks before the first dose of the first treatment period.

In some embodiments, the subject to be treated by any of the methods described herein, which involve the use of any of the anti-pKal antibody as also described herein (e.g., DX-2930) have received one or more HAE treatment before the first dose of the anti-pKal antibody. Such prior HAE treatments may involve an C1-inhibitor (e.g., C1-INH), a plasma kallikrein inhibitor (e.g., ecallantide), a bradykinin receptor antagonist (e.g., icatibant), an attenuated androgen (e.g., danazol), an anti-fibrinolytic agent (e.g., tranexamic acid) or a combination thereof. Such a subject may undergo a taper period to gradually transit from the prior HAE treatment to the anti-pKal antibody treatment described herein. In some examples, the tapering period may range from 2-4 weeks. The prior HAE treatment may terminate either before the first dose of the anti-pKal antibody or within three weeks after the first dose of the anti-pKal antibody is given to the subject. Alternatively, the subject may be directly transitioned from any of the prior HAE treatment to the anti-pKal antibody treatment as described herein.

In some embodiments, the subject is free of a long-term prophylaxis for HAE, or an HAE treatment involving an angiotensin-converting enzyme (ACE) inhibitor, an estrogen-containing medication, or an androgen prior to the first treatment period, during the first treatment period, and/or during the second treatment period.

The anti-pKal antibody for use in the treatment regimens described herein may be a full length antibody or an antigen-binding fragment thereof. In some embodiments, the antibody may comprise the same CDRs as DX-2930. In one example, the antibody is DX-2930.

In any of the methods described herein, the antibody can be formulated in a pharmaceutical composition comprising a pharmaceutically acceptable carrier. In some embodiments, the pharmaceutically composition comprises sodium phosphate, citric acid, histidine, sodium chloride, and Tween 80. In one example, the sodium phosphate is at a concentration of about 30 mM, the citric acid is at a concentration of about 19 mM, the histidine is at a concentration of about 50 mM, the sodium chloride is at a concentration of about 90 mM, and/or the polysorbate 80 is at about 0.01%.

The details of one or more embodiments of the invention are set forth in the description below. Other features or advantages of the present invention will be apparent from the following drawing and detailed description of several embodiments, and also from the appended claims.

DETAILED DESCRIPTION

Definitions

Figure 1:
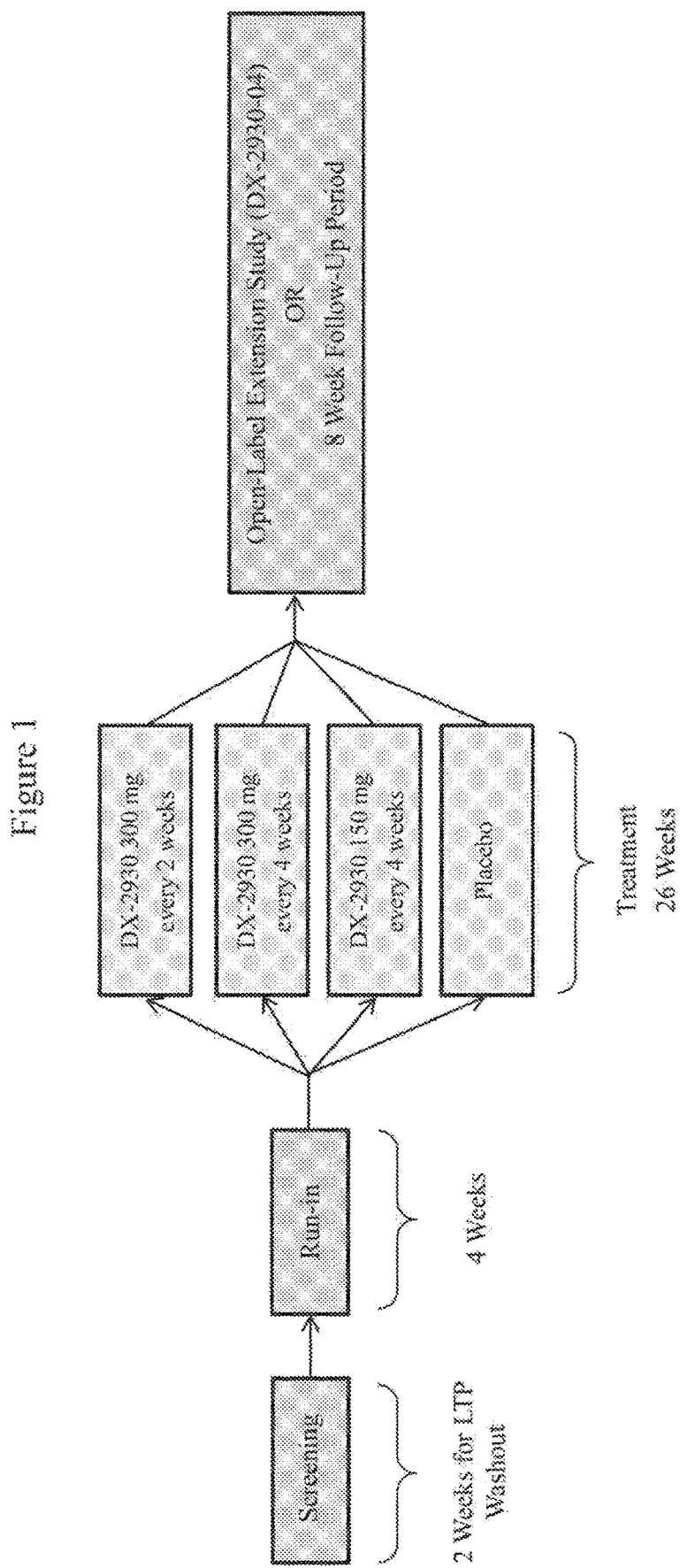
FIG. 1 shows an exemplary dosing regimen comprising a first treatment period in which patients are administered DX-2930 at a dose of 300 mg every two weeks, 300 mg every four weeks, or 150 mg every 4 weeks.
Figure 2:
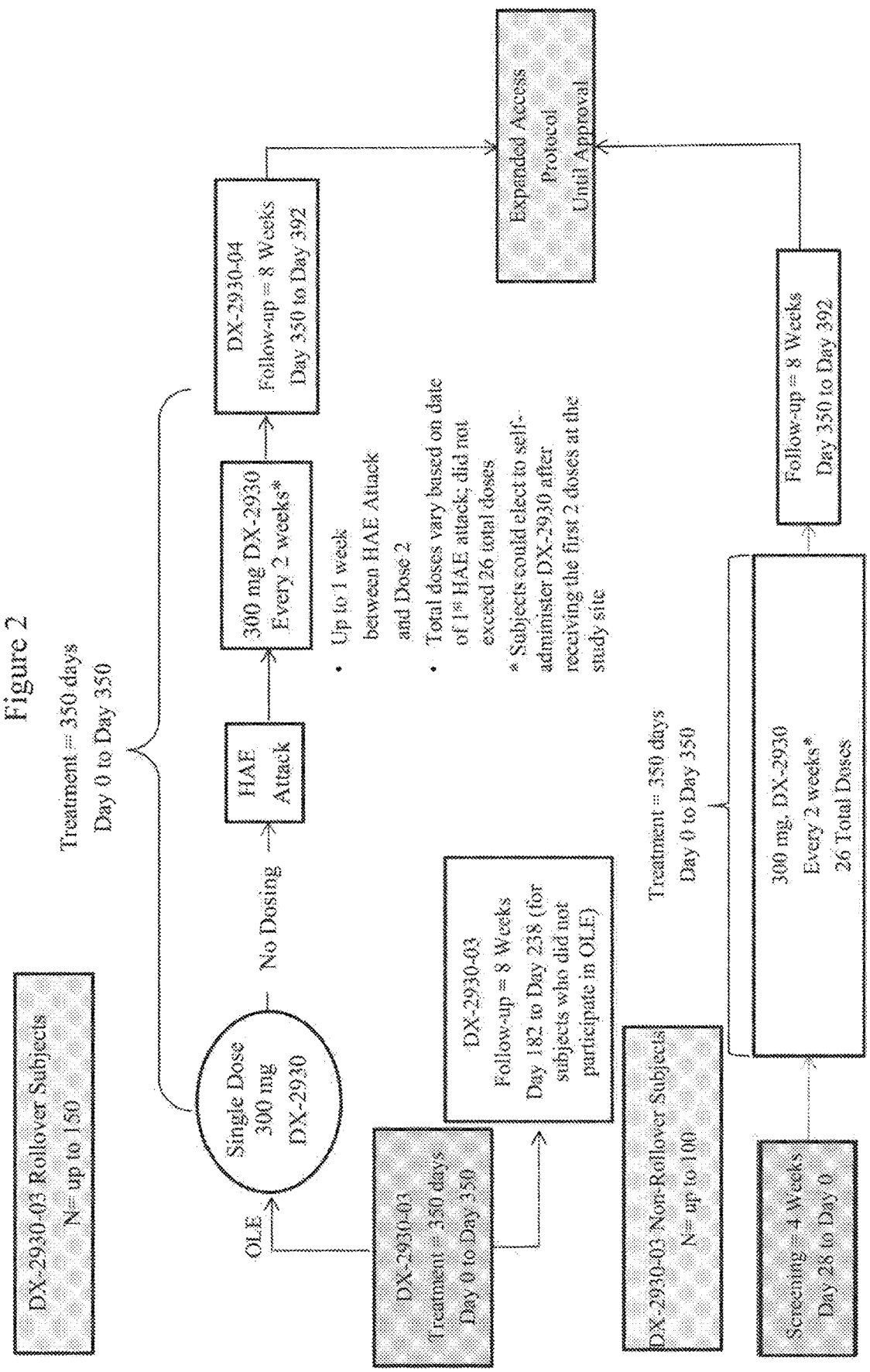
FIG. 2 shows an exemplary dosing regimen comprising a second treatment period following a first treatment period. In the second treatment period, patients are administered a single dose of DX-2930 at 300 mg. If the patient experiences a HAE attack, the antibody is subsequently administered at a dose of 300 mg every two weeks.

For convenience, before further description of the present invention, certain terms employed in the specification, examples and appended claims are defined here. Other terms are defined as they appear in the specification.

The singular forms "a", "an", and "the" include plural references unless the context clearly dictates otherwise.

As used herein, the term "about" refers to a particular value +/−5%. For example, an antibody at about 300 mg includes any amount of the antibody between 285 mg-315 mg.

The term "antibody" refers to an immunoglobulin molecule capable of specific binding to a target, such as a carbohydrate, polynucleotide, lipid, polypeptide, etc., through at least one antigen recognition site located in the variable region of the immunoglobulin molecule. An antibody may include at least one heavy (H) chain that comprises a heavy chain immunoglobulin variable domain ($V_H$), at least one light chain that comprises a light chain immunoglobulin variable domain ($V_L$), or both. For example, an antibody can include a heavy (H) chain variable region (abbreviated herein as $V_H$ or HV) and a light (L) chain variable region (abbreviated herein as $V_L$ or LV). In another example, an antibody includes two heavy (H) chain variable regions and two light (L) chain variable regions.

As used herein, the term "antibody" encompasses not only intact (i.e., full-length) polyclonal or monoclonal antibodies, but also antigen-binding fragments thereof (such as Fab, Fab', F(ab')$_2$, Fv), single chain (scFv), domain antibody (dAb) fragments (de Wildt et. al., *Euro. J. Immunol.* (1996) 26(3): 629-639), any mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Antibodies may be from any source, but primate (human and non-human primate) and primatized are preferred.

The $V_H$ and/or $V_L$ regions may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form an antigen binding site, e.g., a structure that preferentially interacts with plasma kallikrein.

The $V_H$ and $V_L$ regions can be further subdivided into regions of hypervariability, termed "complementarity determining regions" ("CDRs"), interspersed with regions that are more conserved, termed "framework regions" ("FRs"). The extent of the framework region and CDRs have been defined (see, Kabat, E. A., et al. (1991) *Sequences of Proteins of Immunological Interest*, Fifth Edition, U.S. Department of Health and Human Services, NIH Publication No. 91-3242, and Chothia, C. et al. (1987) *J. Mol. Biol.* 196:901-917). Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

In addition to the $V_H$ or $V_L$ regions, the heavy chain or light chain of the antibody can further include all or part of a heavy or light chain constant region. In one embodiment, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system. The light chains of the immunoglobulin may be of type kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and/or LC CDR3. Each of the light chain (LC) and/or heavy chain (HC) CDRs can be human. HC CDR3 can be human. One or more of the framework regions can be human, e.g., FR1, FR2, FR3, and/or FR4 of the HC and/or LC. For example, the Fc region can be human. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. In one embodiment, the framework (FR) residues of a selected Fab can be converted to the amino-acid type of the corresponding residue in the most similar primate germline gene, especially the human germline gene. One or more of the constant regions can be human or effectively human. For example, at least 70, 75, 80, 85, 90, 92, 95, 98, or 100% of an immunoglobulin variable domain, the constant region, the constant domains (CH1, CH2, CH3, and/or CL1), or the entire antibody can be human or effectively human.

An antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the many immunoglobulin variable region genes. Full-length immunoglobulin "light chains" (about 25 KDa or about 214 amino acids) are encoded by a variable region gene at the NH2-terminus (about 110 amino acids) and a kappa or lambda constant region gene at the COOH-terminus. Full-length immunoglobulin "heavy chains" (about 50 KDa or about 446 amino acids), are similarly encoded by a variable region gene (about 116 amino acids) and one of the other aforementioned constant region genes, e.g., gamma (encoding about 330 amino acids). The length of human HC varies considerably because HC CDR3 varies from about 3 amino-acid residues to over 35 amino-acid residues.

The term "antigen-binding fragment" of a full length antibody refers to one or more fragments of a full-length antibody that retain the ability to specifically bind to a target of interest. Examples of binding fragments encompassed within the term "antigen-binding fragment" of a full length antibody and that retain functionality include (i) a Fab fragment, a monovalent fragment consisting of the $V_L$, $V_H$, $C_L$ and CH1 domains; (ii) a F(ab')2 fragment, a bivalent fragment including two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv). See e.g., U.S. Pat. Nos. 5,260,203, 4,946,778, and 4,881,175; Bird et al. (1988) Science 242:423-426; and Huston et al. (1988) Proc. Natl. Acad. Sci. USA 85:5879-5883. Antibody fragments can be obtained using any appropriate technique including conventional techniques known to those with skill in the art.

The term "monospecific antibody" refers to an antibody that displays a single binding specificity and affinity for a particular target, e.g., epitope. This term includes a "monoclonal antibody" or "monoclonal antibody composition," which as used herein refers to a preparation of antibodies or fragments thereof of single molecular composition, irrespective of how the antibody was generated. Antibodies are "germlined" by reverting one or more non-germline amino acids in framework regions to corresponding germline amino acids of the antibody, so long as binding properties are substantially retained.

The inhibition constant ($K_i$) provides a measure of inhibitor potency; it is the concentration of inhibitor required to reduce enzyme activity by half and is not dependent on enzyme or substrate concentrations. The apparent $K_i$ ($K_{i,app}$) is obtained at different substrate concentrations by measuring the inhibitory effect of different concentrations of inhibitor (e.g., inhibitory binding protein) on the extent of the reaction (e.g., enzyme activity); fitting the change in pseudo-first order rate constant as a function of inhibitor concentration to the Morrison equation (Equation 1) yields an estimate of the apparent $K_i$ value. The $K_i$ is obtained from the y-intercept extracted from a linear regression analysis of a plot of $K_{i,app}$ versus substrate concentration.

$$v = v_o - v_o\left(\frac{(K_{i,app} + I + E) - \sqrt{(K_{i,app} + I + E)^2 - 4 \cdot I \cdot E}}{2 \cdot E}\right) \quad \text{Equation 1}$$

Where v=measured velocity; v0=velocity in the absence of inhibitor; $K_{i,app}$=apparent inhibition constant; I=total inhibitor concentration; and E=total enzyme concentration.

As used herein, "binding affinity" refers to the apparent association constant or $K_A$. The $K_A$ is the reciprocal of the dissociation constant ($K_D$). A binding antibody may, for example, have a binding affinity of at least 105, 106, 107, 108, 109, 1010 and 1011 M-1 for a particular target molecule, e.g., plasma kallikrein. Higher affinity binding of a binding antibody to a first target relative to a second target can be indicated by a higher $K_A$ (or a smaller numerical value $K_D$) for binding the first target than the $K_A$ (or numerical value $K_D$) for binding the second target. In such cases, the binding antibody has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 30, 40, 50, 70, 80, 90, 100, 500, 1000, 10,000 or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH 7.4, 150 mM NaCl, 0.005% (v/v) Surfactant P20). These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

$$[Bound]=N \cdot [Free]/((1/K_A)+[Free]).$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2 fold higher, to obtain a qualitative measurement of affinity, or to obtain an inference of affinity, e.g., by activity in a functional assay, e.g., an in vitro or in vivo assay.

The term "binding antibody" (or "binding protein" used interchangeably herein) refers to a antibody that can interact with a target molecule. This term is used interchangeably with "ligand." A "plasma kallikrein binding antibody" refers to an antibody that can interact with (e.g., bind) plasma kallikrein, and includes, in particular, antibodies that preferentially or specifically interact with and/or inhibit plasma kallikrein. An antibody inhibits plasma kallikrein if it causes a decrease in the activity of plasma kallikrein as compared to the activity of plasma kallikrein in the absence of the antibody and under the same conditions.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

It is possible for one or more framework and/or CDR amino acid residues of a binding protein to include one or more mutations (for example, substitutions (e.g., conservative substitutions or substitutions of non-essential amino acids), insertions, or deletions) relative to a binding protein described herein. A plasma kallikrein binding protein may have mutations (e.g., substitutions (e.g., conservative substitutions or substitutions of non-essential amino acids), insertions, or deletions) (e.g., at least one, two, three, or four, and/or less than 15, 12, 10, 9, 8, 7, 6, 5, 4, 3, or 2 mutations) relative to a binding protein described herein, e.g., mutations which do not have a substantial effect on protein function. The mutations can be present in framework regions, CDRs, and/or constant regions. In some embodiments, the mutations are present in a framework region. In some embodiments, the mutations are present in a CDR. In some embodiments, the mutations are present in a constant region. Whether or not a particular substitution will be tolerated, i.e., will not adversely affect biological properties, such as binding activity, can be predicted, e.g., by evaluating whether the mutation is conservative or by the method of Bowie, et al. (1990) *Science* 247:1306-1310.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

An "epitope" refers to the site on a target compound that is bound by a binding protein (e.g., an antibody such as a Fab or full length antibody). In the case where the target compound is a protein, the site can be entirely composed of amino acid components, entirely composed of chemical modifications of amino acids of the protein (e.g., glycosyl moieties), or composed of combinations thereof. Overlapping epitopes include at least one common amino acid residue, glycosyl group, phosphate group, sulfate group, or other molecular feature.

A first binding antibody "binds to the same epitope" as a second binding antibody if the first binding antibody binds to the same site on a target compound that the second binding antibody binds, or binds to a site that overlaps (e.g., 50%, 60%, 70%, 80%, 90%, or 100% overlap, e.g., in terms of amino acid sequence or other molecular feature (e.g., glycosyl group, phosphate group, or sulfate group)) with the site that the second binding antibody binds.

A first binding antibody "competes for binding" with a second binding antibody if the binding of the first binding antibody to its epitope decreases (e.g., by 10%, 20%, 30%, 40%, 50%, 60%, 70%, 80%, 90%, 100%, or more) the amount of the second binding antibody that binds to its epitope. The competition can be direct (e.g., the first binding antibody binds to an epitope that is the same as, or overlaps with, the epitope bound by the second binding antibody), or indirect (e.g., the binding of the first binding antibody to its epitope causes a steric change in the target compound that decreases the ability of the second binding antibody to bind to its epitope).

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

In a preferred embodiment, the length of a reference sequence aligned for comparison purposes is at least 30%, preferably at least 40%, more preferably at least 50%, even more preferably at least 60%, and even more preferably at least 70%, 80%, 90%, 92%, 95%, 97%, 98%, or 100% of the length of the reference sequence. For example, the reference sequence may be the length of the immunoglobulin variable domain sequence.

A "humanized" immunoglobulin variable region is an immunoglobulin variable region that is modified to include a sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762.

An "isolated" antibody refers to an antibody that is removed from at least 90% of at least one component of a natural sample from which the isolated antibody can be obtained. Antibodies can be "of at least" a certain degree of purity if the species or population of species of interest is at least 5, 10, 25, 50, 75, 80, 90, 92, 95, 98, or 99% pure on a weight-weight basis.

A "patient," "subject" or "host" (these terms are used interchangeably) to be treated by the subject method may mean either a human or non-human animal. A subject may be a subject that has undergone a prior treatment for HAE, such as a treatment involving an antibody described herein. In some embodiments, the subject is a pediatric subject (e.g., an infant, child, or adolescent subject).

The terms "prekallikrein" and "preplasma kallikrein" are used interchangeably herein and refer to the zymogen form of active plasma kallikrein, which is also known as prekallikrein.

As used herein, the term "substantially identical" (or "substantially homologous") is used herein to refer to a first amino acid or nucleic acid sequence that contains a sufficient number of identical or equivalent (e.g., with a similar side chain, for example, conserved amino acid substitutions) amino acid residues or nucleotides to a second amino acid or nucleic acid sequence such that the first and second amino acid or nucleic acid sequences have (or encode proteins having) similar activities, e.g., a binding activity, a binding preference, or a biological activity. In the case of antibodies, the second antibody has the same specificity and has at least 50%, at least 25%, or at least 10% of the affinity relative to the same antigen.

Sequences similar or homologous (e.g., at least about 85% sequence identity) to the sequences disclosed herein are also part of this application. In some embodiments, the sequence identity can be about 85%, 90%, 91%, 92%, 93%, 94%, 95%, 96%, 97%, 98%, 99% or higher. In some embodiments, a plasma kallikrein binding antibody can have about 85%, 90%, 91%, 92%, 93%, 94%, 95%, 96%, 97%, 98%, 99% or higher sequence identity to an antibody described herein. In some embodiments, a plasma kallikrein binding antibody can have about 85%, 90%, 91%, 92%, 93%, 94%, 95%, 96%, 97%, 98%, 99% or higher sequence identity in the HC and/or LC framework regions (e.g., HC and/or LC FR 1, 2, 3, and/or 4) to an antibody described herein (e.g., DX-2930). In some embodiments, a plasma kallikrein binding antibody can have about 85%, 90%, 91%, 92%, 93%, 94%, 95%, 96%, 97%, 98%, 99% or higher sequence identity in the HC and/or LC CDRs (e.g., HC and/or LC CDR1, 2, and/or 3) to an antibody described herein (e.g., DX-2930). In some embodiments, a plasma kallikrein binding antibody can have about 85%, 90%, 91%, 92%, 93%, 94%, 95%, 96%, 97%, 98%, 99% or higher sequence identity in the constant region (e.g., CH1, CH2, CH3, and/or CL1) to an antibody described herein (e.g., DX-2930).

In addition, substantial identity exists when the nucleic acid segments hybridize under selective hybridization conditions (e.g., highly stringent hybridization conditions), to the complement of the strand. The nucleic acids may be present in whole cells, in a cell lysate, or in a partially purified or substantially pure form.

Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02. Particular binding proteins may show a difference, e.g., in specificity or binding that are statistically significant (e.g., P value<0.05 or 0.02). The terms "induce", "inhibit", "potentiate", "elevate", "increase", "decrease" or the like, e.g., which denote distinguishable qualitative or quantitative differences between two states, may refer to a difference, e.g., a statistically significant difference, between the two states.

A "therapeutically effective dosage" preferably modulates a measurable parameter, e.g., plasma kallikrein activity, by a statistically significant degree or at least about 20%, more preferably by at least about 40%, even more preferably by at least about 60%, and still more preferably by at least about 80% relative to untreated subjects. The ability of a compound to modulate a measurable parameter, e.g., a disease-associated parameter, can be evaluated in an animal model system predictive of efficacy in human disorders and conditions. Alternatively, this property of a composition can be evaluated by examining the ability of the compound to modulate a parameter in vitro.

The term "treating" as used herein refers to the application or administration of a composition including one or more active agents to a subject, who has an allergic disease, a symptom of the allergic disease, or a predisposition toward the allergic disease, with the purpose to cure, heal, alleviate, relieve, alter, remedy, ameliorate, improve, or affect the disease, the symptoms of the disease, or the predisposition toward the disease. "Prophylactic treatment," also known as "preventive treatment," refers to a treatment that aims at protecting a person from, or reducing the risk for a disease to which he or she has been, or may be, exposed. In some embodiments, the treatment methods described herein aim at preventing occurrence and/or recurrence of HAE.

The term "preventing" a disease in a subject refers to subjecting the subject to a pharmaceutical treatment, e.g., the administration of a drug, such that at least one symptom of the disease is prevented, that is, administered prior to clinical manifestation of the unwanted condition (e.g., disease or other unwanted state of the host animal) so that it protects the host against developing the unwanted condition. "Preventing" a disease may also be referred to as "prophylaxis" or "prophylactic treatment."

A "prophylactically effective amount" refers to an amount effective, at dosages and for periods of time necessary, to achieve the desired prophylactic result. Typically, because a prophylactic dose is used in subjects prior to or at an earlier stage of disease, the prophylactically effective amount will be less than the therapeutically effective amount.

Antibodies Binding to Plasma Kallikrein (pKal)

Plasma kallikrein binding antibodies (anti-pKal antibodies) for use in the methods described herein can be full-length (e.g., an IgG (including an IgG1, IgG2, IgG3, IgG4), IgM, IgA (including, IgA1, IgA2), IgD, and IgE) or can include only an antigen-binding fragment (e.g., a Fab, F(ab')$_2$ or scFv fragment. The binding antibody can include two heavy chain immunoglobulins and two light chain immunoglobulins, or can be a single chain antibody. Plasma kallikrein binding antibodies can be recombinant proteins such as humanized, CDR grafted, chimeric, deimmunized, or in vitro generated antibodies, and may optionally include constant regions derived from human germline immunoglobulin sequences. In one embodiment, the plasma kallikrein binding antibody is a monoclonal antibody.

In one aspect, the disclosure features an antibody (e.g., an isolated antibody) that binds to plasma kallikrein (e.g., human plasma kallikrein and/or murine kallikrein) and includes at least one immunoglobulin variable region. For example, the antibody includes a heavy chain (HC) immunoglobulin variable domain sequence and/or a light chain (LC) immunoglobulin variable domain sequence. In one embodiment, the antibody binds to and inhibits plasma kallikrein, e.g., human plasma kallikrein and/or murine kallikrein.

The antibody can include one or more of the following characteristics: (a) a human CDR or human framework region; (b) the HC immunoglobulin variable domain sequence comprises one or more (e.g., 1, 2, or 3) CDRs that are at least 85, 88, 89, 90, 91, 92, 93, 94, 95, 96, 97, 98, 99, or 100% identical to a CDR of a HC variable domain described herein; (c) the LC immunoglobulin variable domain sequence comprises one or more (e.g., 1, 2, or 3) CDRs that are at least 85, 88, 89, 90, 91, 92, 93, 94, 95, 96, 97, 98, 99, or 100% identical to a CDR of a LC variable domain described herein; (d) the LC immunoglobulin variable domain sequence is at least 85, 88, 89, 90, 91, 92, 93, 94, 95, 96, 97, 98, 99, or 100% identical to a LC variable domain described herein (e.g., overall or in framework regions or CDRs); (e) the HC immunoglobulin variable domain sequence is at least 85, 88, 89, 90, 91, 92, 93, 94, 95, 96, 97, 98, 99, or 100% identical to a HC variable domain described herein (e.g., overall or in framework regions or CDRs); (f) the antibody binds an epitope bound by an antibody described herein, or competes for binding with an antibody described herein; (g) a primate CDR or primate framework region; (h) the HC immunoglobulin variable domain sequence comprises a CDR1 that differs by at least one amino acid but by no more than 2 or 3 amino acids from the CDR1 of a HC variable domain described herein; (i) the HC immunoglobulin variable domain sequence comprises a CDR2 that differs by at least one amino acid but by no more than 2, 3, 4, 5, 6, 7, or 8 amino acids from the CDR2 of a HC variable domain described herein; (j) the HC immunoglobulin variable domain sequence comprises a CDR3 that differs by at least one amino acid but by no more than 2, 3, 4, 5, or 6 amino acids from the CDR3 of a HC variable domain described herein; (k) the LC immunoglobulin variable domain sequence comprises a CDR1 that differs by at least one amino acid but by no more than 2, 3, 4, or 5 amino acids from the CDR1 of a LC variable domain described herein; (l) the LC immunoglobulin variable domain sequence comprises a CDR2 that differs by at least one amino acid but by no more than 2, 3, or 4 amino acids from the CDR2 of a LC variable domain described herein; (m) the LC immunoglobulin variable domain sequence comprises a CDR3 that differs by at least one amino acid but by no more than 2, 3, 4, or 5 amino acids from the CDR3 of a LC variable domain described herein; (n) the LC immunoglobulin variable domain sequence differs by at least one amino acid but by no more than 2, 3, 4, 5, 6, 7, 8, 9, or 10 amino acids from a LC variable domain described herein (e.g., overall or in framework regions or CDRs); and (o) the HC immunoglobulin variable domain sequence differs by at least one amino acid but by no more than 2, 3, 4, 5, 6, 7, 8, 9, or 10 amino acids from a HC variable domain described herein (e.g., overall or in framework regions or CDRs).

The plasma kallikrein binding protein may be an isolated antibody (e.g., at least 70, 80, 90, 95, or 99% free of other proteins). In some embodiments, the plasma kallikrein binding antibody, or composition thereof, is isolated from antibody cleavage fragments (e.g., DX-2930) that are inactive or partially active (e.g., bind plasma kallikrein with a $K_{i,app}$ of 5000 nM or greater) compared to the plasma kallikrein binding antibody. For example, the plasma kallikrein binding antibody is at least 70% free of such antibody cleavage fragments; in other embodiments the binding antibody is at least 80%, at least 90%, at least 95%, at least 99% or even 100% free from antibody cleavage fragments that are inactive or partially active.

The plasma kallikrein binding antibody may additionally inhibit plasma kallikrein, e.g., human plasma kallikrein.

In some embodiments, the plasma kallikrein binding antibody does not bind prekallikrein (e.g., human prekallikrein and/or murine prekallikrein), but binds to the active form of plasma kallikrein (e.g., human plasma kallikrein and/or murine kallikrein).

In certain embodiments, the antibody binds at or near the active site of the catalytic domain of plasma kallikrein, or a fragment thereof, or binds an epitope that overlaps with the active site of plasma kallikrein.

In some aspects, the antibody binds the same epitope or competes for binding with an antibody described herein.

The antibody can bind to plasma kallikrein, e.g., human plasma kallikrein, with a binding affinity of at least $10^5$, $10^6$, $10^7$, $10^8$, $10^9$, $10^{10}$ and $10^{11}$ $M^{-1}$. In one embodiment, the antibody binds to human plasma kallikrein with a $K_{off}$ slower than $1\times10^{-3}$, $5\times10^{-4}$ $s^{-1}$, or $1\times10^{-4}$ $s^{-1}$. In one embodiment, the antibody binds to human plasma kallikrein with a $K_{on}$ faster than $1\times10^2$, $1\times10^3$, or $5\times10^3$ $M^{-1}$ $s^{-1}$. In one embodiment, the antibody binds to plasma kallikrein, but does not bind to tissue kallikrein and/or plasma prekallikrein (e.g., the antibody binds to tissue kallikrein and/or plasma prekallikrein less effectively (e.g., 5-, 10-, 50-, 100-, or 1000-fold less or not at all, e.g., as compared to a negative control) than it binds to plasma kallikrein.

In one embodiment, the antibody inhibits human plasma kallikrein activity, e.g., with a Ki of less than $10^{-5}$, $10^{-6}$, $10^{-7}$, $10^{-8}$, $10^{-9}$, and $10^{-10}$ M. The antibody can have, for example, an $IC_{50}$ of less than 100 nM, 10 nM, 1, 0.5, or 0.2 nM. For example, the antibody may modulate plasma kallikrein activity, as well as the production of Factor XIIa (e.g., from Factor XII) and/or bradykinin (e.g., from high-molecular-weight kininogen (HMWK)). The antibody may inhibit plasma kallikrein activity, and/or the production of Factor XIIa (e.g., from Factor XII) and/or bradykinin (e.g., from high-molecular-weight kininogen (HMWK)). The affinity of the antibody for human plasma kallikrein can be characterized by a $K_D$ of less than 100 nm, less than 10 nM, less than 5 nM, less than 1 nM, less than 0.5 nM. In one embodiment, the antibody inhibits plasma kallikrein, but does not inhibit tissue kallikrein (e.g., the antibody inhibits tissue kallikrein less effectively (e.g., 5-, 10-, 50-, 100-, or 1000-fold less or not at all, e.g., as compared to a negative control) than it inhibits plasma kallikrein.

In some embodiments, the antibody has an apparent inhibition constant ($K_{i,app}$) of less than 1000, 500, 100, 5, 1, 0.5 or 0.2 nM.

Plasma kallikrein binding antibodies may have their HC and LC variable domain sequences included in a single polypeptide (e.g., scFv), or on different polypeptides (e.g., IgG or Fab).

In one embodiment, the HC and LC variable domain sequences are components of the same polypeptide chain. In another, the HC and LC variable domain sequences are components of different polypeptide chains. For example, the antibody is an IgG, e.g., IgG1, IgG2, IgG3, or IgG4. The antibody can be a soluble Fab. In other implementations the antibody includes a Fab2', scFv, minibody, scFv::Fc fusion, Fab::HSA fusion, HSA::Fab fusion, Fab::HSA::Fab fusion, or other molecule that comprises the antigen combining site of one of the binding proteins herein. The VH and VL regions of these Fabs can be provided as IgG, Fab, Fab2, Fab2', scFv, PEGylated Fab, PEGylated scFv, PEGylated Fab2, VH::CH1::HSA+LC, HSA::VH::CH1+LC, LC:: HSA+VH::CH1, HSA::LC+VH::CH1, or other appropriate construction.

In one embodiment, the antibody is a human or humanized antibody or is non-immunogenic in a human. For example, the antibody includes one or more human antibody framework regions, e.g., all human framework regions, or framework regions at least 85, 88, 89, 90, 91, 92, 93, 94, 95, 96, 97, 98, 99% identical to human framework regions. In one embodiment, the antibody includes a human Fc domain, or an Fc domain that is at least 95, 96, 97, 98, or 99% identical to a human Fc domain.

In one embodiment, the antibody is a primate or primatized antibody or is non-immunogenic in a human. For example, the antibody includes one or more primate antibody framework regions, e.g., all primate framework regions, or framework regions at least 85, 88, 89, 90, 91, 92, 93, 94, 95, 96, 97, 98, 99% identical to primate framework regions. In one embodiment, the antibody includes a primate Fc domain, or an Fc domain that is at least 95, 96, 97, 98, or 99% identical to a primate Fc domain. "Primate" includes humans (*Homo sapiens*), chimpanzees (*Pan troglodytes* and *Pan paniscus* (bonobos)), gorillas (*Gorilla gorilla*), gibbons, monkeys, lemurs, aye-ayes (*Daubentonia madagascariensis*), and tarsiers. In some embodiments, the affinity of the primate antibody for human plasma kallikrein is characterized by a $K_D$ of less than 1000, 500, 100, 10, 5, 1, 0.5 nM, e.g., less than 10 nM, less than 1 nM, or less than 0.5 nM.

In certain embodiments, the antibody includes no sequences from mice or rabbits (e.g., is not a murine or rabbit antibody).

In some embodiments, the antibody used in the methods described herein may be DX-2930 as described herein or a functional variant thereof, or an antibody that binds the same epitope as DX-2930 or competes against DX-2930 for binding to active plasma kallikrein.

In one example, a functional variant of DX-2930 comprises the same complementary determining regions (CDRs) as DX-2930. In another example, the functional variants of DX-2930 may contain one or more mutations (e.g., conservative substitutions) in the FRs of either the $V_H$ or the $V_L$ as compared to those in the $V_H$ and $V_L$ of DX-2930. Preferably, such mutations do not occur at residues which are predicted to interact with one or more of the CDRs, which can be determined by routine technology. In other embodiments, the functional variants described herein contain one or more mutations (e.g., 1, 2, or 3) within one or more of the CDR regions of DX-2930. Preferably, such functional variants retain the same regions/residues responsible for antigen-binding as the parent. In yet other embodiments, a functional variant of DX-2930 may comprise a $V_H$ chain that comprises an amino acid sequence at least 85% (e.g., 90%, 92%, 94%, 95%, 96%, 97%, 98%, or 99%) identical to that of the $V_H$ of DX-2930 and/or a $V_L$ chain that has an amino acid sequence at least 85% (e.g., 90%, 92%, 94%, 95%, 96%, 97%, 98%, or 99%) identical to that of the $V_L$ of DX-2930. These variants are capable of binding to the active form of plasma kallikrein and preferably do not bind to prekallikrein.

The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In some embodiments, the antibody used in the methods and compositions described herein may be the DX-2930 antibody. The heavy and light chain full and variable sequences for DX-2930 are provided below, with signal sequences in italics. The CDRs are boldfaced and underlined.

DX-2930 Heavy Chain Amino Acid Sequence (451 amino acids, 49439.02 Da)
(SEQ ID NO: 1)
*MGWSCILFLVATATGAHS*EVQLLESGGGLVQPGGSLRLSCAASGFTFSHY

IMMWVRQAPGKGLEWVSGIYSSGGITVYADSVKGRFTISRDNSKNTLYLQ

MNSLRAEDTAVYYCAYRRIGVPRRDEFDIWGQGTMVTVSSASTKGPSVFP

LAPSSKSTSGGTAALGCLVKDYFPEPVTVSWNSGALTSGVHTFPAVLQSS

GLYSLSSVVTVPSSSLGTQTYICNVNHKPSNTKVDKRVEPKSCDKTHTCP

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPAPIEKTISKAKGQPREPQVYTLPPSREEMTKNQVSLTCLVKGFYPSDI

AVEWESNGQPENNYKTTPPVLDSDGSFFLYSKLTVDKSRWQQGNVFSCSV

MHEALHNHYTQKSLSLSPG

DX-2930 Light Chain Amino Acid Sequence (213 amino acids, 23419.08 Da)
(SEQ ID NO: 2)
MGWSCILFLVATATGAHSDIQMTQSPSTLSASVGDRVTITCRASQSISSW

LAWYQQKPGKAPKLLIYKASTLESGVPSRFSGSGSGTEFTLTISSLQPDD

CLLNNFYPREAKVQWKVDNALQFATYYCQQYNTYWTFGQGTKVEIKRTVA

APSVFIFPPSDEQLKSGTASVVSGNSQESVTEQDSKDSTYSLSSTLTLSK

ADYEKHKVYACEVTHQGLSSPVTKSFNRGEC

DX-2930 Heavy Chain Variable Domain Amino Acid Sequence
(SEQ ID NO: 3)
EVQLLESGGGLVQPGGSLRLSCAASGFTFSHYIMMWVRQAPGKGLEWVSG
IYSSGGITVYADSVKGRFTISRDNSKNTLYLQMNSLRAEDTAVYYCAYRR
IGVPRRDEFDIWGQGTMVTVSS DX-2930 Light Chain Variable Domain Amino Acid Sequence
(SEQ ID NO: 4)
DIQMTQSPSTLSASVGDRVTITCRASQSISSWLAWYQQKPGKAPKWYKAS
TLESGVPSRFSGSGSGTEFTLTISSLQPDDFATYYCQQYNTYWTFGQGTK
VEIK

TABLE 1

CDRs for DX-2930.

| CDR | Amino acid sequence |
|---|---|
| Heavy chain CDR1 | HYIMM (SEQ ID NO: 5) |
| Heavy chain CDR2 | GIYSSGGITVYADSVKG (SEQ ID NO: 6) |
| Heavy chain CDR3 | RRIGVPRRDEFDI (SEQ ID NO: 7) |
| Light chain CDR1 | RASQSISSWLA (SEQ ID NO: 8) |
| Light chain CDR2 | KASTLES (SEQ ID NO: 9) |
| Light chain CDR3 | QQYNTYWT (SEQ ID NO: 10) |

Antibody Preparation

An antibody as described herein (e.g., DX-2930) can be made by any method known in the art. See, for example, Harlow and Lane, (1988) *Antibodies: A Laboratory Manual*, Cold Spring Harbor Laboratory, New York and Greenfield, (2013) *Antibodies: A Laboratory Manual*, Second edition, Cold Spring Harbor Laboratory Press.

The sequence encoding the antibody of interest, e.g., DX-2930, may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the activity of PKal. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) *Annu. Rev. Immunol.* 12:433-455. Alternatively, the phage display technology (McCafferty et al., (1990) *Nature* 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')$_2$ fragments can be produced by pepsin digestion of an antibody molecule, and Fab fragments that can be generated by reducing the disulfide bridges of F(ab')$_2$ fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated or synthesized. The DNA may be placed into one or more expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) *Proc. Nat. Acad. Sci.* 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) *Proc. Natl. Acad. Sci. USA* 81, 6851; Neuberger et al. (1984) *Nature* 312, 604; and Takeda et al. (1984) *Nature* 314:452.

Methods for constructing humanized antibodies are also well known in the art. See, e.g., Queen et al., *Proc. Natl. Acad. Sci. USA,* 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704, 692) can be adapted to produce a phage or yeast scFv library and scFv clones specific to a PKal can be identified from the library following routine procedures. Positive clones can be subjected to further screening to identify those that inhibits PKal activity.

Some antibodies, e.g., Fabs, can be produced in bacterial cells, e.g., *E. coli* cells (see e.g., Nadkarni, A. et al., 2007 *Protein Expr Purif* 52(1):219-29). For example, if the Fab is encoded by sequences in a phage display vector that includes a suppressible stop codon between the display entity and a bacteriophage protein (or fragment thereof), the vector nucleic acid can be transferred into a bacterial cell that cannot suppress a stop codon. In this case, the Fab is not fused to the gene III protein and is secreted into the periplasm and/or media.

Antibodies can also be produced in eukaryotic cells. In one embodiment, the antibodies (e.g., scFv's) are expressed in a yeast cell such as Pichia (see, e.g., Powers et al., 2001, *J. Immunol. Methods.* 251:123-35; Schoonooghe S. et al., 2009 *BMC Biotechnol.* 9:70; Abdel-Salam, H A. et al., 2001 *Appl Microbiol Biotechnol* 56(1-2):157-64; Takahashi K. et al., 2000 *Biosci Biotechnol Biochem* 64(10):2138-44; Edqvist, J. et al., 1991 *J Biotechnol* 20(3):291-300), *Hanseula*, or *Saccharomyces*. One of skill in the art can optimize antibody production in yeast by optimizing, for example, oxygen conditions (see e.g., Baumann K., et al. 2010 *BMC Syst. Biol.* 4:141), osmolarity (see e.g., Dragosits, M. et al., 2010 *BMC Genomics* 11:207), temperature (see e.g., Dragosits, M. et al., 2009 *J Proteome Res.* 8(3):1380-92), fermentation conditions (see e.g., Ning, D. et al. 2005 *J. Biochem. and Mol. Biol.* 38(3): 294-299), strain of yeast (see e.g., Kozyr, A V et al. 2004 *Mol Biol* (Mosk) 38(6):1067-75; Horwitz, A H. et al., 1988 *Proc Natl Acad Sci USA* 85(22): 8678-82; Bowdish, K. et al. 1991 *J Biol Chem* 266(18): 11901-8), overexpression of proteins to enhance antibody production (see e.g., Gasser, B. et al., 2006 *Biotechol. Bioeng.* 94(2):353-61), level of acidity of the culture (see e.g., Kobayashi H., et al., 1997 *FEMS Microbiol Lett* 152 (2):235-42), concentrations of substrates and/or ions (see e.g., Ko J H. et al., 2996 *Appl Biochem Biotechnol* 60(1): 41-8). In addition, yeast systems can be used to produce antibodies with an extended half-life (see e.g., Smith, B J. et al. 2001 *Bioconjug Chem* 12(5):750-756).

In one preferred embodiment, antibodies are produced in mammalian cells. Preferred mammalian host cells for expressing the clone antibodies or antigen-binding fragments thereof include Chinese Hamster Ovary (CHO cells) (including dhfr− CHO cells, described in Urlaub and Chasin, 1980, *Proc. Natl. Acad. Sci. USA* 77:4216-4220, used with a DHFR selectable marker, e.g., as described in Kaufman and Sharp, 1982, *Mol. Biol.* 159:601 621), lymphocytic cell lines, e.g., NS0 myeloma cells and SP2 cells, COS cells, HEK293T cells (*J. Immunol. Methods* (2004) 289(1-2):65-80), and a cell from a transgenic animal, e.g., a transgenic mammal. For example, the cell is a mammary epithelial cell.

In some embodiments, plasma kallikrein binding antibodies are produced in a plant or cell-free based system (see e.g., Galeffi, P., et al., 2006 *J Transl Med* 4:39).

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

In an exemplary system for recombinant expression of an antibody, or antigen-binding portion thereof, a recombinant expression vector encoding both the antibody heavy chain and the antibody light chain is introduced into dhfr⁻ CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G coupled matrix.

For antibodies that include an Fc domain, the antibody production system may produce antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcg receptors and complement C1q (Burton and Woof, 1992, *Adv. Immunol.* 51:1-84; Jefferis et al., 1998, *Immunol. Rev.* 163:59-76). In one embodiment, the Fc domain is produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

Pharmaceutical Compositions

An antibody as described herein (e.g., DX-2930) can be present in a composition, e.g., a pharmaceutically acceptable composition or pharmaceutical composition. The antibody as described herein (e.g., DX-2930) can be formulated together with a pharmaceutically acceptable carrier. In some embodiments, 150 mg or 300 mg of DX-2930 antibody are present in a composition optionally with a pharmaceutically acceptable carrier, e.g., a pharmaceutically acceptable composition or pharmaceutical composition.

A pharmaceutically acceptable carrier includes any and all solvents, dispersion media, coatings, antibacterial and antifungal agents, isotonic and absorption delaying agents, and the like that are physiologically compatible. Preferably, the carrier is suitable for subcutaneous, intravenous, intramuscular, parenteral, spinal, or epidermal administration (e.g., by injection or infusion), although carriers suitable for inhalation and intranasal administration are also contemplated.

The pharmaceutically acceptable carrier in the pharmaceutical composition described herein may include one or more of a buffering agent, an amino acid, and a tonicity modifier. Any suitable buffering agent or combination of buffering agents may be used in the pharmaceutical composition described herein to maintain or aid in maintaining an appropriate pH of the composition. Non-limiting examples of buffering agents include sodium phosphate, potassium phosphate, citric acid, sodium succinate, histidine, Tris, and sodium acetate. In some embodiments, the buffering agents may be at a concentration of about 5-100 mM, 5-50 mM, 10-50 mM, 15-50 mM, or about 15-40 mM. For example, the one or more buffering agents may be at a concentration of about 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 31 mM, 32 mM, 33 mM, 35 mM, 36 mM, 37 mM, 38 mM, 39 mM, or about 40 mM. In some examples, the pharmaceutically acceptable carrier comprises sodium phosphate and citric acid, which may be at a concentration of about 30 mM and about 19 mM, respectively.

In some embodiments, the pharmaceutically acceptable carrier includes one or more amino acids, which may decrease aggregation of the antibody and/or increase stability of the antibody during storage prior to administration. Exemplary amino acids for use in making the pharmaceutical compositions described herein include, but are not limited to, alanine, arginine, asparagine, aspartic acid, glycine, histidine, lysine, proline, or serine. In some examples, the concentration of the amino acid in the pharmaceutical composition may be about 5-100 mM, 10-90 mM, 20-80 mM, 30-70 mM, 40-60 mM, or about 45-55 mM. In some examples, the concentration of the amino acid (e.g., histidine) may be about 40 mM, 41 mM, 42 mM, 43 mM, 44 mM, 45 mM, 46 mM, 47 mM, 48 mM, 49 mM, 50 mM, 51 mM, 52 mM, 53 mM, 54 mM, 55 mM, 56 mM, 57 mM, 58 mM, 59 mM, or about 60 mM. In one example, the pharmaceutical composition contains histidine at a concentration of about 50 mM.

Any suitable tonicity modifier may be used for preparing the pharmaceutical compositions described herein. In some embodiments, the tonicity modifier is a salt or an amino acid. Examples of suitable salts include, without limitation, sodium chloride, sodium succinate, sodium sulfate, potassium chloride, magnesium chloride, magnesium sulfate, and calcium chloride. In some embodiments, the tonicity modifier in the pharmaceutical composition may be at a concentration of about 10-150 mM, 50-150 mM, 50-100 mM, 75-100 mM, or about 85-95 mM. In some embodiments, the tonicity modifier may be at a concentration of about 80 mM, 81 mM, 82 mM, 83 mM, 84 mM, 85 mM, 86 mM, 87 mM, 88 mM, 89 mM, 90 mM, 91 mM, 92 mM, 93 mM, 94 mM, 95 mM, 96 mM, 97 mM, 98 mM, 99 mM, or about 100 mM. In one example, the tonicity modifier may be sodium chloride, which may be at a concentration of about 90 mM.

The pharmaceutically acceptable carrier in the pharmaceutical compositions described herein may further comprise one or more pharmaceutically acceptable excipients. In general, pharmaceutically acceptable excipients are pharmacologically inactive substances. Non-limiting examples of excipients include lactose, glycerol, xylitol, sorbitol, mannitol, maltose, inositol, trehalose, glucose, bovine serum albumin (BSA), dextran, polyvinyl acetate (PVA), hydroxypropyl methylcellulose (HPMC), polyethyleneimine (PEI), gelatin, polyvinylpyrrolidone (PVP), hydroxyethylcellulose (HEC), polyethylene glycol (PEG), ethylene glycol, glycerol, dimethysulfoxide (DMSO), dimethylformamide (DMF), polyoxyethylene sorbitan monolaurate (Tween-20), polyoxyethylene sorbitan monooleate (Tween-80), sodium dodecyl sulphate (SDS), polysorbate, polyoxyethylene copolymer, potassium phosphate, sodium acetate, ammonium sulfate, magnesium sulfate, sodium sulfate, trimethylamine N-oxide, betaine, zinc ions, copper ions, calcium ions, manganese ions, magnesium ions, CHAPS, sucrose monolaurate and 2-O-beta-mannoglycerate. In some embodiments, the pharmaceutically acceptable carrier comprises an excipient between about 0.001%-0.1%, 0.001%-0.05%, 0.005-0.1%, 0.005%-0.05%, 0.008%-0.05%, 0.008%-0.03% or about 0.009%-0.02%. In some embodiments, the excipient is at about 0.005%, 0.006%, 0.007%, 0.008%, 0.009%, 0.01%, 0.02%, 0.03%, 0.04%, 0.05%, 0.06%, 0.07%, 0.08%, 0.09%, or about 0.1%. In some embodiments, the excipient is polyoxyethylene sorbitan monooleate (Tween-80). In one example, the pharmaceutically acceptable carrier contains 0.01% Tween-80.

In some examples, the pharmaceutical composition described herein comprises the anti-pKal antibody as also described herein (e.g., DX-2930), and one or more of sodium phosphate (e.g., sodium phosphate dibasic dihydrate), citric acid (e.g., citric acid monohydrate), histidine (e.g., L-histidine), sodium chloride, and Polysorbate 80. For example, the pharmaceutical composition may comprise the antibody, sodium phosphate, citric acid, histidine, sodium chloride, and Polysorbate 80. In some examples, the antibody is formulated in about 30 mM sodium phosphate, about 19 mM citric acid, about 50 mM histidine, about 90 mM sodium chloride, and about 0.01% Polysorbate 80. The concentration of the antibody (e.g., DX-2930) in the composition can be about 150 mg/mL or 300 mg/mL. In one example, the composition comprises or consists of about 150 mg DX-2930 per 1 mL solution, about 30 mM sodium phosphate dibasic dihydrate, about 19 mM (e.g., 19.6 mM) citric acid monohydrate, about 50 mM L-histidine, about 90 mM sodium chloride, and about 0.01% Polysorbate 80. In another example, the composition comprises or consists of about 300 mg DX-2930 per 1 mL solution, about 30 mM sodium phosphate dibasic dihydrate, about 19 mM (e.g., 19.6 mM) citric acid monohydrate, about 50 mM L-histidine, about 90 mM sodium chloride, and about 0.01% Polysorbate 80.

A pharmaceutically acceptable salt is a salt that retains the desired biological activity of the compound and does not impart any undesired toxicological effects (see, e.g., Berge, S. M., et al., 1977, *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids, and the like. Base addition salts include those derived from alkaline earth metals, such as sodium, potassium, magnesium, calcium, and the like, as well as from nontoxic organic amines, such as N,N'-dibenzylethylenediamine, N-methylglucamine, chloroprocaine, choline, diethanolamine, ethylenediamine, procaine, and the like.

The compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Many compositions are in the form of injectable or infusible solutions, such as compositions similar to those used for administration of humans with antibodies. An exemplary mode of administration is parenteral (e.g., intravenous, subcutaneous, intraperitoneal, intramuscular). In one embodiment, the plasma kallikrein binding protein is administered by intravenous infusion or injection. In another embodiment, the plasma kallikrein binding protein is administered by intramuscular injection. In another embodiment, the plasma kallikrein binding protein is administered by subcutaneous injection. In another preferred embodiment, the plasma kallikrein binding protein is administered by intraperitoneal injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In some embodiments, the antibody is administered subcutaneously.

The composition can be formulated as a solution, microemulsion, dispersion, liposome, or other ordered structure suitable to high drug concentration. Sterile injectable solutions can be prepared by incorporating the binding protein in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An antibody as described herein (e.g., DX-2930) can be administered by a variety of methods, including intravenous injection, subcutaneous injection, or infusion. For example, for some therapeutic applications, the antibody can be administered by intravenous infusion at a rate of less than 30, 20, 10, 5, or 1 mg/min to reach a dose of about 1 to 100 mg/m$^2$ or 7 to 25 mg/m$^2$. The route and/or mode of administration will vary depending upon the desired results. In certain embodiments, the active compound may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are available. See, e.g., Sustained and Controlled Release Drug Delivery Systems, J. R. Robinson, ed., 1978, Marcel Dekker, Inc., New York.

Pharmaceutical compositions can be administered with medical devices. For example, in one embodiment, a pharmaceutical composition disclosed herein can be administered with a device, e.g., a needleless hypodermic injection device, a pump, or implant.

In certain embodiments, an antibody as described herein (e.g., DX-2930) can be formulated to ensure proper distribution in vivo. For example, the blood-brain barrier (BBB) excludes many highly hydrophilic compounds. To ensure that the therapeutic compounds disclosed herein cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., V. V. Ranade, 1989, J. Clin. Pharmacol. 29:685).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms can be dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody as described herein (e.g., DX-2930) is about 150 mg or 300 mg. As will be understood by one of ordinary skill in the art, a therapeutically or prophylactically effective amount of an antibody may be lower for a pediatric subject than for an adult subject. In some embodiments, the effective amount that is administered to a pediatric subject is a fixed dose or a weight based dose. In some embodiments, effective amount that is less than about 150 mg or 300 mg is administered to a pediatric subject. In some embodiments, a therapeutically or prophylactically effective amount of an antibody is administered every two weeks or every four weeks for a first treatment period. In some embodiments, the antibody may be administered to the subject for a second treatment period. In some embodiments, the therapeutically or prophylactically effective amount of the antibody in the first treatment period is different than the therapeutically or prophylactically effective amount of the antibody in the second treatment period. In some embodiments, the therapeutically or prophylactically effective amount of the antibody in the first treatment period is 150 mg and the therapeutically or prophylactically effective amount of the antibody in the second treatment period is 300 mg. In some embodiments, the therapeutically or prophylactically effective amount of the antibody in the first treatment period is the same as the therapeutically or prophylactically effective amount of the antibody in the second treatment period. In one example, therapeutically or prophylactically effective amount of the antibody in the first treatment period and the second treatment period is 300 mg.

In some embodiments, an exemplary, non-limiting range for a therapeutically or prophylactically effective amount of an antibody as described herein (e.g., DX-2930) is about 300 mg. In some embodiments, a therapeutically or prophylactically effective amount of an antibody is administered in a single dose. If the subject experiences a HAE attack, the antibody may be further administered to the subject in multiple doses, such in doses of about 300 mg administered every two weeks.

Kits

An antibody as described herein (e.g., DX-2930) can be provided in a kit, e.g., as a component of a kit. For example, the kit includes (a) a DX-2930 antibody, e.g., a composition (e.g., a pharmaceutical composition) that includes the antibody, and, optionally (b) informational material. The informational material can be descriptive, instructional, marketing or other material that relates to a method described herein and/or the use of an antibody as described herein (e.g., DX-2930), e.g., for a method described herein. In some embodiments, the kit comprises one or more doses of DX-2930. In some embodiments, the one or more doses are 150 mg or 300 mg.

The informational material of the kit is not limited in its form. In one embodiment, the informational material can include information about production of the compound, molecular weight of the compound, concentration, date of expiration, batch or production site information, and so forth. In one embodiment, the informational material relates to using the antibody to treat, prevent, or diagnosis of disorders and conditions, e.g., a plasma kallikrein associated disease or condition.

In one embodiment, the informational material can include instructions to administer an antibody as described herein (e.g., DX-2930) in a suitable manner to perform the methods described herein, e.g., in a suitable dose, dosage form, mode of administration or dosing schedule (e.g., a dose, dosage form, dosing schedule or mode of administration described herein). In another embodiment, the informational material can include instructions to administer an antibody as described herein (e.g., DX-2930) to a suitable subject, e.g., a human, e.g., a human having, or at risk for, a plasma kallikrein associated disease or condition. For example, the material can include instructions to administer an antibody as described herein (e.g., DX-2930) to a patient with a disorder or condition described herein, e.g., a plasma kallikrein associated disease, e.g., according to a dosing schedule described herein. The informational material of the kits is not limited in its form. In many cases, the informational material, e.g., instructions, is provided in print but may also be in other formats, such as computer readable material.

An antibody as described herein (e.g., DX-2930) can be provided in any form, e.g., liquid, dried or lyophilized form. It is preferred that an antibody be substantially pure and/or sterile. When an antibody is provided in a liquid solution, the liquid solution preferably is an aqueous solution, with a sterile aqueous solution being preferred. When an antibody is provided as a dried form, reconstitution generally is by the addition of a suitable solvent. The solvent, e.g., sterile water or buffer, can optionally be provided in the kit.

The kit can include one or more containers for the composition containing an antibody as described herein (e.g., DX-2930). In some embodiments, the kit contains separate containers, dividers or compartments for the composition and informational material. For example, the composition can be contained in a bottle, vial, or syringe, and the informational material can be contained in association with the container. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of an antibody as described herein (e.g., DX-2930). For example, the kit includes a plurality of syringes, ampules, foil packets, or blister packs, each containing a single unit dose of an antibody as described herein (e.g., DX-2930). The containers of the kits can be air tight, waterproof (e.g., impermeable to changes in moisture or evaporation), and/or light-tight.

The kit optionally includes a device suitable for administration of the composition, e.g., a syringe, or any such delivery device. In one embodiment, the device is an implantable device that dispenses metered doses of the antibody. The disclosure also features a method of providing a kit, e.g., by combining components described herein.

Treatment

In some aspects, the disclosure provides the use of an antibody as described herein (e.g., DX-2930) in treating HAE.

(i) Hereditary Angioedema

Hereditary angioedema (HAE) is also known as "Quincke edema," C1 esterase inhibitor deficiency, C1 inhibitor deficiency, and hereditary angioneurotic edema (HANE). HAE is characterized by unpredictable, recurrent attacks of severe subcutaneous or submucosal swelling (angioedema), which can affect, e.g., the limbs, face, genitals, gastrointestinal tract, and airway (Zuraw, 2008). Symptoms of HAE include, e.g., swelling in the arms, legs, lips, eyes, tongue, and/or throat; airway blockage that can involve throat swelling, sudden hoarseness and/or cause death from asphyxiation (Bork et al., 2012; Bork et al., 2000). Approximately 50% of all HAE patients will experience a laryngeal attack in their lifetime, and there is no way to predict which patients are at risk of a laryngeal attack (Bork et al., 2003; Bork et al., 2006). HAE symptoms also include repeat episodes of abdominal cramping without obvious cause; and/or swelling of the intestines, which can be severe and can lead to abdominal cramping, vomiting, dehydration, diarrhea, pain, shock, and/or intestinal symptoms resembling abdominal emergencies, which may lead to unnecessary surgery (Zuraw, 2008). Swelling may last up to five or more days. About one-third of individuals with this HAE develop a non-itchy rash called erythema marginatum during an attack. Most patients suffer multiple attacks per year.

HAE is an orphan disorder, the exact prevalence of which is unknown, but current estimates range from 1 per 10,000 to 1 per 150,000 persons, with many authors agreeing that 1 per 50,000 is likely the closest estimate (Bygum, 2009; Goring et al., 1998; Lei et al., 2011; Nordenfelt et al., 2014; Roche et al., 2005).

Plasma kallikrein plays a critical role in the pathogenesis of HAE attacks (Davis, 2006; Kaplan and Joseph, 2010). In normal physiology, C1-INH regulates the activity of plasma kallikrein as well as a variety of other proteases, such as C1r, C1s, factor XIa, and factor XIIa. Plasma kallikrein regulates the release of bradykinin from high molecular weight kininogen (HMWK). Due to a deficiency of C1-INH in HAE, uncontrolled plasma kallikrein activity occurs and leads to the excessive generation of bradykinin. Bradykinin is a vasodilator which is thought to be responsible for the characteristic HAE symptoms of localized swelling, inflammation, and pain (Craig et al., 2012; Zuraw et al., 2013).

Swelling of the airway can be life threatening and causes death in some patients. Mortality rates are estimated at 15-33%. HAE leads to about 15,000-30,000 emergency department visits per year.

Trauma or stress, e.g., dental procedures, sickness (e.g., viral illnesses such as colds and the flu), menstruation, and surgery can trigger an attack of angioedema. To prevent acute attacks of HAE, patients can attempt to avoid specific stimuli that have previously caused attacks. However, in many cases, an attack occurs without a known trigger. Typically, HAE symptoms first appear in childhood and worsen during puberty. On average, untreated individuals have an attack every 1 to 2 weeks, and most episodes last for about 3 to 4 days (ghr.nlm.nih.gov/condition/hereditary-angioedema). The frequency and duration of attacks vary greatly among people with hereditary angioedema, even among people in the same family.

There are three types of HAE, known as types I, II, and III, all of which can be treated by the methods described herein. It is estimated that HAE affects 1 in 50,000 people, that type I accounts for about 85 percent of cases, type II accounts for about 15 percent of cases, and type III is very rare. Type III is the most newly described form and was originally thought to occur only in women, but families with affected males have been identified.

HAE is inherited in an autosomal dominant pattern, such that an affected person can inherit the mutation from one affected parent. New mutations in the gene can also occur, and thus HAE can also occur in people with no history of the disorder in their family. It is estimated that 20-25% of cases result from a new spontaneous mutation.

Mutations in the SERPING1 gene cause hereditary angioedema type I and type II. The SERPING1 gene provides instructions for making the C1 inhibitor protein, which is important for controlling inflammation. C1 inhibitor blocks the activity of certain proteins that promote inflammation. Mutations that cause hereditary angioedema type I lead to reduced levels of C1 inhibitor in the blood. In contrast, mutations that cause type II result in the production of a C1 inhibitor that functions abnormally. Approximately 85% of patients have Type I HAE, characterized by very low production of functionally normal C1-INH protein, while the remaining approximately 15% of patients have Type II HAE and produce normal or elevated levels of a functionally impaired C1-INH (Zuraw, 2008). Without the proper levels of functional C1 inhibitor, excessive amounts of bradykinin are generated from high molecular weight kininogen (HMWK), and there is increased vascular leakage mediated by bradykinin binding to the B2 receptor (B2-R) on the surface of endothelial cells (Zuraw, 2008). Bradykinin promotes inflammation by increasing the leakage of fluid through the walls of blood vessels into body tissues. Excessive accumulation of fluids in body tissues causes the episodes of swelling seen in individuals with hereditary angioedema type I and type II.

Mutations in the F12 gene are associated with some cases of hereditary angioedema type III. The F12 gene provides instructions for making coagulation factor XII. In addition to playing a critical role in blood clotting (coagulation), factor XII is also an important stimulator of inflammation and is involved in the production of bradykinin. Certain mutations in the F12 gene result in the production of factor XII with increased activity. As a result, more bradykinin is generated and blood vessel walls become more leaky, which leads to episodes of swelling. The cause of other cases of hereditary angioedema type III remains unknown. Mutations in one or more as-yet unidentified genes may be responsible for the disorder in these cases.

HAE can present similarly to other forms of angioedema resulting from allergies or other medical conditions, but it differs significantly in cause and treatment. When hereditary angioedema is misdiagnosed as an allergy, it is most commonly treated with antihistamines, steroids, and/or epinephrine, which are typically ineffective in HAE, although epinephrine can be used for life-threatening reactions. Misdiagnoses have also resulted in unnecessary exploratory surgery for patients with abdominal swelling, and in some HAE patients abdominal pain has been incorrectly diagnosed as psychosomatic.

Like adults, children with HAE can suffer from recurrent and debilitating attacks. Symptoms may present very early in childhood, and upper airway angioedema has been reported in HAE patients as young as the age of 3 (Bork et al., 2003). In one case study of 49 pediatric HAE patients, 23 had suffered at least one episode of airway angioedema by the age of 18 (Farkas, 2010). An important unmet medical need exists among children with HAE, especially adolescents, since the disease commonly worsens after puberty (Bennett and Craig, 2015; Zuraw, 2008).

C1 inhibitor therapies, as well as other therapies for HAE, are described in Kaplan, A. P., *J Allergy Clin Immunol*, 2010, 126(5):918-925.

Acute treatment of HAE attacks is provided to halt progression of the edema as quickly as possible. C1 inhibitor concentrate from donor blood, which is administered intravenously, is one acute treatment; however, this treatment is not available in many countries. In emergency situations where C1 inhibitor concentrate is not available, fresh frozen plasma (FFP) can be used as an alternative, as it also contains C1 inhibitor.

Purified C1 inhibitor, derived from human blood, has been used in Europe since 1979. Several C1 inhibitor treatments are now available in the U.S. and two C1 inhibitor products are now available in Canada. Berinert P (CSL Behring), which is pasteurized, was approved by the F.D.A. in 2009 for acute attacks. Cinryze (ViroPharma), which is nanofiltered, was approved by the F.D.A. in 2008 for prophylaxis. Rhucin (Pharming) is a recombinant C1 inhibitor under development that does not carry the risk of infectious disease transmission due to human blood-borne pathogens.

Treatment of an acute HAE attack also can include medications for pain relief and/or IV fluids.

Other treatment modalities can stimulate the synthesis of C1 inhibitor, or reduce C1 inhibitor consumption. Androgen medications, such as danazol, can reduce the frequency and severity of attacks by stimulating production of C1 inhibitor.

*Helicobacter pylori* can trigger abdominal attacks. Antibiotics to treat *H. pylori* will decrease abdominal attacks.

Newer treatments attack the contact cascade. Ecallantide (KALBITOR®, DX-88, Dyax) inhibits plasma kallikrein and has been approved in the U.S. Icatibant (FIRAZYR®, Shire) inhibits the bradykinin B2 receptor, and has been approved in Europe and the U.S.

Diagnosis of HAE can rely on, e.g., family history and/or blood tests. Laboratory findings associated with HAE types I, II, and III are described, e.g., in Kaplan, A. P., *J Allergy Clin Immunol*, 2010, 126(5):918-925. In type I HAE, the level of C1 inhibitor is decreased, as is the level of C4, whereas C1q level is normal. In type II HAE, the level of C1 inhibitor is normal or increased; however, C1 inhibitor function is abnormal. C4 level is decreased and C1q level is normal. In type III, the levels of C1 inhibitor, C4, and C1q can all be normal.

Symptoms of HAE can be assessed, for example, using questionnaires, e.g., questionnaires that are completed by patients, clinicians, or family members. Such questionnaires are known in the art and include, for example, visual analog scales. See, e.g., McMillan, C. V. et al. *Patient*. 2012; 5(2):113-26. In some embodiments, the subject has HAE type I or HAE type II. HAE type I or HAE type II may be diagnosed using any method known in the art, such as by clinical history consistent with HAE (e.g., subcutaneous or mucosal, nonpruritic swelling episodes) or diagnostic testing (e.g., C1-INH functional testing and C4 level assessment).

(ii) Treating HAE with anti-PKal Antibodies

The disclosure provides methods of treating (e.g., ameliorating, stabilizing, or eliminating one or more symptoms) of hereditary angioedema (HAE) by administering an antibody described herein (e.g., a therapeutically effective amount of an antibody described herein) to a subject having or suspected of having HAE, e.g., according to a dosing schedule described herein. Additionally provided are methods of treating HAE by administering an antibody described herein (e.g., a therapeutically effective amount of an antibody described herein), e.g., according to a dosing schedule described herein, or in combination with a second therapy, e.g., with one other agent, e.g., described herein. The disclosure also provides methods of preventing HAE or a symptom thereof by administering an antibody described herein (e.g., a prophylactically effective amount of an antibody described herein) to a subject at risk of developing HAE (e.g., a subject having a family member with HAE or a genetic predisposition thereto), e.g., according to a dosing schedule described herein. In some examples, the subject may be a human patient who has no HAE symptoms at the time of the treatment. In some embodiments, the subject is a human patient that has HAE type I or HAE type II. In some embodiments, the subject is a human patient that has experienced at least two (e.g., 2, 3, 4, 5 or more) HAE attacks in the year prior to the treatment.

Treating includes administering an amount effective to alleviate, relieve, alter, remedy, ameliorate, improve or affect the disorder, the symptoms of the disorder or the predisposition toward the disorder. The treatment may also delay onset, e.g., prevent onset, or prevent deterioration of a disease or condition.

Methods of administering DX-2930 antibodies are also described in "Pharmaceutical Compositions." Suitable dosages of the antibody used can depend on the age and weight of the subject and the particular drug used. The antibody can be used as competitive agents to inhibit, reduce an undesirable interaction, e.g., between plasma kallikrein and its substrate (e.g., Factor XII or HMWK). The dose of the antibody can be the amount sufficient to block 90%, 91%, 92%, 93%, 94%, 95%, 96%, 97%, 98% 99%, or 99.9% of the activity of plasma kallikrein in the patient, especially at the site of disease. In some embodiments, 150 mg or 300 mg of the antibody is administered every two weeks or every four weeks. In some embodiments, 300 mg of the antibody is administered in a single dose. If the subject experiences an HAE attack after the single dose, the antibody may be administered at 300 mg every two weeks.

In one embodiment, the antibodies are used to inhibit an activity (e.g., inhibit at least one activity of plasma kallikrein, e.g., reduce Factor XIIa and/or bradykinin production) of plasma kallikrein, e.g., in vivo. The binding proteins can be used by themselves or conjugated to an agent, e.g., a cytotoxic drug, cytotoxin enzyme, or radioisotope.

The antibodies can be used directly in vivo to eliminate antigen-expressing cells via natural complement-dependent cytotoxicity (CDC) or antibody dependent cellular cytotoxicity (ADCC). The antibodies described herein can include complement binding effector domain, such as the Fc portions from IgG1, -2, or -3 or corresponding portions of IgM which bind complement. In one embodiment, a population of target cells is ex vivo treated with an antibody described herein and appropriate effector cells. The treatment can be supplemented by the addition of complement or serum containing complement. Further, phagocytosis of target cells coated with an antibody described herein can be improved by binding of complement proteins. In another embodiment target, cells coated with the antibody which includes a complement binding effector domain are lysed by complement.

Methods of administering DX-2930 antibodies are described in "Pharmaceutical Compositions." Suitable dosages of the molecules used will depend on the age and weight of the subject and the particular drug used. The antibodies can be used as competitive agents to inhibit or reduce an undesirable interaction, e.g., between a natural or pathological agent and the plasma kallikrein.

A therapeutically effective amount of an antibody as described herein, can be administered to a subject having, suspected of having, or at risk for HAE, thereby treating (e.g., ameliorating or improving a symptom or feature of a disorder, slowing, stabilizing and/or halting disease progression) the disorder.

The antibody described herein can be administered in a therapeutically effective amount. A therapeutically effective amount of an antibody is the amount which is effective, upon single or multiple dose administration to a subject, in treating a subject, e.g., curing, alleviating, relieving or improving at least one symptom of a disorder in a subject to a degree beyond that expected in the absence of such treatment.

Dosage regimens can be adjusted to provide the optimum desired response (e.g., a therapeutic response). For example, a single bolus may be administered, several divided doses may be administered over time or the dose may be proportionally reduced or increased as indicated by the exigencies of the therapeutic situation. In other examples, a bolus may be administered followed by several doses over time or the dose may be proportionally reduced or increased as indicated by the exigencies of the therapeutic situation. In other examples, a dose may be divided into several doses and be administered over time. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

In some embodiments, an antibody as described herein is administered in a dosage regimen during a first treatment period. In some embodiments, the antibody is administered in the first treatment period in multiple doses. In this period, the therapeutically or prophylactically effective amount of the antibody (e.g., DX-2930) can be about 150 mg or 300 mg and is administered every week, every two weeks, every three weeks, every four weeks, every five weeks, every six weeks, every seven weeks, every eight weeks or longer. In some embodiments, the therapeutically or prophylactically effective amount of the antibody (e.g., DX-2930) can be about 150 mg or 300 mg and is administered every two weeks or every four weeks. In some embodiments, the therapeutically or prophylactically effective amount is administered at least two times, at least three times, at least four times, at least five times, at least six times, at least seven times, at least eight times, at least nine times, at least ten times, at least eleven times, at least twelve time, at least thirteen times, or more. In some embodiments, the first treatment period is 26 weeks. In some embodiments, the therapeutically or prophylactically effective amount is 150 mg and is administered to the subject every four weeks (e.g., every four weeks for 26 weeks, resulting in delivery of 7 doses total). In some embodiments, the therapeutically or prophylactically effective amount is 300 mg and is administered to the subject every two weeks (e.g., every two weeks for 26 weeks, resulting in delivery of 13 doses total).

In one example, the first treatment period is 26 weeks and the antibody is administered on day 0, day 28, day 56, day 84, day 112, day 140, and day 168. In another example, the first treatment period is 26 weeks and the antibody is administered on day 0, day 14, day 28, day 42, day 56, day 70, day 84, day 98, day 112, day 126, day 140, day 154, and day 168. It would have been understood by those skilled in the art that the listed treatment schedule allows for a ±4 day (e.g., ±3 days, ±2 days, or ±1 day) window. For example, a dose given at day 10-18 would be encompassed by the dose of day 14 noted above.

In some embodiments, a therapeutically or prophylactically effective amount is administered in a dosage regimen during a second treatment period following the first treatment period. In some embodiments, the therapeutically or prophylactically effective amount is different in the first treatment period and the second treatment period. In some embodiments, the therapeutically or prophylactically effective amount for the second treatment period is about 300 mg. During this period, the antibody may be administered in multiple doses of about 300 mg, such as 300 mg administered every two weeks. In some embodiments, in the second treatment period, the multiple doses of the antibody are administered at least two times, at least three times, at least four times, at least five times, at least six times, at least seven times, at least eight times, at least nine times, at least ten times, at least eleven times, at least twelve time, at least thirteen times. In some embodiments, the second treatment period is 26 weeks. In some embodiments, the antibody is administered at a dose of about 300 mg every two weeks for 26 weeks (e.g. resulting in delivery of 13 doses). In some embodiments, the single first dose of the second treatment period is administered about two weeks after the last dose of the first treatment period.

In any of the embodiments described herein, the timing of the administration of the antibody is approximate and may include the three days prior to and three days following the indicated day (e.g., administration every two weeks encompasses administration on day 11, day 12, day 13, day 14, day 15, day 16, or day 17).

In some embodiments, an antibody as described herein is administered in a single dose of about 300 mg to a subject who has undergone a prior HAE treatment (a first treatment), such as a multi-dose treatment with the same anti-pKal antibody as described herein (e.g., DX-2930). If the subject experiences a HAE attack after the single dose, the subject can be treated by the antibody for multiple doses at about 300 mg every two weeks for a suitable period, for example, 26 weeks. In some embodiments, the first of the multiple doses is administered within one week of the HAE attack (e.g., within 1 day, 2, days, 3 days, 4 days, 5 days, 6 days, or 7 days of the HAE attack). In some embodiments, the antibody is administered at least two times, at least three times, at least four times, at least five times, at least six times, at least seven times, at least eight times, at least nine times, at least ten times, at least eleven times, at least twelve time, at least thirteen times, or more.

The prior HAE treatment can involve the same antibody as described herein (e.g., DX-2930). In some embodiments, the prior HAE treatment may involve multiple doses of DX-2930 every two weeks or every four weeks. In some embodiments, DX-2930 is given to the subject (e.g., subcutaneously) at 150 mg every two weeks, at 300 mg every two weeks, or at 300 mg every four weeks. In one example, the subject was previously administered the antibody every two weeks or four weeks for 26 weeks prior to administration of the single dose of the antibody. In some embodiments, the multiple doses of the antibody of the prior treatment are administered at least two times, at least three times, at least four times, at least five times, at least six times, at least seven times, at least eight times, at least nine times, at least ten times, at least eleven times, at least twelve time, at least thirteen times. In some embodiments, the antibody was previously administered to the day 0, day 28, day 56, day 84, day 112, day 140, and day 168. In some embodiments, the single dose of about 300 mg of the antibody is administered about two weeks after the last dose of the previous treatment. In one example, the single dose of the second treatment period is administered on day 182 of the first treatment period.

In any of the embodiments described herein, the timing of the administration of the antibody is approximate and includes the three days prior to and three days following the indicated day (e.g., administration every two weeks encompasses administration on day 11, day 12, day 13, day 14, day 15, day 16, or day 17).

In some embodiments, prior to administering an antibody according to any of the methods described herein, the subject may be evaluated to establish a baseline rate of HAE attacks. Such an evaluation period may be referred to as a "run-in period." In some embodiments, the baseline rate of HAE attacks must meet or exceed a minimum number of HAE attacks in a given time period. In one example, the subject experiences at least one HAE attack in a four week run-in period prior to the first administration of the antibody. In another example, the subject experiences at least two HAE attacks in an eight week run-in period prior to the first administration of the antibody.

Any of the subjects described herein may have undergone prior treatment of HAE, such as a prophylactic or therapeutic treatment of HAE. Aspects of the present disclosure also provide methods of administering an antibody as described herein (e.g., DX-2930) to a subject that has received one or more prior treatment for HAE. In some embodiments, the prior treatment of HAE is a treatment that involves an antibody described herein (e.g., DX-2930). In some embodiments, the subject was previously administered multiple doses of DX-2930 every two weeks or every four weeks. In some embodiments, the subject was previously administered DX-2930 at 150 mg every two weeks. In some embodiments, the subject was previously administered DX-2930 at 300 mg every two weeks. In some embodiments, the subject was previously administered DX-2930 at 300 mg every four weeks. In some embodiments, the multiple doses of the antibody of the prior treatment are administered at least two times, at least three times, at least four times, at least five times, at least six times, at least seven times, at least eight times, at least nine times, at least ten times, at least eleven times, at least twelve time, at least thirteen times.

In some embodiments, the subject has received one or more prior treatment for HAE, which may involve any of the therapeutic agent for HAE known in the art. Exemplary anti-HAE agents include, but are not limited to, C1-inhibitors (e.g., Cinryze®, Berinert®, or Ruconest®), plasma kallikrein inhibitors (e.g., Kalbitor®), bradykinin receptor inhibitors (e.g., Firazyr®), annenuated androgens (e.g., danazol), and anti-fibrinolytics (e.g., traexamic acid). In some examples, a subject may undergo a tapering period before receiving the anti-pKal antibody treatment as described herein. A tapering period refers to a period, prior to the anti-pKal antibody treatment, during which a subject who is on an anti-HAE treatment (e.g., C1-INH, oral androgen, and/or oral anti-fibrinolytics) gradually reduces the dosage, frequency, or both of the anti-HAE agent such that the subject can gradually transit from the prior HAE treatment to the anti-pKal antibody treatment as described herein. In some embodiments, the tapering involving a gradual or step-wise method of reducing the dosage of the prior treatment and/or the frequency with which the prior treatment is administered. The tapering period may last 2-4 weeks and can vary based on factors of an individual patent. In some examples, the prior treatment terminates before the anti-pKal antibody treatment starts. In other examples, the prior treatment may terminate within a suitable timeframe (e.g., 2 weeks, 3 weeks, or 4 weeks) after the subject is given his or her first dose of the anti-pKal antibody.

Alternatively, a subject who is on a prior HAE treatment may be transitioned to the anti-pKal antibody treatment as described herein directly without the tapering period.

In other embodiments, the subject is free of any prior treatment of HAE before the first treatment, first treatment period, and/or the follow-on single and multiple dose treatments as described herein (the second treatment period). In some embodiments, the subject is free of any treatment other than with the antibodies described herein during the first treatment period and/or during the second treatment period. In some embodiments, the subject is free of any prior treatment of HAE for at least two weeks (e.g., at least two, three, four, five weeks or more) before the first treatment or first treatment period, during the first treatment or first treatment period, and/or during the second treatment period. In some embodiments, the subject is free of long-term prophylaxis for HAE (e.g., C1 inhibitor, attenuated androgens, anti-fibrinolytics) for at least the two weeks prior to the first treatment or first treatment period, during the first treatment period, and/or during the second treatment period. In some embodiments, the subject is free of an HAE treatment involving an angiotensin-converting enzyme (ACE) inhibitor for at least the four weeks prior to the first treatment or first treatment period, during the first treatment period, and/or during the second treatment period. In some embodiments, the subject is free of an estrogen-containing medication for at least the four weeks prior to the first treatment or first treatment period, during the first treatment period, and/or during the second treatment period. In some embodiments, the subject is free of androgens (e.g. stanozolol, danazol, oxandrolone, methyltestosterone, testosterone) for at least the two weeks prior to the first treatment or first treatment period, during the first treatment period and/or during the second treatment period.

Any of the methods described herein may further comprise monitoring the patient for side effects (e.g., elevation of creatine phosphatase levels) and/or inhibition levels of pKal by the antibody (e.g., serum or plasma concentration of the antibody or the pKal activity level) before and after the treatment or during the course of treatment. If one or more adverse effect is observed, the dose of the antibody might be reduced or the treatment might be terminated. If the inhibition level is below a minimum therapeutic level, further doses of the antibody might be administered to the patient. Patients may also be evaluated for the generation of antibody against the administered antibody; activity of C1-inhibitor, C4, and/or C1q; quality of life; incidence of any HAE attacks, health-related quality of life, anxiety and/or depression (e.g., Hospital Anxiety and Depression Scale (HADS)), work productivity (e.g., Work Productivity and Activity Impairment Questionnaire (WPAI)), preference of the subcutaneous administration of the antibody (e.g., D-2930) relative to other injectables, quality of life (e.g, angioedema-quality of life (AE-QOL), EuroQoL Group 5-dimension report).

In some embodiments, the plasma or serum concentration of the antibody (e.g., DX-2930) may be measured during the course of the treatment (e.g., after the initial dosage) for assessing the efficacy of the treatment. If the plasma or serum concentration of the antibody is lower than about 80 nM, a follow-up dosage may be needed, which may be the same or higher than the initial dosage. The plasma or serum concentration of the antibody may be measured by determining the protein level of the antibody in a plasma or serum sample obtained from the subject, e.g., by an immune assay or MS assay. The plasma or serum concentration of the antibody may also be measured by determining the inhibitory level of pKal in a plasma or serum sample obtained from a subject treated with the antibody. Such assays may include the synthetic substrate assay or the Western blot assay for measuring cleaved kininogen as described herein.

Alternatively or in addition, the plasma or serum level of creatine kinase and/or one or more coagulation parameters (e.g., activated partial thromboplastin time (aPTT), prothrombin time (PT), bleeding events) can be monitored during the course of the treatment. If the plasma or serum level of creatine kinase is found to elevate during the treatment, the dosage of the antibody may be reduced or the treatment may be terminated. Similarly, if one or more coagulation parameters are found to be significantly affected during the treatment, the dosage of the antibody may be modified or the treatment may be terminated.

In some embodiments, an optimal dosage (e.g., optimal prophylactic dosage or optimal therapeutic dosage) of the antibody (e.g., DX-2930) may be determined as follows. The antibody is given to a subject in need of the treatment at an initial dose. The plasma concentration of the antibody in the subject is measured. If the plasma concentration is lower than 80 nM, the dose of the antibody is increased in a subsequent administration. A dosage of the antibody that maintains the antibody plasma concentration above about 80 nM can be chosen as the optimal dosage for the subject. The creatine phosphokinase level of the subject can be monitored during the course of treatment and the optimal dosage for that subject can be further adjusted based on the creatine phosphokinase level, e.g., the dosage of the antibody might be reduced if elevation of creatine phosphokinase is observed during treatment.

(iii) Combination Therapies

An antibody as described herein (e.g., DX-2930) can be administered in combination with one or more of the other therapies for treating a disease or condition associated with plasma kallikrein activity, e.g., a disease or condition described herein. For example, an antibody as described herein (e.g., DX-2930) can be used therapeutically or prophylactically (e.g., before, during, or after the course of treatment) with another anti-plasma kallikrein Fab or IgG (e.g., another Fab or IgG described herein), another plasma kallikrein inhibitor, a peptide inhibitor, small molecule inhibitor, or surgery. Examples of plasma kallikrein inhibitors that can be used in combination therapy with a plasma kallikrein binding antibodies described herein include plasma kallikrein inhibitors described in, e.g., WO 95/21601 or WO 2003/103475.

One or more plasma kallikrein inhibitors can be used in combination with an antibody as described herein (e.g., DX-2930). For example, the combination can result in a lower dose of the inhibitor being needed, such that side effects are reduced.

An antibody as described herein (e.g., DX-2930) can be administered in combination with one or more current therapies for treating HAE. For example, DX-2930 antibody can be co-used with a second anti-HAE therapeutic agent such as ecallantide, a C1 esterase inhibitor (e.g., CINRYZE™), aprotinin (TRASYLOL®), and/or a bradykinin B2 receptor inhibitor (e.g., icatibant (FIRAZYR®)).

The term "combination" refers to the use of the two or more agents or therapies to treat the same patient, wherein the use or action of the agents or therapies overlaps in time. The agents or therapies can be administered at the same time (e.g., as a single formulation that is administered to a patient or as two separate formulations administered concurrently) or sequentially in any order. Sequential administrations are administrations that are given at different times. The time between administration of the one agent and another agent can be minutes, hours, days, or weeks. The use of a plasma kallikrein binding antibody described herein can also be used to reduce the dosage of another therapy, e.g., to reduce the side effects associated with another agent that is being administered. Accordingly, a combination can include administering a second agent at a dosage at least 10, 20, 30, or 50% lower than would be used in the absence of the plasma kallikrein binding antibody. In some embodiments, a subject can be given a C1-inhibitor as a loading IV dose or SC dose simultaneously with the first dose of an anti-pKal antibody (e.g., DX-2930) as described herein. The subject can then continue with the anti-pKal antibody treatment (without further doses of the C1-inhibitor).

A combination therapy can include administering an agent that reduces the side effects of other therapies. The agent can be an agent that reduces the side effects of a plasma kallikrein associated disease treatment.

(iv) Assays for Assessing a Treatment Regimen

Also within the scope of the present disclosure are assay methods for assessing efficacy of any of the treatment methods described herein. In some embodiments, the plasma or serum concentration of one or more biomarkers (e.g., 2-chain HMWK) associated with HAE may be may be measured prior to and/or during the course of the treatment (e.g., after the initial dosage) for assessing the efficacy of the treatment. In some embodiments, the plasma or serum concentration (level) of one or more biomarkers associated with HAE obtained at a time point after administration of a dosage is compared to the concentration of the biomarker in a sample obtained at an earlier time point after administration of a dosage or prior to administration of the initial dosage. In some embodiments, the biomarker is 2-HMWK.

The level of the biomarker may be measured by detecting the biomarker in a plasma or serum sample obtained from the subject, e.g., by an immunoassay, such as Western blot assay or ELISA, using an antibody that specifically detects the biomarker. In some embodiments, the level of 2-HWMK in a plasma or serum sample obtained from the subject is assessed by an immunoassay. Antibodies for use in immunoassays for the detection of 2-HWMK are known in the art and selection of such an antibody for use in the methods described herein will be evident to one of ordinary skill in the art.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

A Double-Blind Study to Assess Efficacy and Safety of DX-2930 Using Multiple Doses Study Overview A phase 3, multicenter, randomized, double-blind, placebo-controlled trial is described to evaluate the efficacy and safety of DX-2930 in preventing acute attacks in patients with Type I and Type II HAE. This double-blind study may be followed by a subsequent treatment period. In general, subjects aged 12 and over with a documented diagnosis of Type I or Type II HAE who experience at least 1 attack per 4 weeks during the run-in period are included.

Long-Term Prophylactic (LTP) Therapy Washout

Following informed consent, subjects are subjected to screening assessments. Screened subjects who are on long-term prophylactic therapy for HAE are required to undergo a minimum 2 week washout period prior to the start of the run-in period. The LTP washout is permitted as long as the investigator determines that doing so would not place the subject at any undue safety risk and the subject is at least 18 years of age. These criteria ensure that patients who should remain on LTP do not washout for this study, but do allow the enrollment of appropriate patients with severe disease while minimizing their time off LTP. Current treatment guidelines recognize two different standard of care approaches to treating HAE, which include LTP and on-demand therapy (Cicardi et al., 2012; Craig et al., 2012; Zuraw et al., 2013). Throughout the study, subjects are permitted to treat acute HAE attacks. Thus, those subjects who stop LTP in order to enter the study and are subsequently randomized to the placebo group are still managed with no reduction in their standard of care. Confirmation that the subject has successfully completed the 2 week washout period is required before they can enter the run-in period.

Run-In Period

Screened subjects who are either not on long-term prophylactic therapy for HAE or have completed the required washout period are subjected to a run-in period of 4 weeks to determine the baseline HAE attack rate. Only subjects meeting a minimum baseline rate of at least 1 confirmed HAE attack per 4 weeks are eligible for enrollment and randomization. Subjects who experience 3 or more confirmed attacks before the end of the 4 weeks can exit the run-in period early and proceed to enrollment and randomization. Subjects without at least 1 confirmed attack after 4 weeks of run-in have their run-in period extended for another 4 weeks, during which time they need to have at least 2 confirmed attacks to proceed to enrollment and randomization.

To be eligible for enrollment, subjects who have their run-in extended must complete the full 8-week run-in period prior to entering the treatment period. Subjects who do not meet the minimum attack rate during run-in or are otherwise determined to be ineligible due to screening assessments are considered a screen fail and are not allowed to rescreen into the study.

Treatment Period

After verification of eligibility, subjects are randomized 2:1 to receive repeated subcutaneous (SC) administrations of DX-2930 or placebo in a double-blind fashion. Subjects who are randomized to DX-2930 are assigned in a 1:1:1 ratio to one of three dose regimens: 300 mg every 2 weeks, 300 mg every 4 weeks or 150 mg every 4 weeks. Randomization into all treatment groups is blocked by naïve vs. non-naïve subjects (subjects receiving active study drug in protocol DX-2930-02) as well as the baseline attack rate observed during the run-in period into the following groups: 1 to <2 attacks per 4 weeks, 2 to <3 attacks per 4 weeks, and ≥3 attacks per 4 weeks.

Each subject is subjected to a treatment period consisting of 13 doses of blinded Investigational Medicinal Product (IMP), for a period of 26 weeks from the date of first dose on Day 0 through two weeks after the final dose. Subjects randomized to one of the 4 treatment arms receive either a DX-2930 or placebo dose according to the dosing schedule in Table 2.

TABLE 2

Treatment period dosing schedule

| Treatment Period | | Treatment Arms: DX-2930 or Placebo | | | |
| --- | --- | --- | --- | --- | --- |
| Dose Number | Dose Day/Week | 300 mg every 2 weeks | 300 mg every 4 weeks | 150 mg every 4 weeks | Placebo |
| 1 | Day 0/Week 0 | DX-2930 | DX-2930 | DX-2930 | Placebo |
| 2 | Day 14/Week 2 | DX-2930 | Placebo | Placebo | Placebo |
| 3 | Day 28/Week 4 | DX-2930 | DX-2930 | DX-2930 | Placebo |
| 4 | Day 42/Week 6 | DX-2930 | Placebo | Placebo | Placebo |
| 5 | Day 56/Week 8 | DX-2930 | DX-2930 | DX-2930 | Placebo |
| 6 | Day 70/Week 10 | DX-2930 | Placebo | Placebo | Placebo |
| 7 | Day 84/Week 12 | DX-2930 | DX-2930 | DX-2930 | Placebo |
| 8 | Day 98/Week 14 | DX-2930 | Placebo | Placebo | Placebo |
| 9 | Day 112/Week 16 | DX-2930 | DX-2930 | DX-2930 | Placebo |
| 10 | Day 126/Week 18 | DX-2930 | Placebo | Placebo | Placebo |
| 11 | Day 140/Week 20 | DX-2930 | DX-2930 | DX-2930 | Placebo |
| 12 | Day 154/Week 22 | DX-2930 | Placebo | Placebo | Placebo |
| 13 | Day 168/Week 24 | DX-2930 | DX-2930 | DX-2930 | Placebo |
|  | Day 182/Week 26 | No Dose | No Dose | No Dose | No Dose |

Description of Treatments
DX-2930

DX-2930 is a sterile, preservative-free solution for injection, pH 6.0. The active ingredient, DX-2930, is formulated using the following compendial components: 30 mM sodium phosphate dibasic dihydrate, 19.6 mM citric acid monohydrate, 50 mM L-histidine, 90 mM sodium chloride, 0.01% Polysorbate 80. Each vial contains a nominal concentration of 150 mg DX-2930 active ingredient in 1 mL solution. The test product is administered by subcutaneous injection into the upper arm in a blinded manner.

For each 300 mg dose of DX-2930, each subject receives a total of 2 mL, divided into 2 separate 1.0 mL SC injections of DX-2930. The 2 injections are given in the same upper arm, with at least 2 cm separation between each injection site. For each 150 mg dose of DX-2930, each subject receives a total of 2 mL, divided into 2 separate 1.0 mL subcutaneous injections, where one injection is DX-2930 and the other is placebo. The 2 injections are given in the same upper arm, with at least 2 cm separation between each injection site.

Placebo

Placebo consists of the inactive formulation of the test product: 30 mM sodium phosphate dibasic dihydrate, 19.6 mM citric acid monohydrate, 50 mM L-histidine, 90 mM sodium chloride, pH 6.0 with 0.01% Polysorbate 80. Placebo doses are administered to subjects randomized to the placebo treatment arm and in between doses of DX-2930 for subjects randomized to the 300 mg or 150 mg DX-2930 every 4 weeks treatment arms, according to the dosing schedule in Table 1.

For each placebo dose, each subject receives a total of 2 mL, divided into 2 separate 1.0 mL subcutaneous injections of placebo. The 2 injections are given in the same upper arm, with at least 2 cm separation between each injection site.

Follow-Up Period

Subjects may further undergo safety and additional evaluations (i.e., pharmacokinetic and pharmacodynamics evaluations) during an 8 week follow-up period. Subjects (or caregivers) are instructed to inform the site of any HAE attack they experience after the final follow-up visit.

Stopping Rules

If it is determined at any time that a dose group must be dropped due to an important safety signal, the remaining unenrolled subjects may be re-randomized into the remaining lower DX-2930 dosing arm(s) or placebo and continue enrollment for the remainder of the study in a double-blind fashion. Data for these subjects is used up to the time at which it is decided to drop the dose in the efficacy analyses and in its entirety in the safety analyses.

Dosing for any individual subject is discontinued if the subject experiences a DX-2930-related severe adverse effect (or a DX-2930-related, clinically significant non-serious adverse effect) that, in the assessment of the investigator, warrants discontinuation from further dosing for that subject's well-being. The investigator has the ability to contact and consult with the medical monitor on such matters. The subject is followed through the completion of all scheduled visits, unless it is requested that they be discontinued from the study. Subjects who are discontinued from further dosing will not be eligible to participate in the open label extension (OLE).

Study Population

The study enrolls up to 120 subjects to provide 108 completed subjects. Subjects are 12 years of age and older with a confirmed diagnosis of HAE (Type I or II) who experience at least 1 confirmed attack per 4 weeks during the run-in period. The study aims to enroll at least 5 subjects who are 12 to 17 years of age. HAE diagnosis is confirmed through documented clinical history consistent with HAE and diagnostic testing conducted either prior to or during the screening visit.

Subject Inclusion Criteria

Patients who meet the following criteria are subject to the treatment described herein:

1. Males and females 12 years of age or older at the time of screening.
2. Documented diagnosis of HAE (Type I or II) based upon all of the following:
   Documented clinical history consistent with HAE (subcutaneous or mucosal, nonpruritic swelling episodes without accompanying urticaria)
   Diagnostic testing results obtained during screening that confirm HAE Type I or II: C1 inhibitor (C1-INH) functional level <40% of the normal level. Subjects with functional C1-INH level 40-50% of the normal level may be enrolled if they also have a C4 level below the normal range. Subjects may begin participating in the run-in period before these diagnostic results are available. Subjects may be retested if results are incongruent with clinical history or believed by to be confounded by recent LTP use.
   At least one of the following: age at reported onset of first angioedema symptoms ≤30 years, a family history consistent with HAE Type I or II, or C1q within normal range.
3. Experiencing a baseline rate of at least 1 Investigator-confirmed HAE attack per 4 weeks as confirmed during the run-in period.
4. Adult subjects and caregivers of subjects under the age of 18 are willing and able to read, understand, and sign an informed consent form. Subjects age 12 to 17, whose caregiver provides informed consent, are willing and able to read, understand and sign an assent form.
5. Males and females who are fertile and sexually active must adhere to contraception requirements for the duration of the study as follows:
   Females of childbearing potential must agree to be abstinent or it is recommended to use highly effective forms of contraception from screening through 30 days after the final study visit. This includes progestin-only oral contraceptive associated with inhibition of ovulation (oral, injectable or implantable), intrauterine device (IUD, all types) or intrauterine hormone releasing systems (IUS). A female whose male partner has had a vasectomy must agree to use one additional form of medically acceptable contraception. Use of a male condom with or without spermicide or cervical cap, diaphragm or sponge with spermicide or a combination (double-barrier methods) is not considered highly effective.
   Females of non-childbearing potential, defined as surgically sterile (status post hysterectomy, bilateral oophorectomy, or bilateral tubal ligation) or postmenopausal for at least 12 months do not require contraception during the study.
   Males, including males who are surgically sterile (post vasectomy), with female partners of childbearing potential must agree to be abstinent or else use a medically acceptable form of contraception from screening through 60 days after the final study visit.

Subject Exclusion Criteria

Patients having one or more of the following criteria may be excluded from the treatment described herein:

1. Concomitant diagnosis of another form of chronic, recurrent angioedema, such as acquired angioedema (AAE), HAE with normal C1-INH (also known as HAE Type III), idiopathic angioedema, or recurrent angioedema associated with urticaria.
2. Dosing with an investigational drug or exposure to an investigational device within 4 weeks prior screening.
3. Exposure to angiotensin-converting enzyme (ACE) inhibitors or any estrogen-containing medications with systemic absorption (such as oral contraceptives or hormonal replacement therapy) within 4 weeks prior to screening.
4. Exposure to androgens (e.g. stanozolol, danazol, oxandrolone, methyltestosterone, testosterone) within 2 weeks prior to entering the run-in period.
5. Use of long-term prophylactic therapy for HAE (C1-INH, attenuated androgens, or anti-fibrinolytics) within 2 weeks prior to entering the run-in period.
6. Use of short-term prophylaxis for HAE within 7 days prior to entering the run-in period. Short-term prophylaxis is defined as C1-INH, attenuated androgens, or anti-fibrinolytics used to avoid angioedema complications from medically indicated procedures.
7. Any of the following liver function test abnormalities: alanine aminotransferase (ALT)>3× upper limit of normal, or aspartate aminotransferase (AST)>3× upper limit of normal, or total bilirubin>2× upper limit of normal (unless the bilirubin elevation is a result of Gilbert's syndrome).
8. Pregnancy or breastfeeding.
9. Subject has any condition that may be considered to compromise their safety or compliance, preclude successful conduct of the study, or interfere with interpretation of the results (e.g., history of substance abuse or dependence, significant pre-existing illness or other major comorbidity that the Investigator considers may confound the interpretation of study results).

Primary and Secondary Endpoints

The following primary and secondary efficacy endpoints are evaluated from Day 14 through Day 182:

The primary endpoint of the study is the number of HAE attacks.

Secondary endpoints include, in rank order:
1. Number of HAE attacks requiring acute treatment
2. Number of moderate to severe HAE attacks Exploratory Efficacy Endpoints
1. Time to first attack after day 14, i.e., duration that a subject is attack-free after day 14 until their first attack.
2. Number per week of high-morbidity HAE attacks; a high-morbidity HAE attack is defined as any attack that has at least one of the following characteristics: severe, results in hospitalization (except hospitalization for observation <24 hours), hemodynamically significant (systolic blood pressure <90, requires IV hydration, or associated with syncope or near-syncope) or laryngeal.

Clinical Laboratory Tests

Subjects involved in the clinical study are subjected to laboratory testing including general safety parameters (hematology, coagulation, urinalysis, and serum chemistry), serology, pregnancy tests, C1-INH functional assay, C4 assay, C1q assay, PK samples, plasma anti-drug antibody testing, and PD samples. All laboratory tests is performed using established and validated methods.

Example 2

A Open-Label Study to Assess Efficacy and Safety of DX-2930

Study Overview

A phase 3, multicenter, randomized, open-label, extension trial is described to evaluate the efficacy and safety of DX-2930, an investigational medicinal product (IMP), in preventing acute angioedema attacks in patients with Type I and Type II HAE who have undergone prior HAE treatment involving DX-2930. This study generally follows a prior HAE treatment regimen that involved multiple doses of about 150 mg or 300 mg of DX-2930 every four weeks or 300 mg DX-2930 every two weeks. In general, subjects (rollover patients, for example those who have been treated with DX-2930 following the regimen disclosed in Example 1, or non-rollover patients, for example, those who have never been treated with DX-2930) aged 12 and over with a documented diagnosis of Type I or Type II HAE, and prior to treatment with DX-2930 who experience at least 1 attack per 4 weeks during a run-in period are included.

The subjects for this study are 12 years of age and older with a confirmed diagnosis of HAE (Type I or II) who experienced at least 1 confirmed attack per 4 weeks prior to the previous HAE treatment involving DX-2930. HAE diagnosis is confirmed through documented clinical history consistent with HAE and diagnostic testing conducted either prior to or during the screening visit.

Treatment Period (i) Rollover Subjects

Each rollover subject (e.g., human patients who have been treated with DX-2930 following the treatment regimens described herein, e.g., in Example 1 above) receive a single open-label dose of 300 mg DX-2930 administered subcutaneously (SC) on Day 0. The subjects will not receive any additional DX-2930 doses until their first reported, and investigator-confirmed, HAE attack. The duration of time between the first open-label dose and first reported HAE attack varies by rollover subject. Until a rollover subject reports their first HAE attack, they are scheduled study visits where the following tests and assessments are performed must be: pregnancy testing, clinical laboratory testing, physical examination, 12-Lead ECG, QoL, PK, PD and anti-drug antibody sample collection.

Once a rollover subject reports his or her first HAE attack, the subject is present to the investigative site for the second open-label dose of DX-2930 as quickly as subject and site schedules allow. At the visit in which the second open-label dose of DX-2930 is administered, the subject undergoes pre-dose assessments for vital signs, physical examination, clinical laboratory testing, and blood sampling for PK, PD, and anti-drug antibody assessments. Vital signs are obtained at 1 hour post-dosing.

Regardless of when a rollover subject's first HAE attack occurs, there will be a minimum of 10 days between their first open-label dose and their second open-label dose. Following their second dose, rollover subjects will continue to receive repeated SC administrations of open-label 300 mg DX-2930 every 2 weeks for the remaining duration of the treatment period per the scheduled dosing. The treatment period lasts 350 days from the date of the first open-label dose. The number of doses administered during this period varies by subject based on the date of each subject's second dose, but will not exceed 26 doses.

(ii) Non-Rollover Subjects

Once all screening assessments have been completed and eligibility confirmed, non-rollover subjects arrive at the study site and, following pre-dose assessments, receive an open-label dose of 300 mg DX-2930 administered SC on Day 0. Non-rollover subjects continues to receive SC administrations of open-label 300 mg DX-2930 every 2 weeks throughout the duration of the treatment period per the scheduled dosing. A total of 26 doses are administered with the last dose administered at the Day 350 study visit.

(iii) All Subjects:

All doses (with the exception of the second dose for rollover subjects) require a minimum of 10 days and maximum of 18 days between administrations, and should fall within the accepted ±4 day window around study visits. If a subject experiences an acute angioedema attack at any time during the study that in the opinion of the investigator requires medical intervention, standard of care therapy should be provided based on subject's medical history and per locally approved product information.

Administration of DX-2930 and study procedures continues without alteration to the protocol study activities schedule, even if a subject receives treatment for a breakthrough angioedema attack on the day of a scheduled dose of study drug (if self-administering) or scheduled study visit.

(iv) Duration of Treatment:

All subjects receive open-label DX-2930 during a 350 day treatment period. The number of doses that rollover subjects receive during this period varies by subject but will not exceed 26 doses. The last dose of open-label DX-2930 administered to these subjects may be given at the Day 350 study visit.

Non-rollover subjects receives 300 mg DX-2930 every 2 weeks for a total of 26 doses, with the first dose administered on Day 0 and the final dose administered at the Day 350 study visit.

There is a ±4-day window around each study visit. There is a minimum of 10 days between any two doses. Excluding the interval between the first and second open-label doses for rollover subjects, there is a maximum of 18 days between any two doses. Subjects are monitored at the study site through 1 hour post-dose for scheduled study site visits. No monitoring of vital signs are performed for subjects who elect to self-administer away from the investigational site.

Test Product; Dose; and Mode of Administration:

DX-2930 (DX-2930) is a sterile, preservative-free solution for injection, pH 6.0. The active ingredient, DX-2930, is formulated using the following compendial components: 30 mM sodium phosphate dibasic dihydrate, 19.6 mM citric acid (e.g., citric acid monohydrate), 50 mM histidine (e.g., L-histidine), 90 mM sodium chloride, 0.01% Polysorbate 80. Each vial contained a nominal concentration of 150 mg DX-2930 active ingredient in 1 mL solution. The test product is administered by subcutaneous injection into the upper arm in a blinded manner.

For each 300 mg dose of DX-2930, each subject received a total of 2 mL, divided into 2 separate 1.0 mL SC injections of DX-2930. The 2 injections were given in the same upper arm, with at least 2 cm separation between each injection site.

For each 150 mg dose of DX-2930, each subject received a total of 2 mL, divided into 2 separate 1.0 mL SC injections, where one injection was DX-2930 and the other was placebo. The 2 injections were given in the same upper arm, with at least 2 cm separation between each injection site.

DX-2930 can be self-administered without supervision (parental supervision required for adolescent subject) after subjects receive appropriate training by the investigator or designee and their understanding is confirmed. Subjects are allowed to initiate self-administration after receiving the first 2 doses of DX-2930 at the study site and may continue to self-administer all subsequent doses. See also descriptions herein.

Follow-Up Period

Subjects are subjected to safety and additional evaluations (i.e., pharmacokinetic and pharmacodynamics evaluations) during an 8 week follow-up period. Subjects (or caregivers)

are instructed to inform the site of any HAE attack they experience after the final follow-up visit.

Stopping Rules

If it is determined at any time that the dose has an important safety signal, any of the doses of DX-2930 may be reduced. Dosing for any individual subject is discontinued if the subject experiences a DX-2930-related severe adverse effect (or a DX-2930-related, clinically significant non-serious adverse effect) that warrants discontinuation from further dosing for that subject's well-being.

Subject Inclusion Criteria

Patients who meet the following criteria are subject to the treatment described herein:

1. Males and females 12 years of age or older at the time of screening.
2. Documented diagnosis of HAE (Type I or II) based upon all of the following:
   Documented clinical history consistent with HAE (subcutaneous or mucosal, nonpruritic swelling episodes without accompanying urticaria)
   Diagnostic testing results obtained during screening that confirm HAE Type I or II: C1 inhibitor (C1-INH) functional level<40% of the normal level. Subjects with functional C1-INH level 40-50% of the normal level may be enrolled if they also have a C4 level below the normal range. Subjects may begin participating in the run-in period before these diagnostic results are available. Subjects may be retested if results are incongruent with clinical history or believed by to be confounded by recent LTP use.
   At least one of the following: age at reported onset of first angioedema symptoms≤30 years, a family history consistent with HAE Type I or II, or C1q within normal range.
3. Experiencing a baseline rate of at least 1 Investigator-confirmed HAE attack per 4 weeks as confirmed during the run-in period.
4. Adult subjects and caregivers of subjects under the age of 18 are willing and able to read, understand, and sign an informed consent form. Subjects age 12 to 17, whose caregiver provides informed consent, are willing and able to read, understand and sign an assent form.
5. Males and females who are fertile and sexually active must adhere to contraception requirements for the duration of the study as follows:
   Females of childbearing potential must have agreed to be abstinent or must have used a highly effective form of contraception from screening through 30 days after the final study visit. This included stable doses, for 3 months prior to study screening, of combined estrogen and progestin-containing hormonal contraception associated with inhibition of ovulation (oral, injectable or implantable), progestin-only hormonal contraception associated with inhibition of ovulation, intra-uterine device (IUD, all types) or intrauterine hormone releasing systems (IUS). It should be noted that a female whose male partner had had a vasectomy must have agreed to use one additional form of medically acceptable contraception. Also, the use of a male condom with or without spermicide or cervical cap, diaphragm or sponge with spermicide or a combination (double barrier methods) were not considered highly effective.
   Females of non-childbearing potential, defined as surgically sterile (status post hysterectomy, bilateral oophorectomy, or bilateral tubal ligation) or post-menopausal for at least 12 months do not require contraception during the study.
   Males, including males who are surgically sterile (post vasectomy), with female partners of childbearing potential must agree to be abstinent or else use a medically acceptable form of contraception from screening through 60 days after the final study visit.

Subject Exclusion Criteria

Patients having one or more of the following criteria may be excluded from the treatment described herein:

1. Concomitant diagnosis of another form of chronic, recurrent angioedema, such as acquired angioedema (AAE), HAE with normal C1-INH (also known as HAE Type III), idiopathic angioedema, or recurrent angioedema associated with urticaria.
2. Dosing with an investigational drug (other than DX-2930 or other HAE therapies) or exposure to an investigational device within 4 weeks prior screening.
3. Exposure to angiotensin-converting enzyme (ACE) inhibitors or any estrogen-containing medications with systemic absorption (such as oral contraceptives or hormonal replacement therapy) within 4 weeks prior to screening.
4. Any of the following liver function test abnormalities: alanine aminotransferase (ALT)>3× upper limit of normal, or aspartate aminotransferase (AST)>3× upper limit of normal, or total bilirubin>2× upper limit of normal (unless the bilirubin elevation is a result of Gilbert's syndrome).
5. Pregnancy or breastfeeding.
6. Subject has any condition that may be considered to compromise their safety or compliance, preclude successful conduct of the study, or interfere with interpretation of the results (e.g., history of substance abuse or dependence, significant pre-existing illness or other major comorbidity that the Investigator considers may confound the interpretation of study results).

Prohibited Concomitant Treatments

Use of the following treatments will not be permitted during the study:
   Long-term prophylaxis (LTP) for HAE (e.g., use of C1-INH for long-term prophylaxis, attenuated androgens, or anti-fibrinolytics) once LTP is discontinued (within 3 weeks following the first does of DX-2930).
   Angiotensin-converting enzyme (ACE) inhibitors.
   Estrogen-containing medications with systemic absorption (such as oral contraceptives or hormonal replacement therapy).
   Use of androgens (e.g., stanozolol, danazol, oxandrolone, methyltestosterone, testosterone) for non-HAE related medical conditions or for HAE after discontinuation during the first three weeks.
   Any other investigational drug or device.

Clinical Laboratory Tests

Subjects involved in the clinical study will undergo laboratory testing including general safety parameters (hematology, coagulation, urinalysis, and serum chemistry), serology, pregnancy tests, C1-INH functional assay, C4 assay, C1q assay, PK samples, PD samples, and plasma anti-drug antibody testing. All laboratory tests will be performed using established and validated methods.

Self-Administration

All subjects (adolescent or adult) who are considered suitable candidates (i.e., those with a physical and mental capability of learning and willing to be trained) are allowed to self administer treatment. Subjects must have completed appropriate training by the investigator or designee and understanding of the training must be confirmed by the investigator or designee.

Subjects are allowed to initiate self-administration after receiving the first 2 doses of DX-2930 at the study site. Once initiated, subjects are allowed to self-administer subsequent doses of DX-2930 at the investigational site (when visits were scheduled study site visits) or the subject's home or other agreed upon location (when the study permitted off-site dosing). Adolescent subjects self-administering investigational product are supervised by a parent/legal guardian/caregiver. Alternatively, a parent/legal guardian/caregiver, after completing appropriate training, is allowed to administer DX-2930 to an adolescent without study site personnel supervision. Site personnel called subjects after the planned off-site self administrations to ensure the administration occurred, to collect adverse events (AEs), concomitant medications, and to ensure all attacks have been appropriately documented.

Efficacy Assessments:

Additional criteria for efficacy endpoints included:

Time to first HAE attack for rollover subjects (based upon time from first open label study dose until first HAE attack)

Number of investigator confirmed HAE attacks during the treatment period

Number of investigator confirmed HAE attacks requiring acute treatment during the treatment period Number of moderate or severe HAE attacks during the treatment period Number of high-morbidity HAE attacks during the treatment period; a high-morbidity HAE attack is defined as any attack that has at least one of the following characteristics: severe, results in hospitalization (except hospitalization for observation<24 hours), hemodynamically significant (systolic blood pressure<90, requires IV hydration, or associated with syncope or near-syncope) or laryngeal.

Additional measures included:
Anti-drug antibody development
Pharmacokinetics (PK)
Pharmacodynamic (PD) effects
Quality of Life Assessments
DX-2930 Injection Report
DX-2930 Self-administration and Subcutaneous Injection Survey Example 3

Assessment of HMWK Following DX-2930 Treatment

HAE patients were randomized into groups receiving the active drug (DX-2930), including different dosage groups (30 mg, 100 mg, 300 mg, and 400 mg) and a group receiving a placebo, and administered subcutaneous doses of the placebo or DX-2930 (DX-2930). Plasma samples were collected at time points from prior to receiving the dose ("pre-dose") and following administration on days 8, 22, 50, 64, 92, and 120.

The plasma samples were subjected to biomarker assays to evaluate the pharmacodynamic activity of DX-2930 in patient plasma. In particular, the samples were evaluated for the presence of 2-chain HMWK in an assay using an antibody that specifically binds to 2-chain HMWK.

Figure 3:
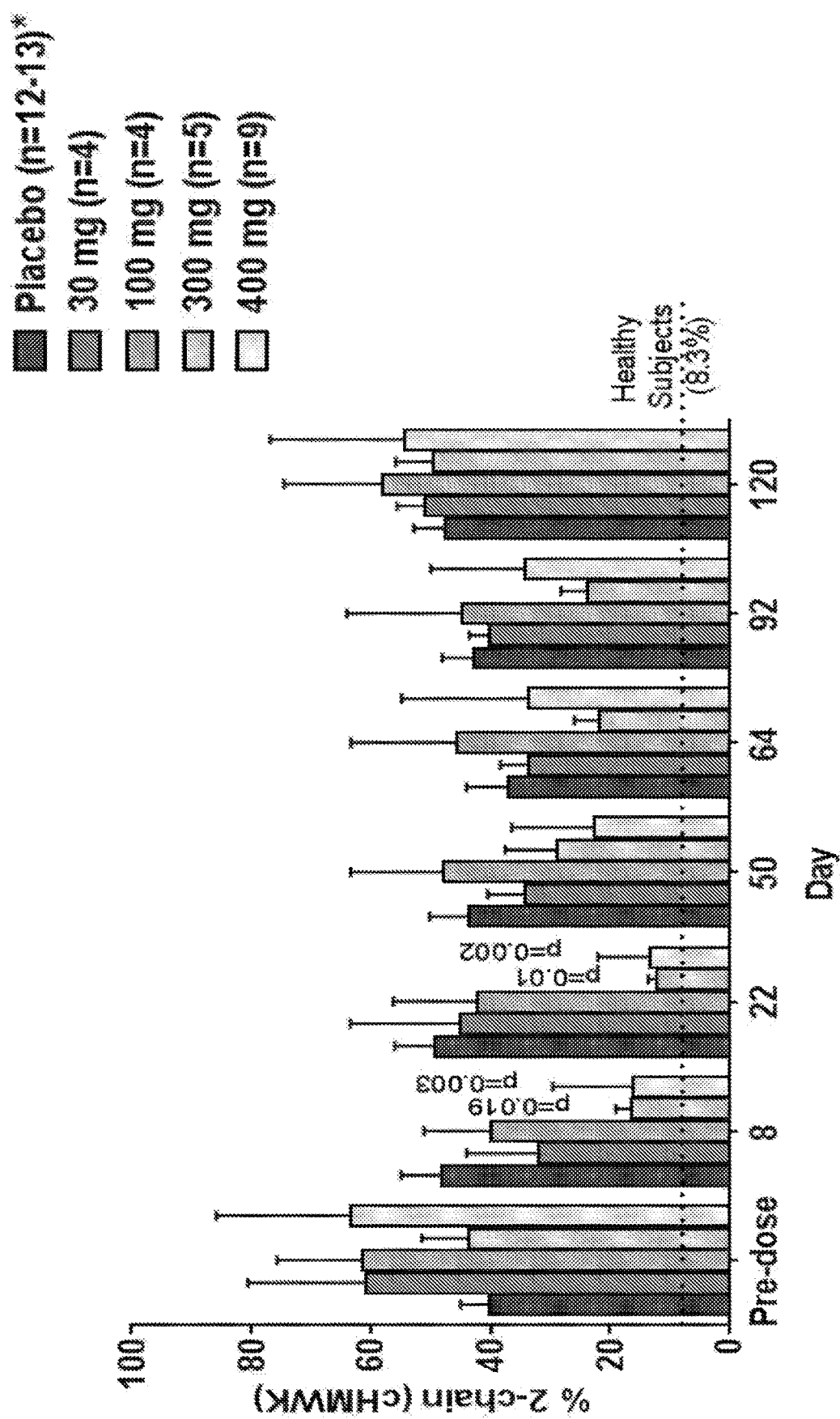
FIG. 3 shows 2-chain high-molecular-weight kininogen (HMWK) in plasma samples from HAE patients treated with DX-2930 on the indicated days at the indicated doses (30 mg, 100 mg, 300 mg, or 400 mg) as detected by Western blot analysis. The baseline of 2-chain HMWK detected in health subjects is indicated with a dotted line. For each day, the columns correspond to, from left to right, placebo, 30 mg, 100 mg, 300 mg, and 400 mg.

As shown in FIG. 3, administration of DX-2930 led to a reduction in the level 2-chain HMWK in patients that receive DX-2930, for example, 300 mg or 400 mg of DX-2930. Two-chain HMWK levels in these subjects approached the levels of 2-chain HMWK detected in healthy subjects at 8 and 22 days following administration and were still reduced at least at day 92 following administration.

These results indicate that administration with DX-2930 reduced levels of 2-chain HMWK (a biomarker for evaluating plasma kallikrein instability and the stabilizing effect of Dx-2930), which could be detected for several months following administration. 2-chain HMWK is also used as a biomarker to evaluate plasma kallikrein Other Embodiments All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

Equivalents

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of examples only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of", or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for treating hereditary angioedema (HAE) attack or reducing the rate of HAE attack, the method comprising:
   (i) administering to a subject in need thereof an antibody at a single dose of about 300 mg, wherein the antibody comprises a heavy chain complementarity determining region (HCDR) 1 set forth as HYIMM (SEQ ID NO: 5), a HCDR2 set forth as GIYSSGGITVYADSVKG (SEQ ID NO: 6), a HCDR3 set forth as RRIGVPRRDEFDI (SEQ ID NO: 7) and light chain complementarity determining region (LCDR) 1 set forth as RASQSISSWLA (SEQ ID NO: 8), a LCDR2 set forth as KASTLES (SEQ ID NO: 9), and a LCDR3 set forth as QQYNTYWT (SEQ ID NO: 10), and wherein the subject has undergone a first HAE treatment comprising administering the antibody to the subject in multiple doses of about 300 mg every two weeks; and
   (ii) further administering to the subject the antibody in one or more doses of about 300 mg, after the subject experiences an HAE attack after (i).

2. The method of claim 1, wherein in step (ii), the subject is administered multiple doses of the antibody at about 300 mg every two weeks.

3. The method of claim 1, wherein the first dose of step (ii) is within one week after the HAE attack; and/or wherein the single dose of (i) and the first dose of (ii) are at least 10 days apart.

4. The method of claim 1, wherein the antibody comprises a heavy chain variable domain set forth as EVQLLESGG-GLVQPGGSLRLSCAASGFTFSHYIMMWVRQAPGK-GLEWVSGIYSSGGITV YADSVKGRFTISRDNSKNT-LYLQMNSLRAEDTAVYYCAYRRIGVPRRDEFDIWGQ GTM VTVSS (SEQ ID NO: 3) and a light chain variable domain set forth as DIQMTQSPSTLSASVGDRVTIT-CRASQSISS-WLAWYQQKPGKAPKLLIYKASTLESGVPS RFSGSGSGTEFTLTISSLQPDDFA-TYYCQQYNTYWTFGQGTKVEIK (SEQ ID NO: 4).

5. The method of claim 1, wherein the antibody is a full length antibody or an antigen-binding fragment thereof.

6. The method of claim 5, wherein the antibody is an IgG molecule.

7. The method of claim 6, wherein the antibody is an IgG1 molecule.

8. The method of claim 5, wherein the antibody comprises a heavy chain set forth as SEQ ID NO: 1 and a light chain set forth as SEQ ID NO: 2.

9. The method of claim 1, wherein the antibody is formulated in a pharmaceutical composition comprising sodium phosphate, citric acid, histidine, sodium chloride, and polysorbate 80.

10. The method of claim 9, wherein the antibody is formulated in about 30 mM sodium phosphate, about 19 mM citric acid, about 50 mM histidine, about 90 mM sodium chloride, and about 0.01% polysorbate 80.

11. The method of claim 1, wherein the antibody is administered subcutaneously.

12. The method of claim 1, wherein the subject:
   (i) is a human patient having, suspected of having, or at risk for HAE;
   (ii) is a human patient having HAE type I or type II;
   (iii) is a human patient who had experienced at least two HAE attacks per year prior to the first HAE treatment; and/or
   (iv) is a human patient who has received one or more prior HAE treatments prior to the first HAE treatment.

13. The method of claim 12, wherein the prior HAE treatment comprises a C1-inhibitor (C1-INH), a plasma kallikrein inhibitor, a bradykinin receptor antagonist, an androgen, an anti-tranexamic acid, or a combination thereof.

14. The method of claim 13, wherein the prior HAE comprises a C1-INH, ecallantide, icatibant, danazol, tranexamic acid, or a combination thereof.

15. The method of claim 12, wherein the subject has undergone a tapering period for the one or more prior HAE treatments.

16. The method of claim 15, wherein the tapering period is about 2-4 weeks.

17. The method of claim 12, wherein the one or more prior HAE treatments terminate either before the first dose of the antibody in the first HAE treatment or within three weeks after the first dose of the antibody in the first HAE treatment.

18. The method of claim 1, wherein the subject is a human patient who is free of a long-term prophylaxis for HAE, or an HAE treatment involving an angiotensin-converting enzyme (ACE) inhibitor, an estrogen-containing medication, or an androgen prior to the first HAE treatment, during the first HAE treatment, and/or of during (i) and (ii).

19. The method of claim 1, wherein the first HAE treatment period is 26 weeks or longer.

* * * * *

UNITED STATES PATENT AND TRADEMARK OFFICE
CERTIFICATE OF CORRECTION

PATENT NO. : 11,286,307 B2
APPLICATION NO. : 16/061103
DATED : March 29, 2022
INVENTOR(S) : Burt Adelman et al.

Page 1 of 1

It is certified that error appears in the above-identified patent and that said Letters Patent is hereby corrected as shown below:

In the Claims

In Claim 18, at Column 55, Line 10, "the first HAE treatment, and/or of during (i) and (ii)" should be changed to --the first HAE treatment, and/or during (i) and (ii)--

Signed and Sealed this
Thirty-first Day of May, 2022

Katherine Kelly Vidal
*Director of the United States Patent and Trademark Office*

SEQUENCE LISTING

```
<160> NUMBER OF SEQ ID NOS: 10

<210> SEQ ID NO 1
<211> LENGTH: 469
<212> TYPE: PRT
<213> ORGANISM: Artificial Sequence
<220> FEATURE:
<223> OTHER INFORMATION: Synthetic Polypeptide

<400> SEQUENCE: 1

Met Gly Trp Ser Cys Ile Leu Phe Leu Val Ala Thr Ala Thr Gly Ala
1               5                   10                  15

His Ser Glu Val Gln Leu Leu Glu Ser Gly Gly Gly Leu Val Gln Pro
            20                  25                  30

Gly Gly Ser Leu Arg Leu Ser Cys Ala Ala Ser Gly Phe Thr Phe Ser
        35                  40                  45

His Tyr Ile Met Met Trp Val Arg Gln Ala Pro Gly Lys Gly Leu Glu
    50                  55                  60

Trp Val Ser Gly Ile Tyr Ser Ser Gly Gly Ile Thr Val Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Tyr Arg Arg Ile Gly Val Pro Arg Arg Asp Glu Phe Asp
        115                 120                 125

Ile Trp Gly Gln Gly Thr Met Val Thr Val Ser Ser Ala Ser Thr Lys
    130                 135                 140
```

-continued

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
        180                 185                 190

Phe Pro Ala Val Leu Gln Ser Ser Gly Leu Tyr Ser Leu Ser Ser Val
    195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
        260                 265                 270

Thr Leu Met Ile Ser Arg Thr Pro Glu Val Thr Cys Val Val Val Asp
    275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
        340                 345                 350

Ala Pro Ile Glu Lys Thr Ile Ser Lys Ala Lys Gly Gln Pro Arg Glu
    355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
        420                 425                 430

Leu Thr Val Asp Lys Ser Arg Trp Gln Gln Gly Asn Val Phe Ser Cys
    435                 440                 445

Ser Val Met His Glu Ala Leu His Asn His Tyr Thr Gln Lys Ser Leu
450                 455                 460

Ser Leu Ser Pro Gly
465

<210> SEQ ID NO 2
<211> LENGTH: 231
<212> TYPE: PRT
<213> ORGANISM: Artificial Sequence
<220> FEATURE:
<223> OTHER INFORMATION: Synthetic Polypeptide

<400> SEQUENCE: 2

Met Gly Trp Ser Cys Ile Leu Phe Leu Val Ala Thr Ala Thr Gly Ala
1               5                   10                  15

His Ser Asp Ile Gln Met Thr Gln Ser Pro Ser Thr Leu Ser Ala Ser
            20                  25                  30

```
Val Gly Asp Arg Val Thr Ile Thr Cys Arg Ala Ser Gln Ser Ile Ser
            35                  40                  45

Ser Trp Leu Ala Trp Tyr Gln Gln Lys Pro Gly Lys Ala Pro Lys Leu
 50                  55                  60

Leu Ile Tyr Lys Ala Ser Thr Leu Glu Ser Gly Val Pro Ser Arg Phe
 65                  70                  75                  80

Ser Gly Ser Gly Ser Gly Thr Glu Phe Thr Leu Thr Ile Ser Ser Leu
                 85                  90                  95

Gln Pro Asp Asp Phe Ala Thr Tyr Tyr Cys Gln Gln Tyr Asn Thr Tyr
            100                 105                 110

Trp Thr Phe Gly Gln Gly Thr Lys Val Glu Ile Lys Arg Thr Val Ala
            115                 120                 125

Ala Pro Ser Val Phe Ile Phe Pro Pro Ser Asp Glu Gln Leu Lys Ser
130                 135                 140

Gly Thr Ala Ser Val Val Cys Leu Leu Asn Asn Phe Tyr Pro Arg Glu
145                 150                 155                 160

Ala Lys Val Gln Trp Lys Val Asp Asn Ala Leu Gln Ser Gly Asn Ser
                165                 170                 175

Gln Glu Ser Val Thr Glu Gln Asp Ser Lys Asp Ser Thr Tyr Ser Leu
            180                 185                 190

Ser Ser Thr Leu Thr Leu Ser Lys Ala Asp Tyr Glu Lys His Lys Val
            195                 200                 205

Tyr Ala Cys Glu Val Thr His Gln Gly Leu Ser Ser Pro Val Thr Lys
            210                 215                 220

Ser Phe Asn Arg Gly Glu Cys
225                 230

<210> SEQ ID NO 3
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 3

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser His Tyr
             20                  25                  30

Ile Met Met Trp Val Arg Gln Ala Pro Gly Lys Gly Leu Glu Trp Val
             35                  40                  45

Ser Gly Ile Tyr Ser Ser Gly Gly Ile Thr Val Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Tyr Arg Arg Ile Gly Val Pro Arg Arg Asp Glu Phe Asp Ile Trp
            100                 105                 110

Gly Gln Gly Thr Met Val Thr Val Ser Ser
            115                 120

<210> SEQ ID NO 4
<211> LENGTH: 106
<212> TYPE: PRT
<213> ORGANISM: Artificial Sequence
```

<220> FEATURE:
<223> OTHER INFORMATION: Synthetic Polypeptide

<400> SEQUENCE: 4

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Trp Thr
                85                  90                  95

Phe Gly Gln Gly Thr Lys Val Glu Ile Lys
            100                 105

<210> SEQ ID NO 5
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 5

His Tyr Ile Met Met
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 6

Gly Ile Tyr Ser Ser Gly Gly Ile Thr Val Tyr Ala Asp Ser Val Lys
1               5                   10                  15

Gly

<210> SEQ ID NO 7
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 7

Arg Arg Ile Gly Val Pro Arg Arg Asp Glu Phe Asp Ile
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 8

Arg Ala Ser Gln Ser Ile Ser Ser Trp Leu Ala
1               5                   10

```
<210> SEQ ID NO 9
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 9

Lys Ala Ser Thr Leu Glu Ser
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 10

Gln Gln Tyr Asn Thr Tyr Trp Thr
1               5
```